US008846415B2

(12) United States Patent
Duffy et al.

(10) Patent No.: US 8,846,415 B2
(45) Date of Patent: *Sep. 30, 2014

(54) ULTRA-SENSITIVE DETECTION OF MOLECULES ON SINGLE MOLECULE ARRAYS

(75) Inventors: David C. Duffy, Somerville, MA (US); Evan Ferrell, Brighton, MA (US); Jeffrey D. Randall, Canton, MA (US); David M. Rissin, Somerville, MA (US); David R. Walt, Boston, MA (US)

(73) Assignee: Quanterix Corporation, Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/527,210

(22) Filed: Jun. 19, 2012

(65) Prior Publication Data

US 2014/0243223 A1    Aug. 28, 2014

Related U.S. Application Data

(63) Continuation of application No. 12/236,486, filed on Sep. 23, 2008, now Pat. No. 8,222,047.

(51) Int. Cl.
*G01N 33/543* (2006.01)

(52) U.S. Cl.
USPC ............................................................ 436/518

(58) Field of Classification Search
None
See application file for complete search history.

(56) References Cited

U.S. PATENT DOCUMENTS

| | | | |
|---|---|---|---|
| 3,712,986 A | 1/1973 | Collings | |
| 4,200,110 A | 4/1980 | Peterson et al. | |
| 4,232,119 A | 11/1980 | Carlsson et al. | |
| 4,631,211 A | 12/1986 | Houghten | |
| 4,780,421 A * | 10/1988 | Kameda et al. | 436/518 |
| 4,883,642 A | 11/1989 | Bisconte | |
| 4,907,037 A | 3/1990 | Boisde et al. | |
| 4,924,870 A | 5/1990 | Wlodarczyk et al. | |
| 4,962,037 A | 10/1990 | Jett et al. | |
| 5,026,159 A | 6/1991 | Allen et al. | |
| 5,028,535 A | 7/1991 | Buechler et al. | |
| 5,089,391 A | 2/1992 | Buechler et al. | |
| 5,091,300 A * | 2/1992 | Hurni et al. | 435/5 |
| 5,108,961 A | 4/1992 | Zhong et al. | |
| 5,152,816 A | 10/1992 | Berkey | |
| 5,190,857 A | 3/1993 | Allen et al. | |
| 5,196,306 A | 3/1993 | Bobrow et al. | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,298,741 A | 3/1994 | Walt et al. | |
| 5,315,375 A | 5/1994 | Allen | |
| 5,320,814 A | 6/1994 | Walt et al. | |
| 5,329,461 A | 7/1994 | Allen et al. | |
| 5,374,395 A | 12/1994 | Robinson et al. | |
| 5,405,783 A | 4/1995 | Pirrung et al. | |
| 5,445,934 A | 8/1995 | Fodor et al. | |
| 5,468,846 A | 11/1995 | Ichikawa et al. | |
| 5,488,567 A | 1/1996 | Allen et al. | |
| 5,512,490 A | 4/1996 | Walt et al. | |
| 5,532,138 A | 7/1996 | Singh et al. | |
| 5,532,379 A | 7/1996 | Fujimoto | |
| 5,545,531 A | 8/1996 | Rava et al. | |
| 5,583,001 A | 12/1996 | Bobrow et al. | |
| 5,620,850 A | 4/1997 | Bamdad et al. | |
| 5,633,972 A | 5/1997 | Walt et al. | |
| 5,690,894 A | 11/1997 | Pinkel et al. | |
| 5,700,637 A | 12/1997 | Southern | |
| 5,731,158 A | 3/1998 | Bobrow et al. | |
| 5,770,455 A | 6/1998 | Cargill et al. | |
| 5,807,522 A | 9/1998 | Brown et al. | |
| 5,814,524 A | 9/1998 | Walt et al. | |
| 5,885,529 A * | 3/1999 | Babson et al. | 422/65 |
| 5,900,481 A | 5/1999 | Lough et al. | |
| 5,981,180 A | 11/1999 | Chandler et al. | |
| 6,001,564 A | 12/1999 | Bergeron et al. | |
| 6,007,690 A | 12/1999 | Nelson et al. | |
| 6,013,445 A | 1/2000 | Albrecht et al. | |
| 6,023,540 A | 2/2000 | Walt et al. | |

(Continued)

FOREIGN PATENT DOCUMENTS

AU    199956253 B2    3/2000
DE    19540098 A1    4/1997

(Continued)

OTHER PUBLICATIONS

International Search Report and Written Opinion for International Application No. PCT/US2009/005250, mailed Mar. 22, 2010.
International Preliminary Report on Patentability, Chapter 1, for International Application No. PCT/US2009/005250, mailed Apr. 7, 2011.
International Search Report and Written Opinion for International Application No. PCT/US2009/005248, mailed Mar. 1, 2010.
International Preliminary Report on Patentability, Chapter 1, for International Application No. PCT/US2009/005248, mailed Apr. 7, 2011.
International Search Report and Written Opinion for International Application No. PCT/US2011/026645, mailed Nov. 24, 2011.
International Preliminary Report on Patentability for PCT/US2011/026645 mailed Sep. 13, 2012.

(Continued)

*Primary Examiner* — Ann Lam
(74) *Attorney, Agent, or Firm* — Wolf, Greenfield & Sacks, P.C.

(57) ABSTRACT

The present invention relates to systems and methods for detecting analyte molecules or particles in a fluid sample and in some cases, determining a measure of the concentration of the molecules or particles in the fluid sample. Methods of the present invention may comprise immobilizing a plurality of analyte molecules or particles to form a plurality of complexes, releasing at least a portion of some of the plurality of complexes, determining at least a portion of the plurality of complexes released, and determining a measure of the concentration of the analyte molecules or particles in a fluid sample.

23 Claims, 27 Drawing Sheets

(56) References Cited

U.S. PATENT DOCUMENTS

| | | | |
|---|---|---|---|
| 6,133,436 A | 10/2000 | Koster et al. | |
| 6,143,496 A | 11/2000 | Brown et al. | |
| 6,156,270 A | 12/2000 | Buechler | |
| 6,174,695 B1 | 1/2001 | Hammock et al. | |
| 6,210,910 B1 | 4/2001 | Walt et al. | |
| 6,266,459 B1 | 7/2001 | Walt et al. | |
| 6,285,807 B1 | 9/2001 | Walt et al. | |
| 6,327,410 B1 | 12/2001 | Walt et al. | |
| 6,329,139 B1 | 12/2001 | Nova et al. | |
| 6,368,874 B1 | 4/2002 | Gallop et al. | |
| 6,377,721 B1 | 4/2002 | Walt et al. | |
| 6,388,746 B1 | 5/2002 | Eriksson et al. | |
| 6,396,995 B1 | 5/2002 | Stuelpnagel et al. | |
| 6,406,845 B1 | 6/2002 | Walt et al. | |
| 6,432,630 B1* | 8/2002 | Blankenstein | 435/4 |
| 6,482,593 B2 | 11/2002 | Walt et al. | |
| 6,582,908 B2 | 6/2003 | Fodor et al. | |
| 6,602,702 B1* | 8/2003 | McDevitt et al. | 435/288.7 |
| 6,620,584 B1 | 9/2003 | Chee et al. | |
| 6,635,452 B1 | 10/2003 | Monforte et al. | |
| 6,667,159 B1 | 12/2003 | Walt et al. | |
| 6,713,309 B1 | 3/2004 | Anderson et al. | |
| 6,714,303 B2 | 3/2004 | Ivarsson | |
| 6,821,449 B2 | 11/2004 | Caplen et al. | |
| 6,858,394 B1 | 2/2005 | Chee et al. | |
| 6,859,570 B2 | 2/2005 | Walt | |
| 6,878,345 B1 | 4/2005 | Astle | |
| 6,929,924 B2 | 8/2005 | Bouanani et al. | |
| 6,942,968 B1 | 9/2005 | Dickinson et al. | |
| 6,943,034 B1 | 9/2005 | Winkler et al. | |
| 6,991,939 B2 | 1/2006 | Walt et al. | |
| 6,999,657 B2 | 2/2006 | Walt | |
| 7,056,746 B2 | 6/2006 | Seul et al. | |
| 7,060,431 B2 | 6/2006 | Chee et al. | |
| 7,115,884 B1 | 10/2006 | Walt et al. | |
| 7,211,390 B2 | 5/2007 | Rothberg et al. | |
| 7,244,559 B2 | 7/2007 | Rothberg et al. | |
| 7,250,267 B2 | 7/2007 | Walt et al. | |
| 7,264,929 B2 | 9/2007 | Rothberg et al. | |
| 7,348,181 B2 | 3/2008 | Walt et al. | |
| 7,480,433 B2 | 1/2009 | Walt et al. | |
| 7,572,581 B2 | 8/2009 | Gelfand et al. | |
| 7,651,841 B2 | 1/2010 | Song et al. | |
| 7,759,062 B2 | 7/2010 | Allawi et al. | |
| 7,776,553 B2 | 8/2010 | Love et al. | |
| 7,838,250 B1 | 11/2010 | Goix et al. | |
| 8,222,047 B2* | 7/2012 | Duffy et al. | 436/518 |
| 8,236,574 B2* | 8/2012 | Duffy et al. | 436/518 |
| 8,415,171 B2* | 4/2013 | Rissin et al. | 436/518 |
| 8,460,878 B2 | 6/2013 | Walt et al. | |
| 8,460,879 B2 | 6/2013 | Walt et al. | |
| 8,492,098 B2 | 7/2013 | Walt et al. | |
| 2002/0009391 A1 | 1/2002 | Marquiss et al. | |
| 2002/0090650 A1 | 7/2002 | Empedocles et al. | |
| 2002/0122612 A1 | 9/2002 | Walt et al. | |
| 2003/0027126 A1 | 2/2003 | Walt et al. | |
| 2003/0091475 A1 | 5/2003 | Yu et al. | |
| 2003/0198573 A1 | 10/2003 | Forood et al. | |
| 2004/0038426 A1 | 2/2004 | Manalis | |
| 2004/0053322 A1 | 3/2004 | McDevitt et al. | |
| 2004/0071599 A1 | 4/2004 | Rusch et al. | |
| 2004/0072278 A1 | 4/2004 | Chou et al. | |
| 2004/0086426 A1 | 5/2004 | Vann et al. | |
| 2004/0101918 A1 | 5/2004 | Cauci | |
| 2004/0142386 A1 | 7/2004 | Rigler et al. | |
| 2004/0248325 A1 | 12/2004 | Bukusoglu | |
| 2004/0253624 A1 | 12/2004 | Smith et al. | |
| 2004/0259237 A1 | 12/2004 | Kellogg et al. | |
| 2005/0112655 A1 | 5/2005 | Banerjee et al. | |
| 2005/0130173 A1 | 6/2005 | Leamon et al. | |
| 2005/0130188 A1 | 6/2005 | Walt et al. | |
| 2005/0131650 A1 | 6/2005 | Andersson et al. | |
| 2005/0164289 A1 | 7/2005 | Quate et al. | |
| 2005/0244308 A1 | 11/2005 | Tanaami et al. | |
| 2005/0266433 A1 | 12/2005 | Kapur et al. | |
| 2006/0006067 A1 | 1/2006 | Unger | |
| 2006/0013543 A1 | 1/2006 | Walt et al. | |
| 2006/0040297 A1 | 2/2006 | Leamon et al. | |
| 2006/0068409 A1 | 3/2006 | Phan et al. | |
| 2006/0078998 A1 | 4/2006 | Puskas et al. | |
| 2006/0084183 A1 | 4/2006 | Henriksen | |
| 2006/0139635 A1 | 6/2006 | Kersey et al. | |
| 2007/0040095 A1 | 2/2007 | Walt et al. | |
| 2007/0074972 A1 | 4/2007 | Nassef et al. | |
| 2007/0116607 A1 | 5/2007 | Wang et al. | |
| 2007/0259381 A1 | 11/2007 | Walt et al. | |
| 2007/0259385 A1 | 11/2007 | Walt et al. | |
| 2007/0259448 A1 | 11/2007 | Walt et al. | |
| 2008/0032324 A1 | 2/2008 | Walt et al. | |
| 2008/0064113 A1 | 3/2008 | Goix | |
| 2009/0036324 A1 | 2/2009 | Fan et al. | |
| 2009/0142755 A1 | 6/2009 | Albitar | |
| 2009/0149341 A1 | 6/2009 | Walt et al. | |
| 2009/0156425 A1 | 6/2009 | Walt et al. | |
| 2009/0170728 A1 | 7/2009 | Walt et al. | |
| 2009/0239308 A1 | 9/2009 | Dube et al. | |
| 2009/0254180 A1 | 10/2009 | Pazanowski | |
| 2009/0289834 A1 | 11/2009 | Devensky | |
| 2009/0307772 A1 | 12/2009 | Markham | |
| 2010/0075355 A1* | 3/2010 | Duffy et al. | 435/18 |
| 2010/0075407 A1 | 3/2010 | Duffy et al. | |
| 2010/0075439 A1* | 3/2010 | Duffy et al. | 436/518 |
| 2010/0075862 A1 | 3/2010 | Duffy et al. | |
| 2010/0140289 A1 | 6/2010 | Knobel et al. | |
| 2010/0189338 A1* | 7/2010 | Lin et al. | 382/133 |
| 2010/0192573 A1 | 8/2010 | Hamilton et al. | |
| 2010/0204335 A1 | 8/2010 | Beddingfield et al. | |
| 2011/0183330 A1 | 7/2011 | Lo et al. | |
| 2011/0195852 A1 | 8/2011 | Walt et al. | |
| 2011/0212462 A1* | 9/2011 | Duffy et al. | 435/7.1 |
| 2011/0212537 A1 | 9/2011 | Duffy et al. | |
| 2011/0212848 A1 | 9/2011 | Duffy et al. | |
| 2011/0245097 A1 | 10/2011 | Rissin et al. | |
| 2012/0196774 A1 | 8/2012 | Fournier et al. | |
| 2012/0214160 A1 | 8/2012 | Deng et al. | |
| 2012/0277114 A1 | 11/2012 | Duffy et al. | |
| 2012/0289428 A1 | 11/2012 | Duffy et al. | |
| 2013/0165342 A1 | 6/2013 | Rissin et al. | |

FOREIGN PATENT DOCUMENTS

| | | |
|---|---|---|
| EP | 0 805 215 A2 | 11/1997 |
| EP | 1 180 679 A1 | 2/2002 |
| EP | 1 259 810 B1 | 11/2006 |
| EP | 1 721 657 A1 | 11/2006 |
| JP | 2001-269196 A | 10/2001 |
| JP | 2002-506200 A | 2/2002 |
| JP | 2002-525587 A | 8/2002 |
| JP | 2002-526743 A | 8/2002 |
| JP | 2004-354164 A | 12/2004 |
| JP | 2005-518553 A | 6/2005 |
| JP | 2006-511792 A | 4/2006 |
| WO | WO 88/05533 A1 | 7/1988 |
| WO | WO 93/06121 A1 | 4/1993 |
| WO | WO 93/24517 A2 | 12/1993 |
| WO | WO 95/25116 A1 | 9/1995 |
| WO | WO 95/32425 A1 | 11/1995 |
| WO | WO 95/35506 A2 | 12/1995 |
| WO | WO 97/27326 A1 | 7/1997 |
| WO | WO 98/50782 A2 | 11/1998 |
| WO | WO 99/45357 A2 | 9/1999 |
| WO | WO 99/58948 A2 | 11/1999 |
| WO | WO 00/04372 A1 | 1/2000 |
| WO | WO 00/47996 A2 | 8/2000 |
| WO | WO 01/57520 A2 | 8/2001 |
| WO | WO 03/054142 A2 | 7/2003 |
| WO | WO 03/073817 A2 | 9/2003 |
| WO | WO 2004/065000 A1 | 8/2004 |
| WO | WO 2004/083443 A1 | 9/2004 |
| WO | WO 2005/019419 A2 | 3/2005 |
| WO | WO 2005/023414 A1 | 3/2005 |
| WO | WO 2005/033283 A2 | 4/2005 |
| WO | WO 2005/054431 A2 | 6/2005 |
| WO | WO 2006/007726 A1 | 1/2006 |

(56) References Cited

FOREIGN PATENT DOCUMENTS

| WO | WO 2006/055739 A2 | 5/2006 |
|---|---|---|
| WO | WO 2006/078289 A2 | 7/2006 |
| WO | WO 2006/102297 A1 | 9/2006 |
| WO | WO 2006/108180 A2 | 10/2006 |
| WO | WO 2007/044091 A2 | 4/2007 |
| WO | WO 2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/084192 A2 | 7/2007 |
| WO | WO 2007/098148 A2 | 8/2007 |
| WO | WO 2007/114947 A2 | 10/2007 |
| WO | WO 2008/048371 A2 | 4/2008 |
| WO | WO 2009/029073 A1 | 3/2009 |
| WO | WO 2010/039180 A2 | 4/2010 |
| WO | WO 2011/109372 A1 | 9/2011 |

OTHER PUBLICATIONS

International Search Report and Written Opinion for International Application No. PCT/US2011/026657, mailed May 24, 2011.
International Preliminary Report on Patentability for PCT/US2011/026657 mailed Sep. 13, 2012.
International Search Report and Written Opinion for International Application No. PCT/US2011/026665, mailed Jul. 5, 2011.
International Preliminary Report on Patentability for PCT/US2011/026665 mailed Sep. 13, 2012.
Invitation to Pay Additional Fees for PCT/US2012/022923 mailed Apr. 2, 2012.
International Search Report and Written Opinion for International Application No. PCT/US2012/022923 mailed Jun. 25, 2012.
International Preliminary Report on Patentability for PCT/US2012/022923 mailed Aug. 8, 2013.
International Search Report and Written Opinion for International Application No. PCT/US2007/019184, mailed Jun. 19, 2008.
International Preliminary Report on Patentability, Chapter 1, for International Application No. PCT/US2007/019184, mailed Mar. 11, 2010.
European Search Report for European Application No. 07751131.9, mailed Sep. 8, 2009.
Extended European Search Report for European Application No. 12177276 8 mailed Nov. 26, 2012.
International Search Report and Written Opinion for International Application No. PCT/US2007/004349, mailed Aug. 21, 2008.
International Preliminary Report on Patentability, Chapter 1, for International Application No. PCT/US2007/004349 dated Sep. 25, 2008.
International Preliminary Report on Patentability, Chapter 2, for International Application No. PCT/U52007/004349 dated Mar. 23, 2009.
Office Action for U.S. Appl. No. 12/236,484, filed Sep. 23, 2008, published as US 2010-0075862 on Mar. 25, 2010, which Office Action is dated Sep. 9, 2010, and claims as pending for U.S. Appl. No. 12/236,484 as of Sep. 9, 2010.
Office Action for U.S. Appl. No. 12/236,484, filed Sep. 23, 2008, published as US 2010-0075862 on Mar. 25, 2010, which Office Action is dated Apr. 13, 2011, and claims as pending for U.S. Appl. No. 12/236,484 as of Apr. 13, 2011.
Office Action for U.S. Appl. No. 12/236,486, filed Sep. 23, 2008, published as US 2010-0075407 on Mar. 25, 2010, which Office Action is dated Nov. 23, 2011, and claims as pending for U.S. Appl. No. 12/236,486 as of Nov. 23, 2011.
Notice of Allowance for U.S. Appl. No. 12/236,486, filed Sep. 23, 2008, published as US-2010-0075407 on Mar. 25, 2010, which Notice of Allowance is dated Mar. 22, 2012 , and claims as allowed for U.S. Appl. No. 12/236,486 as of Mar. 25, 2010.
Office Action for U.S. Appl. No. 12/236,488, filed Sep. 23, 2008, published as US 2010-0075439 on Mar. 25, 2010, which Office Action is dated Aug. 2, 2010, and claims as pending for U.S. Appl. No. 12/236,488 as of Aug. 2, 2010.

Office Action for U.S. Appl. No. 12/731,130, filed Mar. 24, 2010, published as US 2011-0212848 on Sep. 1, 2011, which Office Action is dated Mar. 28, 2012, and claims as pending for U.S. Appl. No. 12/731,130 as of Mar. 28, 2012.
Notice of Allowance for U.S. Appl. No. 12/731,130, filed Mar. 24, 2010, published as US 2011-0212848 on Sep. 1, 2011, which Notice of Allowance is dated Jun. 1, 2012, and allowed claims for U.S. Appl. No. 12/731,130 as of Jun. 1, 2012.
Office Action for U.S. Appl. No. 12/731,135, filed Mar. 24, 2010, published as US 20110212462 on Sep. 1, 2011, which Office Action is dated May 23, 2013, and claims as pending for U.S. Appl. No. 12/731,135 as of May 23, 2013.
Office Action for U.S. Appl. No. 12/731,136 filed Mar. 24, 2010, published as 2011-0212537 on Sep. 1, 2011, which Office Action is dated Jun. 15, 2012, and claims as pending for Office Action for U.S. Appl. No. 12/731,136 as of Jun. 15, 2012.
Notice of Allowance for U.S. Appl. No. 12/731,136, filed Mar. 24, 2010, published as 2011-0212537 on Sep. 1, 2011, which Notice of Allowance is dated Nov. 15, 2012, and claims as allowed for U.S. Appl. No. 12/731,136 as of Nov. 15, 2012.
Office Action for U.S. Appl. No. 11/707,385, filed Feb. 16, 2007, published as US 2007-0259448 on Nov. 8, 2007, which Office Action is dated Jan. 26, 2010, and claims as pending for U.S. Appl. No. 11/707,385 as of Jan. 26, 2010.
Office Action for U.S. Appl. No. 11/707,385 filed Feb. 16, 2007, published as US 2007-0259448 on Nov. 8, 2007, which Office Action is dated Mar. 16, 2009, and claims as pending for U.S. Appl. No. 11/707,385 as of Mar. 16, 2009.
Office Action for U.S. Appl. No. 11/707,385, filed Feb. 16, 2007, published as US 2007-0259448 on Nov. 8, 2007, which Office Action is dated Sep. 27, 2012, and claims as pending for U.S. Appl. No. 11/707,385 as of Sep. 27, 2012.
Notice of Allowance for U.S. Appl. No. 11/707,385, filed Feb. 16, 2007, published as US-2007-0259448 on Nov. 8, 2007, which Notice of Allowance is dated Feb. 25, 2013, and claims as allowed for Office Action for U.S. Appl. No. 11/707,385 as of Feb. 25, 2013.
Office Action for U.S. Appl. No. 11/707,383, filed Feb. 16, 2007, published as US 2007-0259385 on Nov. 8, 2007, which Office Action is dated Mar. 16, 2009, and claims as pending for U.S. Appl. No. 11/707,383 as of Mar. 16, 2009.
Office Action for U.S. Appl. No. 11/707,383, filed Feb. 16, 2007, published as US 2007-0259385 on Nov. 8, 2007, which Office Action is dated Nov. 27, 2009, and claims as pending for U.S. Appl. No. 11/707,383 as of Nov. 27, 2009.
Office Action for U.S. Appl. No. 11/707,383, filed Feb. 16, 2007, published as US 2007-0259385 on Nov. 8, 2007, which Office Action is dated Sep. 27, 2012, and claims as pending for U.S. Appl. No. 11/707,383 as of Sep. 27, 2012.
Notice of Allowance for U.S. Appl. No. 11/707,383, filed Feb. 16, 2007, published as US 2007-0259385 on Nov. 8, 2007, which Office Action is dated Feb. 8, 2013, and claims as allowed for U.S. Appl. No. 11/707,383 as of Feb. 8, 2013.
Office Action for U.S. Appl. No. 11/707,384, filed Feb. 16, 2007, published as US 2007-0259381 on Nov. 8, 2007, which Office Action is dated Mar. 16, 2009, and claims as pending for U.S. Appl. No. 11/707,384 as of Mar. 16, 2009.
Office Action for U.S. Appl. No. 11/707,384, filed Feb. 16, 2007, published as US 2007-0259381 on Nov. 8, 2007, which Office Action is dated Dec. 2, 2009, and claims as pending for U.S. Appl. No. 11/707,384 as of Dec. 2, 2009.
Office Action for U.S. Appl. No. 11/707, 384, filed Feb. 16, 2007, published as US 2007-0259381 on Nov. 8, 2007, which Office Action is dated Sep. 27, 2012, and claims as pending for U.S. Appl. No. 11/707, 384 as of Sep. 27, 2012.
Notice of Allowance for U.S. Appl. No. 11/707,384, filed Feb. 16, 2007, published as US 2007-0259381 on Nov. 8, 2007, which Office Action is dated Feb. 6, 2013, and claims as allowed for U.S. Appl. No. 11/707,384 as of Feb. 6, 2013.
[No Author Listed] Novel test following prostate surgery could detect cancer recurrence earlier. AACR Press Release. Sep. 29, 2010. Last accessed at http://www.aacr.org/home/public--media/aacr-press-releases.aspx?d=2072 on Jan. 31, 2012. 2 pages.

(56) References Cited

OTHER PUBLICATIONS

[No Author Listed] Quanterix corporation awarded $185,000 grant from the National Cancer Institute. Quanterix Press Release. Sep. 30, 2008. Last accessed at http://www.quanterix.com/news/pressReleases/SBIR1Grant.html on Jan. 31, 2012. 1 page.
[No Author Listed] Quanterix corporation raises $15 million in series A financing. Quanterix Press Release. Aug. 25, 2008. Last accessed at http://www.quanterix.com/news/pressReleases/seriesAFunding.html on Jan. 31, 2012. 2 pages.
[No Author Listed] Single molecule arrays for digital detection in complex samples. Quanterix Corporation. IQT Technology Focus Day. Mar. 25, 2010. PowerPoint presentation. 30 pages.
Adams et al., Encoded fiber-optic microsphere arrays for probing protein-carbohydrate interactions. Angewandte Chemie. 2003; 115:5475-5478.
Agrawal et al., Nanometer-scale mapping and single-molecule detection with color-coded nanoparticle probes. Proc Natl Acad Sci U S A. Mar. 4, 2008;105(9):3298-303. Epub Feb. 27, 2008.
Agrawal et al., Single-bead immunoassays using magnetic microparticles and spectral-shifting quantum dots. J Agric Food Chem. May 16, 2007; 55(10):3778-82. Epub Apr. 25, 2007.
Ahn et al., Detection of *Salmonella* spp. Using microsphere-based, fiber-optic DNA microarrays. Anal Chem. Aug. 1, 2005; 77(15):5041-7.
Ahn et al., Fiber-optic microarray for simultaneous detection of multiple harmful algal bloom species. Appl Environ Microbiol. Sep. 2006; 72(9):5742-9.
Albert et al., Automatic decoding of sensor types within randomly ordered, high-density optical sensor arrays. Anal Bioanal Chem. Apr. 2002; 373(8):792-802. Epub Jul. 27, 2002.
Albert et al., Cross-reactive chemical sensor arrays. Chem Rev. Jul. 12, 2000; 100(7):2595-626.
Albert et al., Information coding in artificial olfaction multisensor arrays. Anal Chem. Aug. 15, 2003; 75(16):4161-7.
Albert et al., Optical multibead arrays for simple and complex odor discrimination. Anal Chem. Jun. 1, 2001; 73(11):2501-8.
Angenendt et al., Subnanoliter enzymatic assays on microarrays. Proteomics. Feb. 2005;5(2):420-5.
Arnaud, Observing single enzymes at work. Chemical & Engineering News. Oct. 2007; 85(44): 8(44): 8.
Beer et al., On-chip, real-time, single-copy polymerase chain reaction in picoliter droplets. Anal Chem. Nov. 15, 2007;79(22):8471-5. Epub Oct. 11, 2007. Abstract only.
Bencic-Nagale et al., Extending the longevity of fluorescence-based sensor arrays using adaptive exposure. Anal Chem. Oct. 1, 2005; 77(19):6155-62.
Bhat et al., Single molecule detection in nanofluidic digital array enables accurate measurement of DNA copy number. Anal Bioanal Chem. May 2009;394(2):457-67. Epub Mar. 15, 2009.
Biran et al., Optical imaging fiber-based live bacterial cell array biosensor. Anal Biochem. Apr. 1, 2003; 315(1):106-13.
Biran et al., Optical imaging fiber-based single live cell arrays: a high-density cell assay platform. Anal Chem. Jul. 1, 2002; 74(13):3046-54.
Blake et al., Phenotypic consequences of promoter-mediated transcriptional noise. Mol Cell. Dec. 28, 2006; 24(6):853-65.
Blicharz et al., Detection of inflammatory cytokines using a fiber optic microsphere immunoassay array. *Proc. SPIE*. 2006; 6380, 638010-1-638010-6.
Blicharz et al., Fiber-optic microsphere-based antibody array for the analysis of inflammatory cytokins in saliva. Anal. Chem. 2009;81(6):2106-14.
Blicharz et al., Use of colorimetric test strips for monitoring the effect of hemodialysis on salivary nitrite and uric acid in patients with end-stage renal disease: a proof of principle. Clin Chem. Sep. 2008; 54(9):1473-80. Epub Aug. 1, 2008.
Bourzac, Next-generation diagnostics: a startup can detect tiny traces of cancer markers in blood samples. Technol Rev. May 13, 2008. Last accessed at http://www.technologyreview.com/Biztech/20760/?a=f on Feb. 2, 2012. 2 pages.

Bowden et al., Development of a microfluidic platform with an optical imaging microarray capable of attomolar target DNA detection. Anal Chem. Sep. 1, 2005; 77(17):5583-8. Epub Aug. 4, 2005.
Boyden, The chemotactic effect of mixtures of antibody and antigen on polymorphonuclear leucocytes. J Exp Med. Mar. 1, 1962;115:453-66.
Brehm-Stecher et al., Single-cell microbiology: tools, technologies, and applications. Microbiol Mol Biol Rev. Sep. 2004; 68(3):538-59.
Brogan et al., Optical fiber-based sensors: application to chemical biology. Curr Opin Chem Biol. Oct. 2005; 9(5):494-500. Epub Aug. 24, 2005.
Bronk et al., Combined imaging and chemical sensing using a single optical imaging fiber. Anal Chem. Sep. 1, 1995; 67(17):2750-7.
Bronk et al., Fabrication of patterned sensor arrays with aryl azides on a polymer-coated imaging optical fiber bundle. Anal Chem. Oct. 15, 1994; 66(20):3519-20.
Burton et al., A microfluidic chip-compatible bioassay based on single-molecule detection with high sensitivity and multiplexing. Lab Chip. Apr. 7, 2010; 10(7):843-51. Epub Jan. 14, 2010.
Campian, Colored and fluorescent solid supports. Innovation and Perspectives in Solid Phase Synthesis. Ed. R. Epton, Mayflower Worldwide Limited, Birmingham. Ch. 77. 1994:469-472.
Chen et al., Microfabricated arrays of cylindrical wells facilitate single-molecule enzymology of alpha-chymotrypsin. Biotechnol Prog. Jul.-Aug. 2009; 25(4):929-37.
Chin et al., Editor's Choice: Distinctive individualism. Science. Apr. 4, 2008;320:21.
Chon et al., Characterization of single-cell migration using a computer-aided fluorescence time-lapse videomicroscopy system. Anal Biochem. Oct. 15, 1997;252(2):246-54.
Deutsch et al., Apparatus for high-precision repetitive sequential optical measurement of living cells. Cytometry. Jul. 1, 1994; 16(3):214-26.
Dicesare et al., Individual cell migration analysis using fiber-optic bundles. Anal Bioanal Chem. May 2005; 382(1):37-43. Epub Apr. 1, 2005.
Dickinson et al., A chemical-detecting system based on a cross-reactive optical sensor array. Nature. Aug. 22, 1996; 382(6593):697-700.
Dickinson et al., Convergent, self-encoded bead sensor arrays in the design of an artificial. Anal Chem. Jun. 1, 1999; 71(11):2192-8.
Dickinson et al., Current trends in 'artificial-nose' technology. Trends Biotechnol. Jun. 1998; 16(6):250-8.
Duffy. Single Molecule Arrays (Simoa) for Ultrasensitive Protein Detection in Companion Diagnostics. Next Generation DX Summit. Aug. 22, 2012. PowerPoint presentation.
Egner et al., Tagging in combinatorial chemistry: the use of coloured and flurorescent beads. Chem Commun. 1997; 735-736.
Eid et al., Real-time DNA sequencing from single polymerase molecules. Science. Jan. 2, 2009; 323(5910):133-8. Epub Nov. 20, 2008.
Ekins et al al., Single-molecule Elisa. Clin Chem. Mar. 2011;57(3):372-5. Epub Oct. 13, 2010. Papers in press. Oct. 13, 2010. pp. 1-3.
English et al., Ever-fluctuating single enzyme molecules: Michaelis-Menten equation revisited. Nat Chem Biol. Feb. 2006; 2(2):87-94. Epub Dec. 25, 2005.
Epstein et al., Combinatorial decoding: an approach for universal DNA array fabrication. J Am Chem Soc. Nov. 12, 2003; 125(45):13753-9.
Epstein et al., Fluorescence-based nucleic acid detection and microarrays. Analytica Chimica Acta. 2002; 469:3-36.
Epstein et al., High-density fiber-optic genosensor microsphere array capable of zeptomole detection limits. Anal Chem. Apr. 15, 2002; 74(8):1836-40.
Epstein et al., High-density, microsphere-based fiber optic Dna microarrays. Biosens Bioelectron. May 2003 ; 18(5-6):541-6.
Epstein, et al., Fluorescence-based fibre optic arrays: a universal platform for sensing. Chem Soc Rev. Jul. 2003; 32(4):203-14.
Ferguson et al., A fiber-optic DNA biosensor microarray for the analysis of gene expression. Nat Biotechnol. Dec. 1996; 14(13):1681-4.
Ferguson et al., High-density fiber-optic DNA random microsphere array. Anal Chem. Nov. 15, 2000; 72(22):5618-24.

(56) References Cited

OTHER PUBLICATIONS

Ferguson et al., Simultaneous monitoring of pH, $CO_2$ and $O_2$ using an optical imaging fiber. Analytica Chimica Acta. 1997; 340(1-3):123-131.
Fister et al., Counting single chromophore molecules for ultrasensitive analysis and separations on microchip devices. Analytical Chemistry. 1998; 70:431-437.
Fulton et al., Advanced multiplexed analysis with the FlowMetrix system. Clin Chem. Sep. 1997; 43(9):1749-56.
Furka et al., General method for rapid synthesis of multicomponent peptide mixtures. Int J Pept Protein Res. Jun. 1991;37(6):487-93.
Gebel, Molecule counting made easy. Anal Chem. Sep. 1, 2009; 7130-7131.
Giaever et al., Micromotion of mammalian cells measured electrically. Proc Natl Acad Sci U S A. Sep. 1, 1991;88(17):7896-900.
Gorris et al., Analytical chemistry on the femtoliter scale. Angew Chem Int Ed. 2010; 49:2-18.
Gorris et al., Mechanistic aspects of horseradish peroxidase elucidated through single-molecule studies. J Am Chem Soc. May 6, 2009; 131(17):6277-82.
Gorris et al., Optical-fiber bundles. FEBS J. Nov. 2007; 274(21):5462-70. Epub Oct. 12, 2007.
Gorris et al., Stochastic inhibitor release and binding from single-enzyme molecules. Proc Natl Acad Sci U S A. Nov. 6, 2007; 104(45):17680-5. Epub Oct. 26, 2007.
Härmä et al., Europium nanoparticles and time-resolved fluorescence for ultrasensitive detection of prostate-specific antigen. Clin Chem. Mar. 2001; 47(3):561-8.
Härmä et al., Miniature single-particle immunoassay for prostate-specific antigen in serum using recombinant Fab fragments. Clin Chem. Nov. 2000; 46(11):1755-61.
Härmä et al., Zeptomole detection sensitivity of prostate-specific antigen in a rapid microtitre plate assay using time-resolved fluorescence. Luminescence. Nov.-Dec. 2000;15(6):351-5.
Hashida et al., Immune complex transfer enzyme immunoassay that is more sensitive and specific than western blotting for detection of antibody immunoglobulin G to human immunodeficiency virus type 1 in serum with recombinant pol and gag proteins as antigens. Clin Diagn Lab Immunol. Sep. 1995; 2(5):535-41.
Haugland, Handbook: A Guide to Fluorescent Probes and Labeling Technologies. Invitrogen, Eugene, OR. Molecular Probes, US. pp. 473-538.
He et al., Selective encapsulation of single cells and subcellular organdies into picoliter- and femtoliter-volume droplets. Anal Chem. Mar. 15, 2005; 77(6):1539-44.
Healey et al., Fiberoptic DNA sensor array capable of detecting point mutations. Anal Biochem. Sep. 5, 1997; 251(2):270-9.
Healey et al., Multianalyte biosensors on optical imaging bundles. Biosens Bioelectron. 1997; 12(6):521-9.
Healey et al., Photodeposition of micrometer-scale polymer patterns on optical imaging fibers. Science. Aug. 25, 1995; 269(5227):1078-80.
Hindson et al., High-throughput droplet digital PCR system for absolute quantitation of DNA copy number. Anal Chem. Nov. 15, 2011;83(22):8604-10. Epub Oct. 28, 2011.
Hirano et al., A novel method for DNA molecular counting. Nucleic Acids Symp Ser. 2000;(44):157-8.
Hirschfeld, Remote and in-situ analysis. Anal Chem. 1986; 324:618-624.
Hunsaker et al., Nucleic acid hybridization assays employing dA-tailed capture probes. II. Advanced multiple capture methods. Anal Biochem. Sep. 1989; 181(2):360-70.
Johnson et al., Identification of multiple analytes using an optical sensor array and pattern recognition neural networks. Analytical Chemistry. 1997; 69(22):4641-8.
Kiss et al., High-throughput quantitative polymerase chain reaction in picoliter droplets. Anal Chem. Dec. 1, 2008;80(23):8975-81.
Kremsky et al., Immobilization of DNA via oligonucleotides containing an aldehyde or carboxylic acid group at the 5' terminus. Nucleic Acids Res. Apr. 10, 1987; 15(7):2891-909.

Kuang et al., Living bacterial cell array for genotoxin monitoring. Anal Chem. May 15, 2004; 76(10):2902-9.
Kuang et al., Monitoring "promiscuous" drug effects on single cells of multiple cell types. Anal Biochem. Oct. 15, 2005; 345(2):320-5.
Kuang et al., Simultaneously monitoring gene expression kinetics and genetic noise in single cells by optical well arrays. Anal Chem. Nov. 1, 2004; 76(21):6282-6.
Lafratta et al., Very high density sensing arrays. Chem Rev. Feb. 2008; 108(2):614-37. Epub Jan. 30, 2008.
Lee et al., A fiber-optic microarray biosensor using aptamers as receptors. Anal Biochem. Jun. 15, 2000; 282(1):142-6.
Li et al., Detection of single-molecule DNA hybridization using enzymatic amplification in an array of femtoliter-sized reaction vessels. J Am Chem Soc. Sep. 24, 2008; 130(38):12622-3. Epub Sep. 3, 2008.
Li et al., Molecule by molecule direct and quantitative counting of antibody-protein complexes in solution. Anal Chem. Aug. 1, 2004; 76(15):4446-51.
Lu et al., Single-molecule enzymatic dynamics. Science. Dec. 4, 1998; 282(5395):1877-82.
Luo et al., Single-molecule and ensemble fluorescence assays for a functionally important conformational change in T7 DNA polymerase. Proc Natl Acad Sci U S A. Jul. 31, 2007; 104(31):12610-5. Epub Jul. 18, 2007.
Melin et al., Microfluidic large-scale integration: the evolution of design rules for biological automation. Annu Rev Biophys Biomol Struct. 2007; 36:213-31.
Michael et al., Combined imaging and chemical sensing of fertilization-induced acid release from single sea urchin eggs. Anal Biochem. Sep. 10 1999; 273(2):168-78.
Michael et al., Randomly ordered addressable high-density optical sensor arrays. Anal Chem. Apr. 1, 1998; 70(7):1242-8.
Monk et al., Fabrication of gold microtubes and microwires in high aspect ratio capillary arrays. J Am Chem Soc. Sep. 22, 2004; 126(37):11416-7.
Monk et al., Optical fiber-based biosensors. Anal Bioanal Chem. Aug. 2004; 379(7-8):931-45. Epub Jun. 23, 2004.
Monk et al., Progress toward the dermination of $Sr^{2+}$ in highly basic solutions using imagining optical fiber sensor arrays. J. Mater. Chem. 2005; 15:4361-4366.
Morrison et al., Nanoliter high throughput quantitative PCR. Nucleic Acids Res. 2006;34(18):e123. Epub Sep. 25, 2006.
Munkholm et al., Polymer modification of fiber optic chemical sensors as a method of enhancing fluroescence signal for pH measurement. Anal Chem. 1986; 58:1427-1430.
Nagai et al., High-throughput PCR in silicon based microchamber array. Biosens Bioelectron. Dec. 2001; 16(9-12):1015-9.
Nalefski et al., Single-molecule detection for femtomolar quantification of proteins in heterogeneous immunoassays. Clin Chem. Nov. 2006; 52(11):2172-5.
Nam et al., Nanoparticle-based bio-bar codes for the ultrasensitive detection of proteins. Science. Sep. 26, 2003;301(5641):1884-6.
Niemeyer et al., Combination of DNA-directed immobilization and immuno-PCR: very sensitive antigen detection by means of self-assembled DNA-protein conjugates. Nucleic Acids Res. Aug. 15, 2003; 31(16):e90, 7 pages.
Panova et al., In situ fluorescence imaging of localized corrosion with a pH-sensitive imaging fiber. Anal Chem. Apr. 15, 1997; 69(8):1635-41.
Pantano et al., Analytical applications of optical imaging fibers. Anal Chem. Aug. 1, 1995; 67(15):481A-487A.
Pantano et al., Ordered nanowell arrays. Chemistry of Materials. 1996;8: 2832-2835.
Pantano et al., Toward a near-field optical array. Rev. Sci. Instrum. 1997; 68(3) 1357-1359.
Peterson et al., Fiber optic pH probe for physiological use. Anal Chem. May 1980; 52(6):864-9.
Qiu et al., Fluorescence single-molecule counting assays for high-sensitivity detection of cytokines and chemokines. Clin Chem. Nov. 2007; 53(11):2010-2.
Randle et al., Integrating molecular detection and response to create self-signalling antibodies. Biochem Biophys Res Commun. Nov. 12, 2004; 324(2):504-10.

(56) References Cited

OTHER PUBLICATIONS

Rissin et al., Attomolar detection of proteins in serum using single molecule enzyme-linked immunosorbent assays. Quanterix Corporation. Oak Ridge Conference, San Jose, CA. Poster. 2010. 1 page.

Rissin et al., Digital concentration readout of single enzyme molecules using femtoliter arrays and Poisson statistics. Nano Lett. Mar. 2006; 6(3):520-3.

Rissin et al., Digital readout of target binding with attomole detection limits via enzyme amplification in femtoliter arrays. J Am Chem Soc. May 17, 2006; 128(19):6286-7.

Rissin et al., Distinct and long-lived activity states of single enzyme molecules. J Am Chem Soc. Apr. 16, 2008; 130(15):5349-53. Epub Mar. 5, 2008.

Rissin et al., Duplexed sandwich immunoassays on a fiber-optic microarray. Anal Chim Acta. Mar. 30, 2006; 564(1):34-9. Epub Nov. 11, 2005.

Rissin et al., Single-molecule enzyme-linked immunosorbent assay detects serum proteins at subfemtomolar concentrations. Nat Biotechnol. Jun. 2010; 28(6):595-9 and supplemental pages. Epub May 23, 2010.

Rissin et al., Simultaneous detection of single molecules and singulated ensembles of molecules enables immunoassays with broad dynamic range. Anal Chem. Mar. 15, 2011;83(6):2279-85. Epub Feb. 23, 2011.

Roeffaers et al., Single-molecule fluorescence spectroscopy in (bio)catalysis. Proc Natl Acad Sci U S A. Jul. 31, 2007; 104(31):12603-9. Epub Jul. 30, 2007.

Rondelez et al., Highly coupled ATP synthesis by F1-ATPase single molecules. Nature. Feb. 17, 2005; 433(7027):773-7.

Rondelez et al., Microfabricated arrays of femtoliter chambers allow single molecule enzymology. Nat Biotechnol. Mar. 2005; 23(3):361-5. Epub Feb. 20, 2005.

Rotman, Measurement of activity of single molecules of beta-D-galactosidase. Proc Natl Acad Sci U S A. Dec. 15, 1961; 47:1981-91.

Schauer et al., A cross-reactive, class-selective enzymatic array assay. J Am Chem Soc. Sep. 26, 2001; 123(38):9443-4.

Schmidinger, et al , Inhibitor and protein microarrays for activity-based recognition of lipolytic enzymes. Chembiochem. Mar. 2006; 7(3):527-34.

Schweitzer et al., Inaugural article: immunoassays with rolling circle DNA amplification: a versatile platform for ultrasensitive antigen detection. Proc Natl Acad Sci U S A. Aug. 29, 2000; 97(18):10113-9.

Seydack, Nanoparticle labels in immunosensing using optical detection methods. Biosens Bioelectron. Jun. 15, 2005; 20(12):2454-69. Epub Dec. 16, 2004.

Shen et al. High-throughput SNP genotyping on universal bead arrays. Mutat Res. Jun. 3, 2005;573(1-2):70-82.

Shephard et al., Array-based binary analysis for bacterial typing. Anal Chem. Jan. 1, 2005; 77(1):319-26.

Song et al., Detecting biological warfare agents. Emerg Infect Dis. Oct. 2005; 11(10):1629-32.

Song et al., Fiber-optic microsphere-based arrays for multiplexed biological warfare agent detection. Anal Chem. Feb. 15, 2006; 78(4):1023-33.

Soukka et al., Supersensitive time-resolved immunofluorometric assay of free prostate-specific antigen with nanoparticle label technology. Clin Chem. 2001; 47(7):1269-78.

Stamou et al., Self-assembled microarrays of attoliter molecular vessels. Angew Chem Int Ed Engl. Nov. 24, 2003; 42(45):5580-3.

Steemers et al., Multi- analyte sensing: from site-selective deposition to randomly ordered addressable optical sensors. Microchimica Acta. 1999; 131:99-105.

Steemers et al., Screening unlabeled DNA targets with randomly ordered fiber-optic gene arrays. Nat Biotechnol. Jan. 2000; 18(1):91-4.

Stitzel et al., Array-to-array transfer of an artificial nose classifier. Anal Chem. Nov. 1, 2001; 73(21):5266-71. Epub Sep. 28, 2001.

Subbaraman, Detecting single cancer molecules. Technol Rev. Jun. 3, 2010. Last accessed at http://www.technologyreview.com/biomedicine/25462/ on Jan. 31, 2012. 1 page.

Sykes et al., Quantitation of targets for PCR by use of limiting dilution. Biotechniques. 1992;13(3):444-9.

Szunerits et al., "Aluminum Surface Corrosion and the Mechanism of Inhibitors Using pH and Metal Ion Selective Imaging Fiber Bundles," *Analytical Chemistry*, 2002, 74(4), 886-894.

Szunerits et al., "Fabrication of an Optoelectrochemical Microring Array," *Analytical Chemistry*, 2002, 74(7), 1718-1723.

Szunerits et al., Spatially resolved electrochemiluminescence on an array of electrode tips. Anal Chem. Sep. 1, 2003; 75(17):4382-8.

Szunerits et al., The use of optical fiber bundles combined with electrochemistry for chemical imaging. Chemphyschem. Feb. 17, 2003; 4(2):186-92. Epub Feb. 7, 2003.

Szurdoki et al., A duplexed microsphere-based fluorescent immunoassay. Anal Biochem. Apr. 15, 2001; 291(2):219-28.

Tam et al., An imaging fiber-based optical tweezer array for microparticle array assembly. Applied Physics Letters. 2004; 84(21):4289-4291.

Tam et al., Fabrication and optical characterization of imaging fiber-based nanoarrays. Tabula. Sep. 15, 2005; 67(3):498-502. Epub Jul. 27, 2005.

Tam et al., Parallel microparticle manipulation using an imaging fiber bundle-based optical tweezer array and a digital micromirror device. Applied Physics Letters. 2006; 89:194101/1-194101/3.

Tan et al., Monitoring the reactions of single enzyme molecules and single metal ions. Anal. Chem. 1997; 69:4242-4248.

Taylor et al., Application of high-density optical microwell arrays in a live-cell biosensing system. Anal Biochem. Feb. 15, 2000; 278(2):132-42.

Tessler et al., Protein quantification in complex mixtures by solid phase single-molecule counting. Anal Chem. Sep. 1, 2009; 81(17):7141-8.

Thaxton et al., Nanoparticle-based bio-barcode assay redefines "undetectable" PSA and biochemical recurrence after radical prostatectomy. Proc Natl Acad Sci U S A. Nov. 3, 2009;106(44):18437-42. Epub Oct. 19, 2009.

Timmerman, Quanterix CEO sets sight on early detection of cancer, neurological diseases in the blood. Xconomy. Jan. 19, 2010. Last accessed at http://www.xconomy.com/boston/2010/01/19/quanterix-ceo-sets-sight-on-early-detection-of-cancer-neurological-diseases-in-the-blood/ on Jan. 31, 2012. 4 pages.

Todd et al., Ultrasensitive flow-based immunoassays using single-molecule counting. Clin Chem. Nov. 2007; 53(11):1990-5. Epub Sep. 21, 2007.

Tromberg et al., Development of antibody-based fiber-optic sensors for detection of a benzo[a]pyrene metabolite. Anal Chem. Sep. 15, 1988; 60(18):1901-8.

Ueberfeld et al., Reversible ratiometric probe for quantitative DNA measurements. Anal Chem. Feb. 15, 2004; 76(4):947-52. Epub Jan. 20, 2004.

Vo-Dinh et al., Phase-resolved fiber-optics fluoroimmunosensor. Applied Spectroscopy. 1990; 44(1):128-132.

Vogelstein et al., Digital PCR. Proc Natl Acad Sci U S A. Aug. 3, 1999;96(16):9236-41.

Walt et al., Biosensing with live cells using a high-density optical fiber array. Radiation Research. 2001; 156(4):442.

Walt et al., Microsensor arrays for saliva diagnostics. Ann N Y Acad Sci. Mar. 2007; 1098:389-400.

Walt et al., Optical sensor arrays for odor recognition. *Biosens Bioelectron.* Sep. 15, 1998; 13(6):697-9.

Walt et al., Ultrasensitive detection of proteins using single molecule arrays (SiMoA). Presented Mar. 1, 2010. Pittcon. Abstract and PowerPoint presentation. 32 pages.

Walt, An array of solutions, fiber arrays contribute to studies of individual cellular behavior and response. SPIE's oemagazine. 2005; 19-21.

Walt, Fiber optic array biosensors. Biotechniques. Nov. 2006; 41(5):529, 531, 533, 535 passim.

Walt, Fiber optic imaging sensors. Accounts of Chemical Research. 1998; 31:267-278.

Walt, Imaging optical sensor arrays. *Curr Opin Chem Biol.* Oct. 2002; 6(5):689-95.

Walt, Techview: molecular biology. Bead-based fiber-optic arrays. *Science.* Jan. 21, 2000; 287(5452):451-2.

(56) References Cited

OTHER PUBLICATIONS

Wang et al., Quantification of protein based on single-molecule counting by total internal reflection flourescence microscopy with adsorption equilibrium. *Anal Chim Acta*. May 2, 2007; 590(1):104-9. Epub Mar. 15, 2007.

Warren et al., Transcription factor profiling in individual hematopoietic progenitors by digital RT-PCR. Proc Natl Acad Sci U S A. Nov. 21, 2006;103(47):17807-12. Epub Nov. 10, 2006.

Whitaker et al., Fiber-based single cell analysis of reporter gene expression in yeast two-hybrid systems. *Anal Biochem*. Jan. 1, 2007; 360(1):63-74. Epub Oct. 30, 2006.

Whitaker et al., Multianalyte single-cell analysis with multiple cell lines using a fiber-optic array. Anal Chem. Dec. 1, 2007; 79(23):9045-53. Epub Nov. 1, 2007.

White et al., An olfactory neuronal network for vapor recognition in an artificial nose. *Biol Cybern*. Apr. 1998; 78(4):245-51.

White et al., Rapid analyte recognition in a device based on optical sensors and the olfactory system. Analytical Chemistry. 1996; 68(13):2191-2202.

Wu et al., Development and preliminary clinical validation of a high sensitivity assay for cardiac troponin using a capillary flow (single molecule) fluorescence detector. *Clin Chem*. Nov. 2006; 52(11):2157-9.

Xie et al., Optical studies of a single molecules at room temperature. *Annu Rev Phys Chem*. 1998; 49:441-80.

Xie et al., Single gold nanoparticles counter: an ultrasensitive detection platform for one-step homogeneous immunoassays and DNA hybridization assays. J Am Chem Soc. Sep. 9, 2009;131(35):12763-70.

Xue et al., Difference in the chemical reactivity of individual molecules of an enzyme. *Nature*. Feb. 23, 1995; 373(6516):681-3.

Young et al., Integrating high-content screening and ligand-target prediction to identify mechanism of action. Nat Chem Biol. Jan. 2008; 4(1):59-68. Epub Dec. 9, 2007.

\* cited by examiner

ULTRA-SENSITIVE DETECTION OF MOLECULES ON SINGLE MOLECULE ARRAYS

RELATED APPLICATIONS

This application is a continuation of U.S. patent application Ser. No. 12/236,486, filed Sep. 23, 2008 and issued as U.S. Pat. No. 8,222,047, entitled "ULTRA-SENSITIVE DETECTION OF MOLECULES ON SINGLE MOLECULE ARRAYS," which is incorporated herein by reference in its entirety for all purposes.

FIELD OF THE INVENTION

The present invention relates to systems and methods for detecting analyte molecules or particles in a fluid sample and in some cases, determining a measure of the concentration of the molecules or particles in the fluid sample.

BACKGROUND OF THE INVENTION

Methods and systems that are able to quickly and accurately detect and, in certain cases, quantify a target analyte molecule or particle in a sample are the cornerstones of modern analytical measurements. Such systems and/or methods are employed in many areas such as academic and industrial research, environmental assessment, food safety, medical diagnosis, and detection of chemical, biological and/or radiological warfare agents. Advantageous features of such techniques may include specificity, speed, and sensitivity.

Most current techniques for quantifying low levels of analyte molecules in a sample use amplification procedures to increase the number of reporter molecules in order to be able to provide a measurable signal. For example, these known processes include enzyme-linked immunosorbent assays (ELISA) for amplifying the signal in antibody-based assays, as well as the polymerase chain reaction (PCR) for amplifying target DNA strands in DNA-based assays. A more sensitive but indirect protein target amplification technique, called immunoPCR (see Sano, T.; Smith, C. L.; Cantor, C. R. *Science* 1992, 258, 120-122), makes use of oligonucleotide markers, which can subsequently be amplified using PCR and detected using a DNA hybridization assay (see Nam, J. M.; Thaxton, C. S.; Mirkin, C. A. *Science* 2003; 301, 1884-1886; Niemeyer, C. M.; Adler, M.; Pignataro, B.; Lenhert, S.; Gao, S.; Chi, L. F.; Fuchs, H.; Blohm, D. *Nucleic Acids Research* 1999, 27, 4553-4561; and Zhou, H.; Fisher, R. J.; Papas, T. S. *Nucleic Acids Research* 1993, 21, 6038-6039). While the immuno-PCR method permits ultra low-level protein detection, it is a complex assay procedure, and can be prone to false-positive signal generation (see Niemeyer, C. M.; Adler, M.; Wacker, R. *Trends in Biotechnology* 2005, 23, 208-216).

One disadvantage of typical known methods and/or systems for accurately detecting and, optionally, quantifying low concentrations of a particular analyte in solution is that they are based on ensemble responses in which many analyte molecules give rise to the measured signal. Most detection schemes require that a large number of molecules are present in the ensemble for the aggregate signal to be above the detection threshold. This disadvantage limits the sensitivity of most detection techniques and the dynamic range (i.e., the range of concentrations that can be detected). Many of the known methods and techniques are further plagued with problems of non-specific binding, which is the binding of analyte molecules/particles to be detected or reporter species non-specifically to sites other than those expected. This leads to an increase in the background signal, and therefore limits the lowest concentration that may be accurately or reproducibly detected.

Accordingly, improved methods for detecting and, optionally, quantifying analyte molecules or particles, especially in samples where such molecules or particles are present at very low concentration are needed.

SUMMARY OF THE INVENTION

The present invention relates to systems and methods for detecting analyte molecules or particles in a fluid sample and in some cases, determining a measure of the concentration of the molecules or particles in the fluid sample. The subject matter of the present invention involves, in some cases, interrelated products, alternative solutions to a particular problem, and/or a plurality of different uses of one or more systems and/or articles.

In one aspect, the invention is directed towards a method. According to one set of embodiments, a method of detecting analyte molecules or particles in a fluid sample, comprises exposing a substrate comprising a plurality of capture components to a sample comprising a plurality of analyte molecules or particles, so that analyte molecules or particles associate with capture components to form a plurality of complexes, each complex being immobilized with respect to the substrate and comprising at least one capture component and at least one analyte molecule or particle, dissociating at least a portion of each complex to form a plurality of dissociated species, which are not immobilized with respect to the substrate, partitioning the plurality of dissociated species across a plurality of reaction vessels, and determining the presence or absence of a dissociated species in at least one reaction vessel.

In one aspect, the invention is directed towards a system. According to one set of embodiments, a system for detecting analyte molecules or particles in a fluid sample, comprises a first substrate comprising a plurality of capture components able to become specifically immobilized with respect to a plurality of analyte molecules or particles of a sample, such that the analyte molecules or particles associate with capture components to form a plurality of complexes, wherein the complexes are susceptible to being dissociated from the first substrate by a dissociating agent to form a plurality of dissociated species, and a second substrate comprising an array comprising a plurality of reaction vessels, the reaction vessels being configured to receive and contain dissociated species therein.

According to another set of embodiments, a method for determining a measure of the concentration of analyte molecules or particles in a fluid sample, comprises capturing a plurality of analyte molecules or particles on a first substrate, releasing a plurality of molecules or particles from the first substrate, detecting molecules or particles released from the first substrate on or within a second substrate comprising a plurality of reaction vessels, and determining a measure of the concentration of the analyte molecules or particles in the fluid sample based on the detection of molecules or particles released from the first substrate on or within the second substrate.

According to another set of embodiments, a method for determining a measure of the concentration of the analyte molecules or particles in a fluid sample, comprises capturing a plurality of analyte molecules or particles on a first substrate, releasing a plurality of molecules or particles from the first substrate, detecting molecules or particles released from the first substrate on or within a second substrate, and determining a measure of the concentration of the analyte molecules or particles in the fluid sample based on the detection of molecules or particles released from the first substrate, wherein the true concentration of the analyte molecules or particles in the fluid sample is less than about $50 \times 10^{-15}$ molar, and wherein the measure of the concentration determined in the determining act differs from the true concentration by no greater than 10%.

According to yet another set of embodiments, a method for determining a measure of the concentration of analyte molecules or particles in a fluid sample, comprises capturing a plurality of analyte molecules or particles on a first substrate, releasing a plurality of molecules or particles from the first substrate, immobilizing at least one particle comprising a binding partner for the molecule or particle released from the first substrate to each of at least a fraction of the plurality of molecules or particles released from the first substrate to form a plurality of complexes, detecting the plurality of complexes formed in the immobilizing act, and determining a measure of the concentration of the analyte molecules or particles in the fluid sample based on the detection of the complexes.

In some embodiments, a method for determining a measure of the concentration of analyte molecules or particles in a fluid sample, comprises, capturing a plurality of analyte molecules or particles on a first substrate by immobilizing the plurality of analyte molecules or particles on the first substrate, releasing a plurality of immobilized molecules or particles from the first substrate, wherein the number of molecules or particles released is related to the number of analyte molecules or particles captured, detecting molecules or particles released from the first substrate on or within a second substrate, wherein at least a fraction of the molecules or particles released from the first substrate become immobilized with respect to the second substrate, and wherein the number of molecules or particles detected on or within the second substrate is no greater than the number of molecules or particles which are released from the first substrate, and determining a measure of the concentration of the analyte molecules or particles in the fluid sample based on the detection of molecules or particles released from the first substrate.

In another set of embodiments, a method for determining a measure of the concentration of analyte molecules or particles in a fluid sample, comprises capturing a plurality of analyte molecules or particles on a first substrate by immobilizing the plurality of analyte molecules or particles on the first substrate, releasing a plurality of immobilized molecules or particles from the first substrate, wherein the number of molecules or particles released is related to the number of analyte molecules or particles captured, immobilizing at least one first binding ligand with respect to each of at least a fraction of the plurality of analyte molecules or particles or to each of at least a fraction of the plurality of molecules or particles released from the first substrate, capturing at least a fraction of the plurality of molecules or particles released from the first substrate on or within a second substrate, exposing the second substrate to a plurality of precursor labeling agent molecules, wherein the plurality of precursor labeling agent molecules are converted to a plurality of labeling agent molecules upon exposure to first binding ligands, and determining a measure of the concentration of the analyte molecules or particles in the fluid sample based on the detection of the labeling agent molecules.

In still yet another set of embodiments, a method of detecting analyte molecules or particles in a fluid sample, comprises exposing a substrate comprising a plurality of capture components to a sample comprising a plurality of analyte molecules or particles, so that analyte molecules or particles associate with capture components to form a plurality of complexes, each complex being immobilized with respect to the substrate and comprising at least one capture component and at least one analyte molecule or particle, dissociating at least a portion of each complex to form a plurality of dissociated species, which are not immobilized with respect to the substrate, and detecting at least some of the plurality of the dissociated species substantially simultaneously, wherein substantially all of the detected dissociated species are spatially separated with respect to the other detected dissociated species during detection, such that detection is able to resolve individual dissociated species of the plurality of dissociated species.

Figure 1:
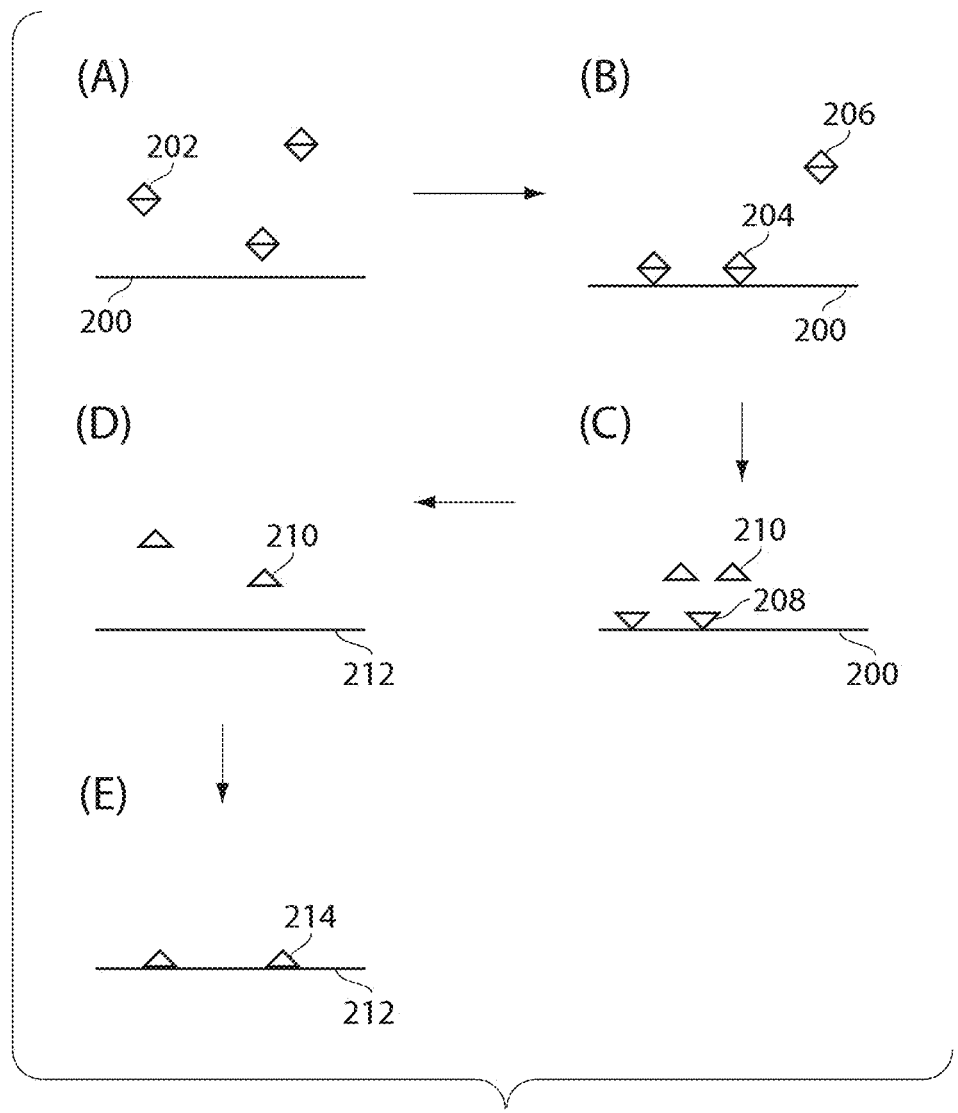
FIG. 1 is a schematic flow diagram depicting one embodiment of steps (A-E) for performing one method of the present invention.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention relates to systems and methods for the detection and/or quantification of analyte molecules, particles (such as, for example, cells, cell organelles and other biological or non-biological particulates) and the like, in a sample. The subject matter of the present invention involves, in some cases, interrelated products, alternative solutions to a particular problem, and/or a plurality of different uses of one or more systems and/or articles. It should be understood, that while much of the discussion below is directed to analyte molecules, this is by way of example only, and other materials may be detected and/or quantified, for example, analyte particles. Particular examples of analytes will be discussed more below.

The systems and methods of the present invention in certain instances may help reduce the negative effects of non-specific binding on detection sensitivity when compared to typical conventional systems and methods for performing similar assays. Non-specific binding is the binding or association in a non-specific fashion of one component of an assay with another component of the assay with which it is not desirable that it interact. For example, association, binding, or immobilization of a binding ligand with the material forming a reaction vessel wall as opposed to with an analyte molecule or particle to which it has binding specificity. Non-specific binding may lead to false positive signals. Non-specific binding may not only affect the accuracy of the assay measurement, but may also limit the lowest level of detection. Therefore, methods and/or systems of the present invention, which in certain embodiments involve improvements in the level of non-specific binding, may allow for the detection and/or quantification of analyte molecules in a sample at a lower detection limit as compared to typical current technologies. In addition, certain embodiments of the methods and/or systems of the present invention may also allow for the detection and/or quantification of analyte molecules in certain samples that have previously been undetected and/or unquantifiable in such samples because of the very low concentration in which they are present.

"Capture-and-release" systems and methods of certain embodiments of present invention which utilize a first substrate and a second substrate also can provide additional benefits as compared to a basic capture assay that employs only a single substrate. For example, the first substrate may be configured to provide a greater surface area, greater volumetric capacity, and/or increased number/density of capture components as compared to an assay employing only one substrate. That is, the surface area and/or volumetric capacity of the first substrate may be greater than the substrate used in an assay employing only one substrate such that the analyte molecules may be more effectively, rapidly and/or thoroughly immobilized with respect to the first substrate versus immobilization of the target analyte in the sample directly on a single substrate where detection also occurs. The required exposure time of the substrate to the analyte molecules may also be decreased in some cases using an assay of the present invention due to an increase in surface area and/or volumetric capacity of the substrate (e.g., by increasing binding kinetics).

In certain embodiments, the methods for detection and/or quantifying analyte molecules in a sample comprise a capture-and-release protocol, wherein the analyte molecules are captured on a substrate and form a plurality of complexes associated with the substrate. The substrate may be optionally exposed to additional reaction components such as at least one binding ligand, as discussed more below. At least a portion of the plurality of complexes may be dissociated or otherwise released from the substrate, for example, by exposing the complexes to a dissociating agent (e.g., a reducing agent) and/or by cleaving a cleavable linkage (e.g., a disulfide linkage or a photocleavable linkage) comprising at least a portion of the complexes dissociated. In some cases, a dissociable/dissociated complex may comprise an enzymatic component, which in certain embodiments may be used to facilitate dissociation and/or detection of the dissociated complex. At least a portion of the plurality of dissociated complexes may be detected and may be used to determine the presence of and/or quantify the analyte molecules in the sample. The dissociated complexes may be detected either directly or indirectly, as explained in more detail below.

An assay method according to some embodiments of the present invention is illustrated in FIG. 1. A first substrate 200 is exposed to a sample comprising a plurality of analyte molecules 202 (step (A)). At least a portion of the analyte molecules associate with the first substrate 200 to form a plurality of immobilized complexes 204, however, some analyte molecules 206 may not associate with the first substrate (step (B)). At least a portion of at least some of the immobilized complexes are dissociated from the substrate to form a plurality of dissociated species 210 (step (C)). The dissociated species, in the present example are not immobilized with respect to the first substrate. In some cases, at least a portion of the immobilized complexes 208 remain associated with the first substrate. The plurality of dissociated species 210 are exposed to a second substrate 212 (step (D)), and at least some of the dissociated species associate with the second substrate 212 (step (E)). The plurality of dissociated species that associate with the second substrate can then be detected and/or quantified and, thereby, the analyte molecules in the sample can be detected and/or quantified.

Figure 2:
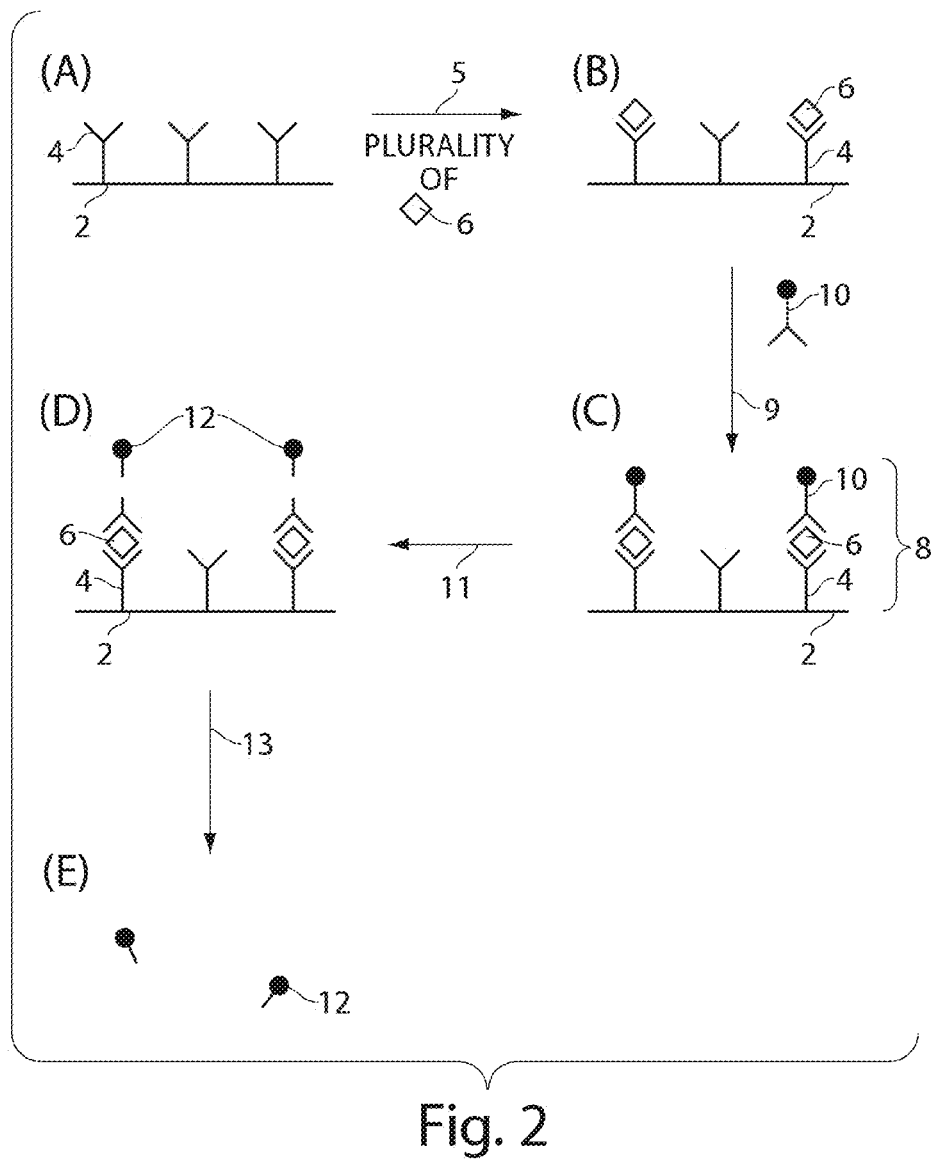
FIG. 2 is a schematic flow diagram depicting a sequence of steps (A-E) of one embodiment of one method of the present invention.

Additional components and/or method steps may be utilized in combination with the above described method. For example, in some cases, at least one of the first substrate and/or second substrate may comprise a plurality of capture components with which the analyte molecules and/or dissociated species may associate. As another example, in certain embodiments, at least a portion of at least some of the immobilized complexes dissociate from the substrate to form a plurality of dissociated species, wherein, depending on the particular design of the assay as explained below, the dissociated species may or may not comprise any portion of an analyte molecule and/or capture component. For example, the substrate may be additionally exposed to a plurality of at least one type of binding ligand such that at least one binding ligand associates with at least a portion of the plurality of complexes, either before, after or essentially simultaneously with the immobilization of the complex on the substrate. Such an embodiment is illustrated in FIG. 2. Substrate 2 comprising a plurality of capture components 4 (step (A)) is exposed to plurality of analyte molecules 6, as indicated by arrow 5. Analyte molecules 6 associate with one of the plurality of capture components 4 (step (B)). The substrate is then exposed to an optional binding ligand 10, as indicated by arrow 9, such that a binding ligand associates with at least a portion of the analyte molecules associated with the substrate and form a plurality of immobilized complexes 8 (step (C)). At least a portion of some of the plurality of immobilized complexes may be dissociated to form a plurality of dissociated species 12, as indicated by arrow 11 (step (D)). The dissociated species may or may not comprise a portion of an analyte molecule, a capture component and/or a binding ligand. In the depicted example, a portion 12 of each of the binding ligands were dissociated. At least a portion of the plurality of dissociated species may be quantified and/or detected, as indicated by arrow 13 (step (E)).

In certain embodiments, the invention provides methods for detecting and/or quantifying a plurality of dissociated species. The method may comprise partitioning the plurality of dissociated species across a plurality of reaction vessels, such that at least some of the reaction vessels contain at least one or, in certain cases, one dissociated species and at least some of the reaction vessels contain no dissociated species. In some cases, the plurality of dissociated species may be partitioned across a plurality of reaction vessels, such that a statistically significant fraction of the reaction vessels contains at least one or, in certain cases, one dissociated species and a statistically significant fraction of reaction vessels contain no dissociated species. The presence or absence of a dissociated species in a reaction vessel may be determined to determine the number of reaction vessels which contain zero, one, or multiple dissociated species. The number of reaction vessels containing various quantities of dissociated species thusly determined may then be used to quantify the dissociated species, and additionally may be used to determine a measure of the concentration of the analyte molecules in the original fluid sample.

The foregoing methods can be performed using a number of different assay formats, different reaction conditions, and/or detection systems in different embodiments of the invention. In certain embodiments, the reaction vessels may be adapted to capture the dissociated species of interest. Depending on the assay format, the reaction vessel may comprise a microwell and a dissociated species capture component (also referred to as a detection capture component) for capturing the dissociated species, as discussed more below.

In certain embodiments, the present inventions involve exposing a substrate comprising a plurality of capture components to a plurality of analyte molecules. A "capture component", as used herein, is any molecule, other chemical/biological entity or solid support modification disposed upon a solid support that can be used to specifically attach, bind or otherwise capture a target molecule or particle (e.g., an analyte molecule or dissociated species), such that the target molecule/particle becomes immobilized with respect to the capture component and solid substrate. As used herein, "immobilized" means captured, attached, bound, or affixed so as to prevent dissociation or loss of the target molecule/particle, but does not require absolute immobility with respect to either the capture component or the solid substrate. Capture components which are useful or potentially useful for practicing certain aspects and embodiments of the invention are discussed in more detail below. At least some of the analyte molecules, upon exposure to the substrate comprising a plurality of capture components, can become immobilized with respect to a capture component, thereby forming a plurality of immobilized complexes. For example, in certain embodiments, substantially all of the plurality of analyte molecules may become immobilized with respect to capture components such that essentially each of the plurality of immobilized complexes comprises a capture component and an analyte molecule.

The substrate on or in which the plurality of immobilized complexes is immobilized may comprise a microtiter plate, a plurality of beads (e.g., magnetic beads), or any other substrate that, in certain embodiments, comprises a plurality of capture components, as discussed more below In some embodiments, the substrate comprising the immobilized complexes may be exposed to at least one additional reaction component, for example, at least a first type of binding ligand. A "binding ligand," as used herein, is any molecule, particle, or the like which specifically binds to or otherwise specifically associates with an analyte molecule, immobilized complex and/or dissociated species or another molecule or particle bound to or otherwise associated with the analyte molecule, immobilized complex and/or dissociated species (e.g., another binding ligand). In certain embodiments, the binding ligand can convert a precursor labeling agent molecule to a labeling agent, as discussed more below. More than one type of binding ligand may be employed in any given assay method, for example, a first type of binding ligand and a second type of binding ligand. In one example, the first binding ligand is able to associate with an analyte molecule and the second binding ligand is able to associate with the first binding ligand. When the substrate is exposed to a plurality of types of binding ligand, at least some of the plurality of immobilized complexes may additionally comprise, in some cases, at least one of each type of binding ligand. In certain embodiments, the binding ligand can be exposed to the substrate after capture of the analyte molecule so that the binding ligand binds to the immobilized complex. In other embodiments, the binding ligand may become associated with the analyte molecule to form a complex followed by capture of the complex by the substrate to form the immobilized complex. In yet other embodiments, the binding ligand may bind to the dissociated species formed upon release of the immobilized complex, or portion thereof, from the substrate.

In some embodiments, a plurality of dissociated species may be formed by dissociating at least a portion of at least some of the plurality of immobilized complexes. In certain embodiments, a plurality of molecules or particles may be released from the substrate. Any or each of the plurality of dissociated species (e.g., molecules or particles released from a substrate) may comprise any portion of an immobilized complex. For example, the dissociated species may comprise (i) at least a portion of a binding ligand, (ii) at least a portion of a binding ligand and at least a portion of the analyte molecule, (iii) at least a portion of a binding ligand, at least a portion of an analyte molecule and at least a portion of a capture component, or (iv) essentially all of the immobilized complex.

Figure 3:
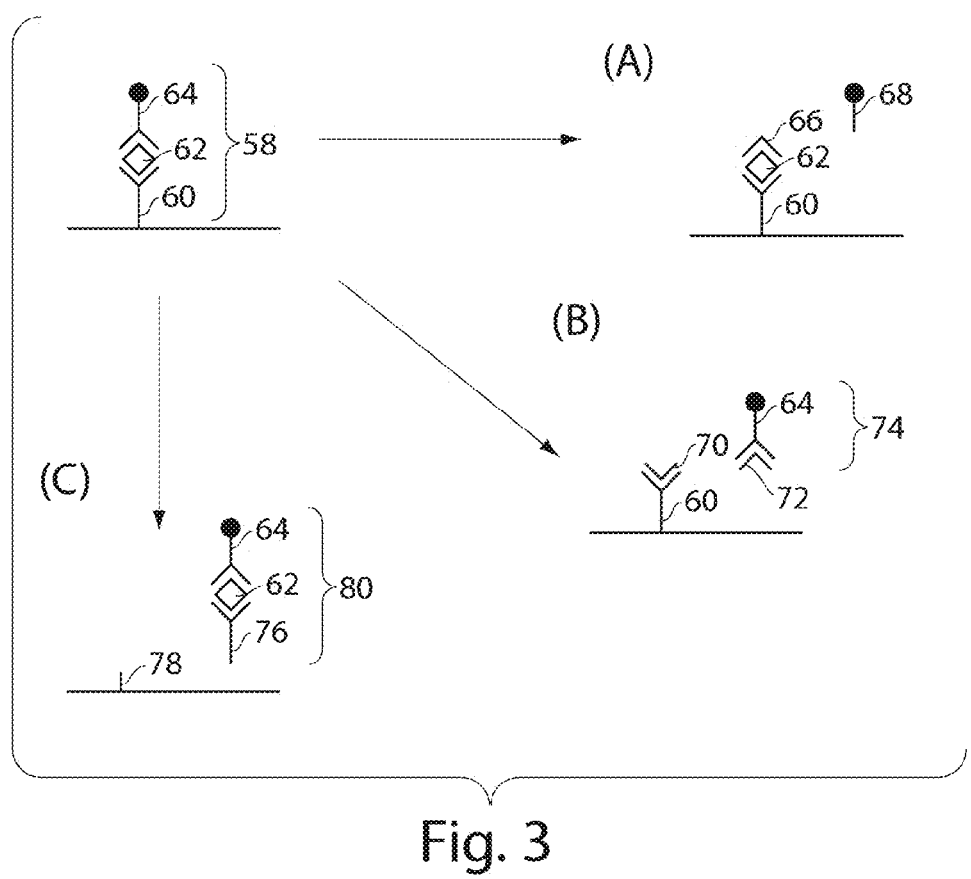
FIG. 3 is a schematic flow diagram depicting embodiments (A-C) of how an immobilized complex may dissociate from a substrate according to certain embodiments.

Non-limiting examples of how a dissociated species may be released from the substrate are depicted in FIG. 3. In scheme (A), a portion 68 of a binding ligand 64 is dissociated from immobilized complex 58, which comprises capture component 60, analyte molecule 62, and binding ligand 64. The remainder 66 of binding ligand 64 remains associated with analyte molecule 62. Scheme (B) shows the formation of a dissociated species 74 comprising a portion 72 of the analyte molecule 62 and binding ligand 64. The remainder 70 of the analyte molecule 62 remains associated with capture component 60. Scheme (C) shows the formation of a dissociated species 80 comprising binding ligand 64, analyte molecule 60, and a portion 76 of capture component 60, while the remainder 78 of capture component 60 remains attached to the substrate. As would be understood by those skilled in the art given the revelation of this disclosure, many other possibilities are potentially feasible.

The plurality of immobilized complexes may be dissociated in certain embodiments by exposure to a dissociating agent. A "dissociating agent," as used herein, is any agent that causes at least a portion of an immobilized complex to dissociate, thereby forming a dissociated species. For example, the dissociating agent may be a chemical dissociating agent, electromagnetic radiation, a change in pH, a change in temperature, a change in ionic strength, or the like. In a particular embodiment, the dissociating agent is a chemical dissociating agent that interacts with a portion of an immobilized complex, thereby causing a portion of the immobilized complex to dissociate. One specific example of a chemical dissociating agent useful for practicing certain embodiments of the invention is beta-mercaptoethanol. Dissociating agents are further discussed in more detail below. In some embodiments, as will be discussed more below, the dissociated species may comprise a detectable component or a reactive component (e.g., an enzymatic component) that is able to interact with a precursor labeling agent molecule (e.g., an enzymatic substrate) to produce a labeling agent.

In some embodiments, the immobilized complex comprises a cleavable linkage. A "cleavable linkage," as used herein, is linkage that is able to be readily (i.e. under conditions not detrimental to the integrity of other portions of the immobilized complex) and selectively cleaved upon exposure to a dissociating agent. The cleavable linkage upon cleavage by exposure to a dissociating agent forms the dissociated species. One specific example of a cleavable linkage, which can be cleaved using beta-mercaptoethanol, is a disulfide linkage. Cleavable linkages and corresponding dissociating agents that can cause the cleavable linkage to cleave are discussed in more detail below.

Figure 4:
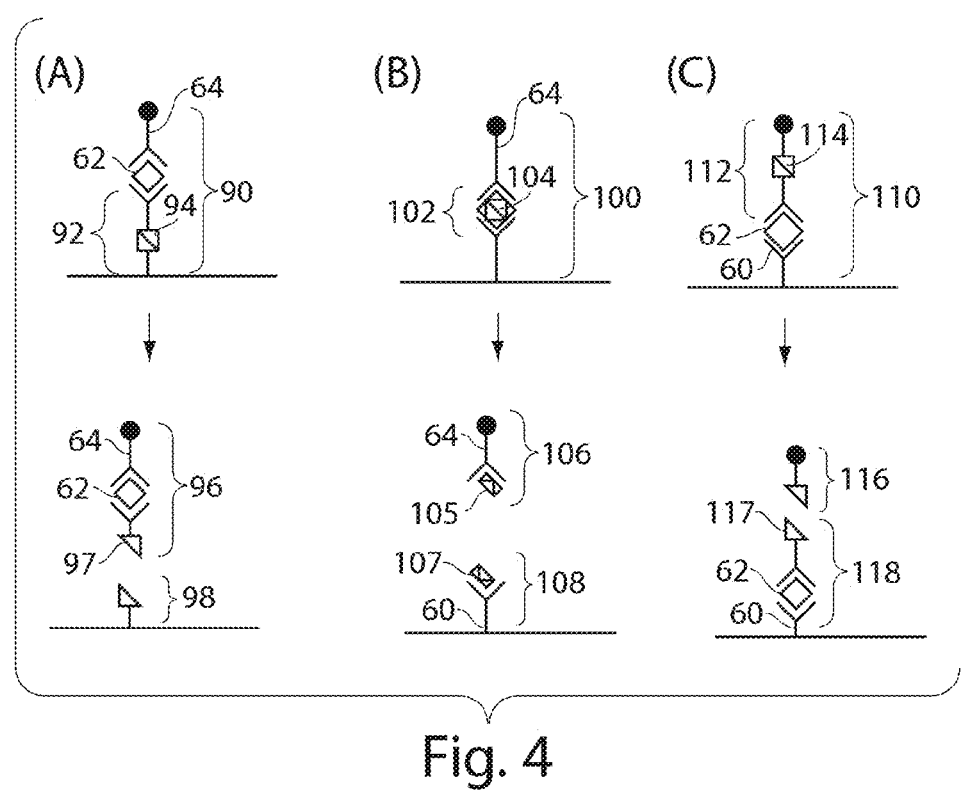
FIG. 4 is a schematic flow diagram illustrating immobilized complexes comprising cleavable linkages and cleaving of the cleavable linkages, according to various embodiments (A-C)

A cleavable linkage may be present in any portion of an immobilized complex. For example, FIG. 4, panel (A), depicts an immobilized complex 90 wherein the capture component 92 comprises a cleavable linkage 94. Cleaving the cleavable linkage forms the dissociated species 96 comprising the binding ligand 64, the analyte molecule 62 and a portion 97 of the capture component, wherein the complementary portion 98 of the capture component remains attached to the substrate. FIG. 4, panel (B), depicts an immobilized complex 100 wherein analyte molecule 102 comprises a cleavable linkage. Cleaving of the cleavable linkage forms the dissociated species 106 comprising the binding ligand 64 and a portion 105 of the analyte molecule, wherein the complementary portion 107 of the analyte molecule and the capture component 60 remain form a portion 108, which remains immobilized with respect to the substrate. FIG. 4, panel (C), depicts immobilized complex 110 wherein binding ligand 112 comprises cleavable linkage 114. Cleaving the cleavable linkage forms the dissociated species 116 comprising a portion of the binding ligand wherein the complementary portion 117 of the binding ligand, the analyte molecule 62, and the capture component 60 form a portion 118, which remains immobilized with respect to the substrate.

In certain embodiments, at least some of the plurality of dissociated species released from a substrate are partitioned across a plurality of reaction sites, such as, for example, a plurality of reaction vessels (e.g., in an array format). The plurality of reaction vessels may be formed in or of any suitable material, and in some cases, the reaction vessels can be sealed or may be formed upon the mating of a substrate with a sealing component, as discussed in more detail below. In certain embodiments, especially where quantization of the analyte molecules is desired, the partitioning of the dissociated species is performed such that at least some (e.g., a statistically significant fraction) of the reaction vessels comprise at least one or, in certain cases, one dissociated species and at least some (e.g., a statistically significant fraction) of the reaction vessel comprise no dissociated species. The detectable species may be quantified in certain embodiments, thereby allowing for the detection and quantification of the analyte molecule in the fluid sample by techniques described in more detail below. In certain embodiments, the plurality of reactions vessels may comprise detection capture components, wherein the detection capture components are molecules or other entities able to specifically bind at least one dissociated species. The plurality of dissociated species may be detected in the reaction vessels, either indirectly or directly, as discussed more below.

Certain methods of the present invention may be useful for characterizing analyte molecules in a sample. In some cases, the methods may be useful for detecting and/or quantifying analyte molecules in a fluid sample which is suspected of containing at least one analyte molecule, since, as explained in more detail below, the number of reaction vessels which contain one or more of the dissociated species can be correlated to the concentration of analyte molecules in the fluid sample (e.g., the number of reaction vessels which comprise a dissociated species can be related to a measure of the concentration of the analyte molecules in the sample). Certain embodiments of present invention thus can provide a measure of the concentration of analyte molecules in a fluid sample based on the proportion of reaction vessels which contain a dissociated species. Specific methods and calculations of how to quantify analyte molecules in a fluid sample using embodiments of the invention are discussed more below.

Exemplary Basic Assay Formats

The inventive assays may be carried our according to a very wide variety of basic protocols and formats. The particular format chosen can be based on the nature of the analyte molecules and the availability and properties of binding partners of the analyte as well as other factors. Several exemplary basic formats were discussed previously in the context of the discussion of FIGS. 1-4. As would be apparent to those skilled in the art with the benefit of the teachings provided by the present disclosure, the invention may alternatively be performed according to protocols/formats not specifically described in the specific, exemplary embodiments illustrated in this detailed description, but which do not require undue burden or experimentation to practice.

In certain embodiments, a method for determining a measure of the concentration of analyte molecules or particles in a fluid sample is provided that comprises capturing a plurality of analyte molecules or particles (e.g., though association with a capture component) on a first substrate (e.g., beads, microtiter plate, etc.). A plurality of molecules or particles is released (e.g., dissociated) from the first substrate. At least a portion of the molecules or particles released (dissociated species) from the first substrate are detected on or within a second substrate, which in certain embodiments comprises a plurality of reaction vessels (e.g., an etched end of a fiber optic bundle—see below). A measure of the concentration of the analyte molecules or particles in the initial fluid sample can then be determined based on a measure of quantification of the molecules or particles on or within the second substrate that were released from the first substrate.

In certain embodiments, a method for determining a measure of the concentration of analyte molecules or particles in a fluid sample comprises first capturing a plurality of analyte molecules or particles on a first substrate then releasing a plurality of molecules or particles (disassociated species) from the first substrate (e.g., immobilizing analyte molecules or particles with respect to a capture component on a first substrate to form a plurality of complexes and then releasing at least a portion of some of the complexes formed). In certain embodiments, at least one binding ligand comprising a binding partner for the molecule or particle released from the first substrate is immobilized with respect to each of at least a fraction of the plurality of molecules or particles released from the first substrate to form a plurality of complexes. In certain such cases, at least one of the binding ligands may advantageously comprise a particle to facilitate or enhance the performance of the assay, for example by one or more of: increasing the degree of capture of and/or enhancing the binding kinetics with the dissociated species; facilitating transfer of the disassociated species from the first substrate to the second substrate; and/or facilitating detection of the disassociated species on or within the second substrate. The plurality of complexes released from the first substrate can then be detected and quantified (e.g., by partitioning the plurality of dissociated species comprising particles across the plurality of reaction vessels), and a measure of the concentration of the analyte molecules or particles in the fluid sample may be determined based on the quantification of the dissociated species.

Figure 5:
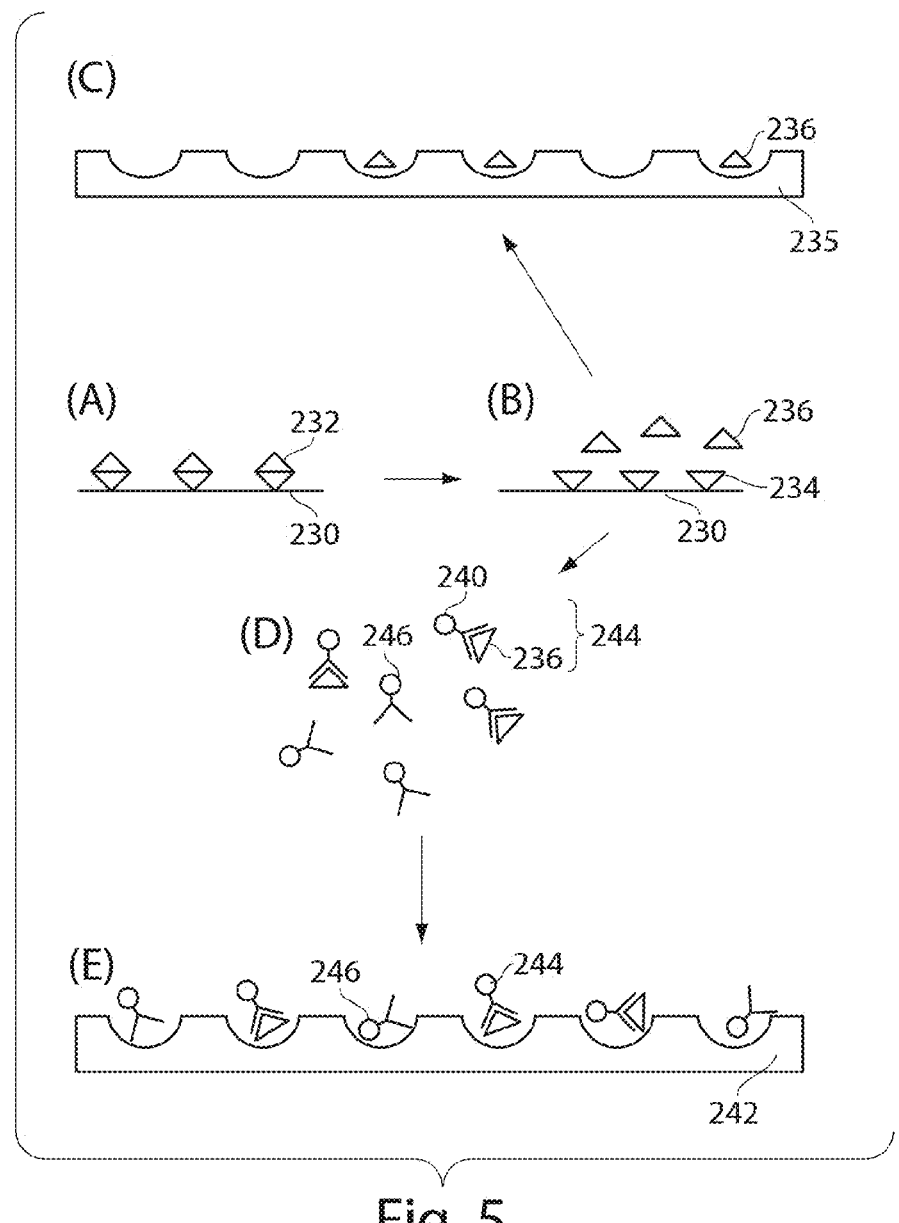
FIG. 5 is a schematic flow diagram depicting steps (A-E) of one embodiment of one method of the present invention.

An example of the above embodiment is depicted in FIG. 5. A plurality of analyte molecules or particles is captured on a first substrate 230 to form a plurality of immobilized complexes 232 (step (A)). At least a portion of some of the immobilized complexes are dissociated from the first substrate 230 and form a plurality of dissociated species 236 (step (B)). In some cases, the plurality of dissociated species may be formed by exposing the immobilized complexes to a reducing agent and/or by causing a cleavable linker located in the immobilized complex to cleave. In some cases, a portion of the immobilized complexes 234 may remain associated with the first substrate 230. The plurality of dissociated species may be detected and/or quantified, in some cases, by partitioning at least a portion of the plurality of dissociated species across a plurality of reaction vessels (step (C)). A measure of the concentration of the analyte molecules or particles in the fluid sample may be determined based on the quantification of dissociated species.

In some embodiments, the plurality of dissociated species may be exposed to a plurality of binding ligands. At least one binding ligand 240 comprising a binding partner for the molecule or particle released from the first substrate may be immobilized with respect to at least a fraction of the plurality of dissociated species 236 from the first substrate to form a plurality of complexes 244 forming a two-component dissociated species (step (D)). An excess of binding ligands 246 may be present in some cases. The plurality of two-component dissociated species 244 may then be detected and/or quantified, in some cases, by partitioning at least a portion of the plurality of complexes across a plurality of reaction vessels 242 (step (E)). In some cases, the plurality of binding ligands 246 that do not associate with a dissociated species may also be partitioned across the plurality of reaction vessels 242. A measure of the concentration of the analyte molecules or particles in the fluid sample may be determined based on the quantification of the complexes comprising a binding ligand and a dissociated species.

Figure 6:
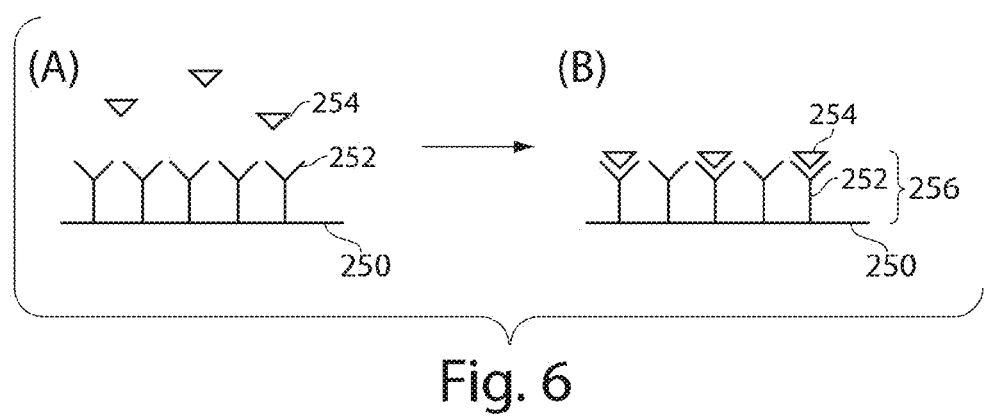
FIG. 6 depicts a second substrate comprising a plurality of capture components with which a plurality of dissociated species may become associated as shown by steps (A-B), according to one embodiment.

In certain embodiments, a method for determining a measure of the concentration of analyte molecules or particles in a fluid sample may be performed as described in any of the methods above with at least a fraction of the molecules or particles released from the first substrate (disassociated species) becoming immobilized with respect to the second substrate. For example, the second substrate may comprise a plurality of capture components with which the dissociated species may become associated. For example, as depicted in FIG. 6, second substrate 250 comprising a plurality of capture components 252 may be exposed to a plurality of dissociated species 254 (step (A)). At least a portion of dissociated species 254 may associate with capture components 252 on second substrate 250 to form complexes 256 (step (B)).

In some embodiments, the plurality of molecules may be released from the first substrate by exposure to a dissociating agent. For example, a substrate comprising a plurality of capture components may be exposed to a sample comprising a plurality of analyte molecules or particles, such that analyte molecules or particles associate with capture components to form a plurality of complexes, which are immobilized with respect to the substrate. Each of the immobilized complexes may comprise at least one capture component and at least one analyte molecule or particle. Exposure of the plurality of immobilized complexes to a reducing agent (e.g., beta-mercaptoethanol, dithiothreitol, tris(2-carboxyethyl)phosphine, etc.) causes at least a portion of at least some of the plurality of immobilized complexes to dissociate from the substrate to form a plurality of dissociated species. At least some of the dissociated species may be detected to determine the presence of and/or a measurement of the amount or concentration of the analyte molecules or particles in the fluid sample, as discussed more herein. The reducing agent may or may not be removed form the solution comprising the dissociated species prior to detection of the dissociated species, as discussed more herein. In some embodiments, the dissociating agent is a reducing agent (e.g., beta-mercaptoethanol). In some embodiments, the dissociating agent has essentially no specific affinity for the capture components. That is, the dissociating agent does not bring about release of the dissociating species by interacting with the capture component and employing competitive binding to release the analyte molecule that associated with the capture component.

Figure 7:
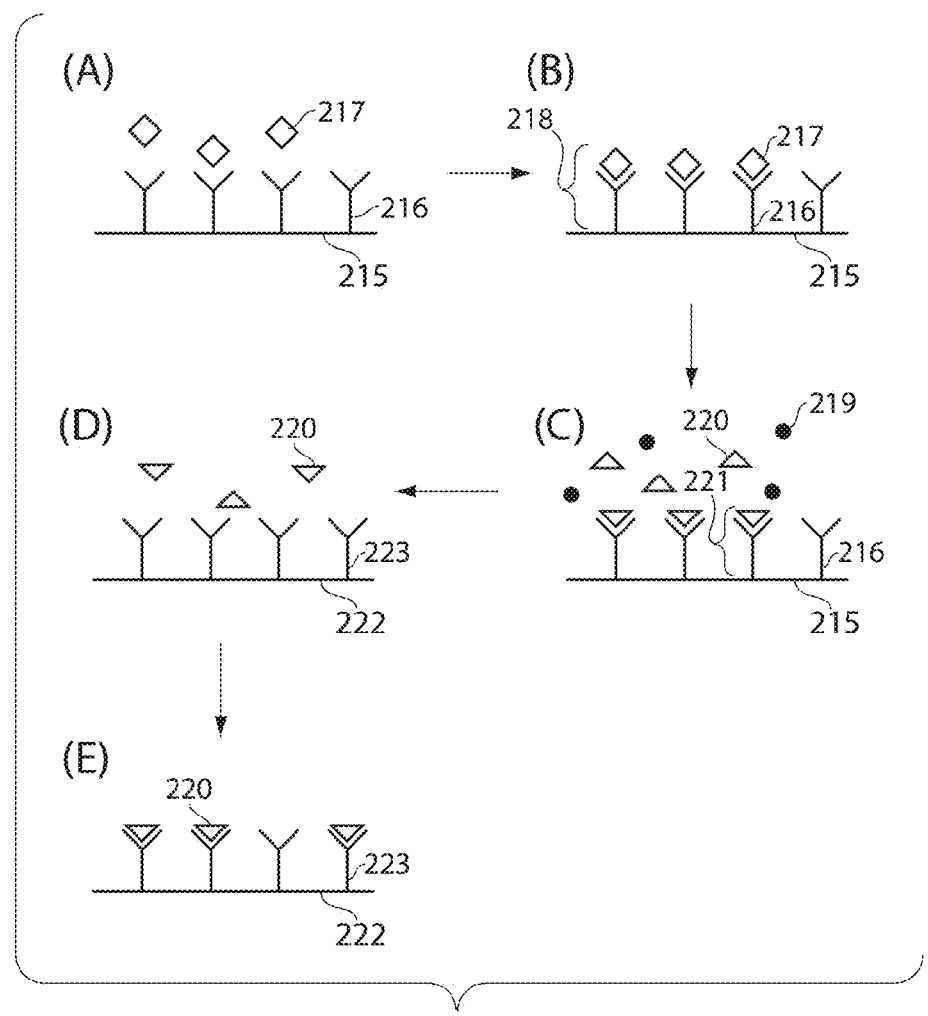
FIG. 7 is a schematic flow diagram depicting steps (A-E) of one embodiment of one method of the present invention.

The above example is illustrated in FIG. 7. First substrate 215 comprising a plurality of capture components 216 is exposed to a plurality of analyte molecules 217 (step (A)). At least some of the analyte molecules 217 associate with a capture component 216 on first substrate 215 to form a plurality of immobilized complexes 218 (step (B)). The first substrate is then exposed to a dissociating agent (e.g., a reducing agent) 219 and at least a portion of the immobilized complexes are dissociated to form a plurality of dissociated species 220 (step (C)). The complementary portion 221 of the immobilized complexes may remain associated with first substrate 215. The plurality of dissociated species 220 are then exposed to second substrate 222 comprising a plurality of capture components 223 which are able to specifically bind the dissociated species (step (D)). At least some of the dissociated species 220 are immobilized with respect to a capture component 223 (step (E)) and at least some of the dissociated species may be detected to determine the presence of and/or a measurement of the amount or concentration of the analyte molecules or particles in the fluid sample.

In some embodiments, the plurality of dissociated species may be formed by cleavage of cleavable linkages. For example, each of the immobilized complexes may comprise at least one cleavable linkage (e.g., a disulfide linkage). The cleavable linkage may located in a capture component, analyte molecule or a binding ligand and may be cleaved to form a plurality of dissociated species, for example, see FIG. 4 as discussed more herein. In a particular embodiment, the cleavable linkage is a disulfide linkage which may, in some cases, be cleaved by exposure of the immobilized complexes to a reducing agent.

In some embodiments, at least a portion of an immobilized complex comprises an enzymatic component. That is, at least one of the capture component, the analyte molecule or any additional components of the immobilized complex (e.g., binding ligand(s)) comprises an enzymatic component. In some cases, the enzymatic component may be located in the portion of the immobilized complex which is dissociated from the first substrate to form a dissociated species. For example, FIG. 8 illustrate an exemplary embodiment of an assay wherein the binding ligand comprises a moiety (e.g., an enzymatic component), as discussed more herein.

In certain embodiments, the protocol may include the use of at least one binding ligand, at least a portion of which comprises at least a portion of the dissociated species transferred from the first substrate to the second substrate (e.g., the binding ligand may be immobilized prior to release or following release of the molecules or particles from the first substrate). In some embodiments, the binding ligand comprises a cleavable linkage (e.g., a disulfide linkage) and/or is dissociated from the first substrate by exposure to a reducing agent. In some embodiments, at least one binding ligand comprises an enzymatic component. For example, the binding ligand(s), or at least the portions thereof forming at least a portion of the dissociated species transferred from the first substrate to the second substrate, may further comprise a moiety (e.g., an enzymatic component or enzyme substrate) able to convert a precursor labeling agent molecule (e.g., an enzymatic substrate) into a labeling agent (e.g., a detectable product). After transfer of and, optionally, capture of the dissociated species on or within the second substrate, the second substrate may be exposed to a plurality of precursor labeling agent molecules, wherein the plurality of precursor labeling agent molecules are converted to a plurality of labeling agent molecules upon exposure to a binding ligand. A measure of the concentration of the analyte molecules or particles in the fluid sample can then be determined based on the measurement of the labeling agent molecules on or within the second substrate.

Figure 8:
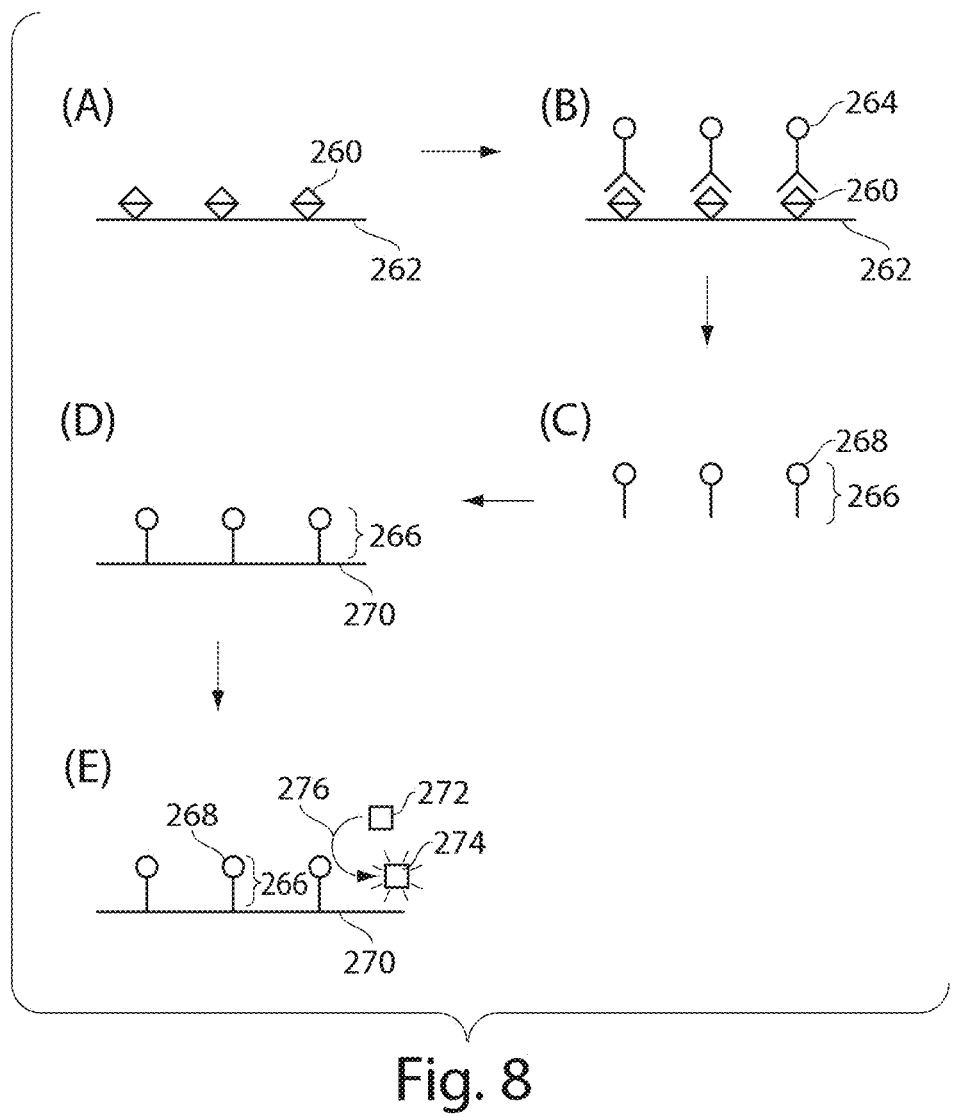
FIG. 8 is a schematic flow diagram depicting steps (A-E) of one method of the present invention, according to one embodiment.

For example, as shown in FIG. 8, a plurality of analyte molecules are immobilized with respect to first substrate 262 to form a plurality of immobilized complexes 260 (step (A)). First substrate 262 is exposed to a plurality of binding ligands 264 which associate with immobilized complexes 260 (step (B)). In this illustrated example, a portion of at least some of binding ligands 264 are dissociated from the first substrate to form a plurality of dissociated species 268 (step (C)) (e.g., by exposure to a dissociating agent and/or by cleavage of a cleavable linker). Each dissociated species 268 comprises a moiety 266 which is able to convert a precursor labeling agent molecule into a labeling agent. The plurality of dissociated species 266 is immobilized with respect to second substrate 270 (step (D)). The second substrate is exposed to a plurality of precursor labeling agent molecules 272, at least some of which are converted to a labeling agent molecules 274 upon exposure to moiety 268 of dissociated species 266, as indicated by arrow 276 (step (E)).

Figure 9:
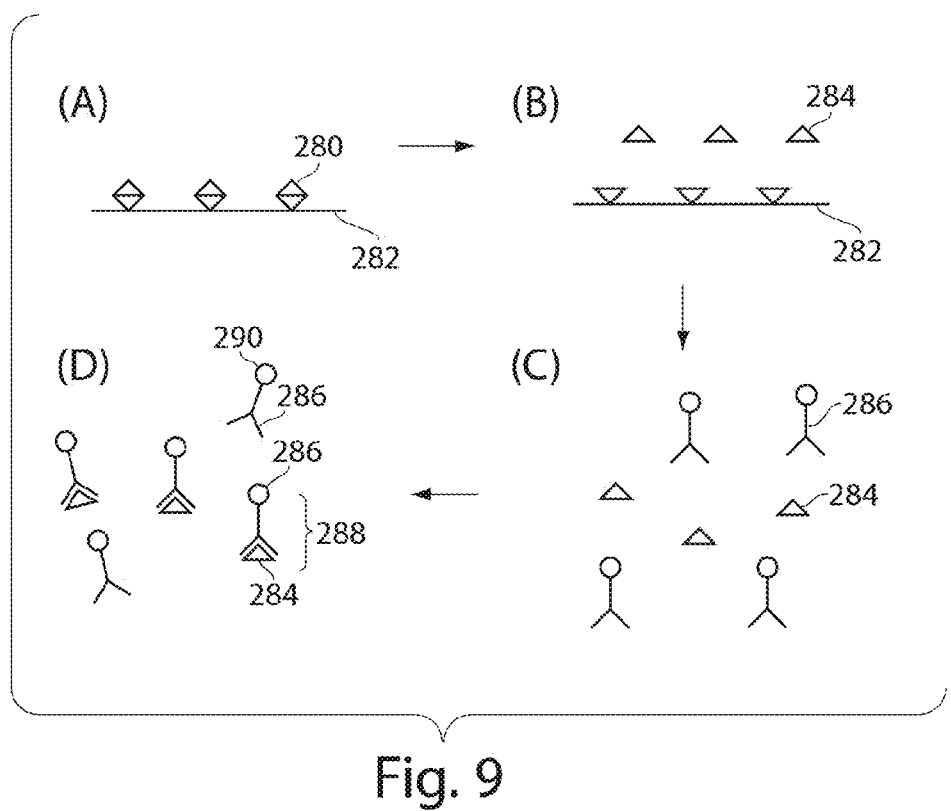
FIG. 9 is a schematic flow diagram depicting steps (A-D) of one embodiment of one method of the present invention.

As another example, as shown in FIG. 9, a plurality of analyte molecules are immobilized with respect to first substrate 282 to form a plurality of immobilized complexes 280 (step (A)). At least a portion of at least some of the immobilized complexes are dissociated from first substrate 282 to form a plurality of dissociated species 284 (step (B)) (e.g., by exposure to a dissociating agent and/or by cleavage of a cleavable linker). A plurality of dissociated species 284 may be exposed to a plurality of binding ligands 286 (step (C)). Binding ligands 286 may associated with at least some of the dissociated species 284 to form a plurality of complexes 288 forming a two-component dissociated species (i.e. binding ligand 286 and species 284) (step (D)). In some cases, binding ligand 286 may comprise a moiety 290 that is able to convert a precursor labeling agent molecule into a labeling agent. The detection and/or quantification of the dissociated species (comprising a binding ligand) may be carried out according to the methods discussed herein.

In certain method of the invention substantially all of the detected dissociated species that are applied to the second substrate become spatially separated with respect to the other detected dissociated species during detection (e.g., by being located in separate and distinct areas of the second substrate, such as separate reaction vessels), so that detection of the dissociated species is able to resolve individual dissociated species (i.e. individual molecules or particles) of the plurality of dissociated species. The ability to achieve spatially separated species may aid in the determination of a measure of the concentration of analyte molecules in a fluid sample and/or the detection of a plurality of species substantially simultaneously. The ability to spatially separate a plurality of dissociated species may permit low numbers of dissociated species to be detected and quantified, thereby enabling measurement of very low concentrations of analyte molecules in a fluid sample to be tested.

In some embodiments, a system may be provided comprising a first substrate comprising a plurality of capture components and a second substrate configured to receive and contain dissociated species therein or thereon. The system can additionally comprise a detector configured to detect dissociated species in or on the second substrate. The plurality of capture components may be able to become specifically immobilized with respect to a plurality of analyte molecules or particles in the fluid sample, such that the analyte molecules or particles associate with capture components to form a plurality of immobilized complexes. At least a portion of at least some of the complexes is susceptible to being dissociated from the first substrate by exposure to a reducing agent, to form a plurality of dissociated species.

In certain embodiments, the systems and/or methods of the present invention can be employed using precursor labeling agent molecules, wherein the precursor labeling agent molecules are converted to labeling agent molecules which are insoluble in the liquid substantially surrounding the labeling agent molecules (e.g., the liquid in the reaction vessel) and/or which become immobilized with respect to the second substrate (e.g., within the reaction vessel). For example, the systems and/or methods of the present invention may be used in combination with the systems and/or methods as described in commonly owned U.S. patent application Ser. No. 12/236,484, filed Sep. 23, 2008, entitled "High Sensitivity Determination of the Concentration of Analyte Molecules or Particles in a Fluid Sample" by Duffy, et al.

Systems and Kits

In some embodiments of the present invention, a system for detecting analyte molecules or particles in a fluid sample is provided. The system may comprise a first substrate comprising a plurality of capture components configured for specifically immobilizing the analyte molecules or particles with respect to the substrate to form a plurality of immobilized complexes. The complexes may be configured to be susceptible to being dissociated from the first substrate by a dissociating agent, e.g., by cleaving of a cleavable linker to form a plurality of dissociated species. The system may further comprise a second substrate comprising an array comprising a plurality of reaction vessels. The reaction vessels may be configured to receive and contain dissociated species therein.

In certain embodiments, a system for detecting analyte molecules or particles in a fluid sample may comprise a first substrate comprising a plurality of capture components able to become specifically immobilized with respect to a plurality of analyte molecules or particles in the fluid sample, such that the analyte molecules or particles associate with capture components to form a plurality of immobilized complexes. At least a portion of the some of the immobilized complexes, in this embodiment, may be susceptible to being dissociated from the first substrate by exposure to a reducing agent, to form a plurality of dissociated species. The system may also comprise a second substrate configured to receive and contain dissociated species therein or thereon and a detector configured to detect dissociated species in or on the second substrate.

Figure 10A:
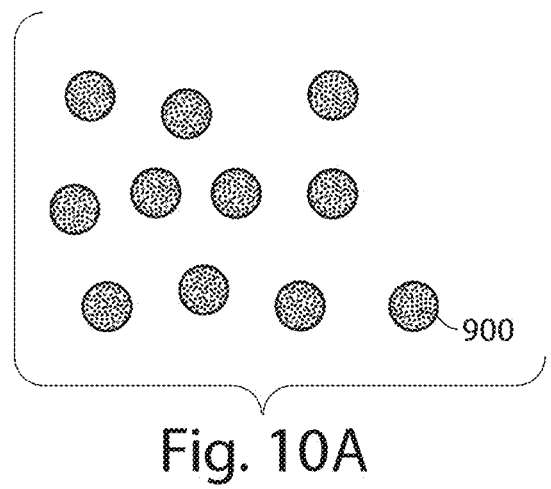
FIGS. 10A-10C show non-limiting examples of substrates that may be used according to certain embodiments of the present invention.
Figure 10B:
Figure 10C:
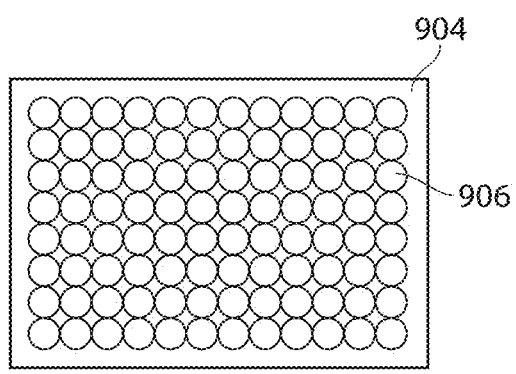

In some embodiments, the first substrate may comprise a plurality of beads 900 (e.g., magnetic beads), a planar surface 902, or a microtiter plate 904, as shown in FIGS. 10A-10C, respectively, and as discussed in more detail herein. Second substrates may comprise a plurality of reaction vessels are also discussed in more detail herein. In a particular embodiment, the plurality of reaction vessels may be formed in the end of a fiber optic bundle. The volume of each of the reactions vessels of the second substrate may be between about 10 attoliters and about 100 picoliters or between about 10 femtoliters and about 100 femtoliters, in certain embodiments, as discussed previously. In some embodiments, the plurality of reaction vessels may comprise a plurality of dissociated species capture components to which dissociated species are able to become specifically immobilized. The second substrate may, in some embodiments, further comprise a sealing component configured for sealing the plurality of reaction vessels. In certain embodiments, the second substrate comprises a substantially planar surface and the sealing component comprises a plurality of microwells, such that a plurality of reaction vessels is formed upon the mating of at least a portion of the planar surface with at least a portion of the sealing component comprising the plurality of microwells. In certain embodiments, the plurality of reaction vessels may be formed upon the mating of at least a portion of a sealing component and at least a portion of the second substrate, as shown in FIGS. 11A-11F and as discussed in more detail herein.

Capture Components

In some embodiments of the present invention, the surfaces of a substrate (e.g., the substrate on which the analyte molecules or particles form an immobilized complex ("first substrate") or the substrate to which the dissociated species are transferred ("second substrate")) may, as mentioned previously, incorporate at least one type of capture component. As mentioned above, a capture component is any molecule, other chemical/biological entity or solid support modification disposed upon a solid support that can be used to specifically attach, bind or otherwise capture a target molecule or particle (e.g., an analyte molecule or dissociated species), such that the target molecule/particle becomes immobilized with respect to the capture component and solid substrate. Generally, the capture component allows the attachment of a molecule, particle or complex to a solid support (that is, a surface of a substrate) for the purposes of immobilization, detection, quantification, and/or other analysis of the molecule, particle or complex. A capture component is used in the present invention, in some cases, to immobilize an analyte molecule with respect to the first substrate. In some cases, a capture component may comprise a cleavable linkage, as discussed more below. Although much of the following discussion focuses on a capture component with respect to the immobilization of an analyte molecule, it should be understood that the same types of capture components may, as appropriate, be used to immobilize dissociated species as well. Those of ordinary skill in the art will be able to select appropriate capture component in accordance with the material (e.g., analyte molecule or dissociated species) to be immobilized.

As will be appreciated by those in the art, the composition of the capture component will depend on the composition of the analyte molecule (or dissociated species). Capture components for a wide variety of target molecules are known or can be readily found using known techniques. For example, when the target molecule is a protein, the capture components may comprise proteins, particularly antibodies or fragments thereof (e.g., antigen-binding fragments (Fabs), Fab' fragments, pepsin fragments, $F(ab')_2$ fragments, full-length polyclonal or monoclonal antibodies, antibody-like fragments, etc.), other proteins, such as receptor proteins, Protein A, Protein C, etc., or small molecules. In some cases, capture components for proteins comprise peptides. For example, when the target molecule is an enzyme, suitable capture components may include enzyme substrates and enzyme inhibitors. In some cases, when the target analyte is a phosphorylated species, the capture component may comprise a phosphate-binding agent. For example, the phosphate-binding agent may comprise metal-ion affinity media such as those describe in U.S. Pat. No. 7,070,921 and U.S. Patent Application No. 20060121544. In addition, when the target molecule is a single-stranded nucleic acid, the capture component may be a complementary nucleic acid. Similarly, the target molecule may be a nucleic acid binding protein and the capture component may be a single-stranded or double-stranded nucleic acid; alternatively, the capture component may be a nucleic acid-binding protein when the target molecule is a single or double stranded nucleic acid. Alternatively, as is generally described in U.S. Pat. Nos. 5,270,163, 5,475,096, 5,567,588, 5,595,877, 5,637,459, 5,683,867, 5,705,337, and related patents, nucleic acid "aptamers" may be developed for capturing virtually any target molecule. As will be appreciated by those or ordinary skill in the art, any molecule that can specifically associate with a target molecule of interest may potentially be used as a capture component. For example, when the target molecule is a carbohydrate, potentially suitable capture components include, for example, antibodies, lectins and selectins.

For certain embodiments, suitable target molecule (e.g., analyte molecule or dissociated species)/capture component pairs can include, but are not limited to, antibodies/antigens, receptors/ligands, proteins/nucleic acid, nucleic acids/nucleic acids, enzymes/substrates and/or inhibitors, carbohydrates (including glycoproteins and glycolipids)/lectins and/or selectins, proteins/proteins, proteins/small molecules; small molecules/small molecules, etc. According to one embodiment, the capture components are portions (particularly the extracellular portions) of cell surface receptors that are known to multimerize, such as the growth hormone receptor, glucose transporters (particularly GLUT 4 receptor), and T-cell receptors and the target analytes are one or more receptor target ligands.

In a particular embodiment, the capture component may be attached to a binding surface (for example, the surface of a microwell or of a microbead) via a linkage, which may comprise any moiety, functionalization, or modification of the binding surface and/or capture component that facilitates the attachment of the capture component to the surface. The linkage between the capture component and the surface may comprise one or more chemical or physical (e.g., non-specific attachment via van der Waals forces, hydrogen bonding, electrostatic interactions, hydrophobic/hydrophilic interactions; etc.) bonds and/or chemical linkers providing such bond(s). In certain embodiments, the capture component comprises a capture extender component. In such embodiments, the capture component comprises a first portion that binds the analyte molecule and a second portion that can be used for attachment to the binding surface.

In certain embodiments, the substrate surface may also comprise a protective or passivating layer that can reduce or minimize non-specific attachment of non-capture components (e.g., analyte molecules, binding ligands, dissociated species) to the binding surface during the assay which may lead to false positive signals during detection or to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein; surfactants, e.g. zwitterionic surfactants, such as sulfobetaines; naturally occurring long-chain lipids; and nucleic acids, such as salmon sperm DNA.

The method of attachment of the capture component to the substrate surface depends of the type of linkage employed and may potentially be accomplished by a wide variety of suitable coupling chemistries/techniques known to those of ordinary skill in the art. The particular means of attachment selected will depend on the material characteristics of the substrate surface and the nature of the capture component. In certain embodiments, the capture components may be attached to the substrate surface through the use of reactive functional groups on each. According to one embodiment, the functional groups are chemical functionalities. That is, the binding surface may be derivatized such that a chemical functionality is presented at the binding surface which can react with a chemical functionality on the capture component resulting in attachment. Examples of functional groups for attachment that may be useful include, but are not limited to, amino groups, carboxy groups, epoxide groups, maleimide groups, oxo groups and thiol groups. Functional groups can be attached, either directly or through the use of a linker, the combination of which is sometimes referred to herein as a "crosslinker." Crosslinkers are known in the art; for example, homo- or heterobifunctional crosslinkers as are well known (e.g., see 1994 Pierce Chemical. Company catalog, technical section on crosslinkers, pages 155-200, or "Bioconjugate Techniques" by Greg T. Hermanson, Academic Press, 1996). Non-limiting example of crosslinkers include alkyl groups (including substituted alkyl groups and alkyl groups containing heteroatom moieties), esters, amide, amine, epoxy groups and ethylene glycol and derivatives. A linker may also be a sulfone group, forming a sulfonamide.

According to one embodiment, the functional group is a light-activated functional group. That is, the functional group can be activated by light to attach the capture component to the substrate surface. One example is PhotoLink™ technology available from SurModics, Inc. in Eden Prairie, Minn.

In some cases, the substrate may comprise streptavidin-coated surfaces and the capture component may be biotinylated. Exposure of the capture component to the streptavidin-coated surfaces can cause association of the capture component with the surface by interaction between the biotin component and streptavidin.

In certain embodiments, attachment of the capture component to the binding surface may be effected without covalently modifying the binding surface of a substrate. For example, the attachment functionality can be added to the binding surface by using a linker that has both a functional group reactive with the capture component and a group that has binding affinity for the binding surface. In certain embodiments, a linker comprises a protein capable of binding or sticking to the binding surface; for example, in one such embodiment, the linker is serum albumin with free amine groups on its surface. A second linker (crosslinker) can then be added to attach the amine groups of the albumin to the capture component (e.g., to carboxy groups).

According to one embodiment in which a chemical crosslinker is used to attach the capture components to the substrate, the analyte molecule may be captured on the binding surface of a substrate using a capture component attached via chemical crosslinking in the following manner. First, the binding surface is derivatized with a functional group, such as, an amine group. Next, a crosslinker and the capture component are placed in contact with the binding surface such that one end of the crosslinker attaches to the amine group and the capture component attaches to the other end of the crosslinker. In this way, capture components comprising proteins, lectins, nucleic acids, small organic molecules, carbohydrates can be attached.

One embodiment utilizes proteinaceous capture components. As is known in the art, any number of techniques may be used to attach a proteinaceous capture component to a wide variety of solid surfaces. "Protein" or "proteinaceous" in this context includes proteins, polypeptides, peptides, including, for example, enzymes and antibodies. A wide variety of techniques are known to add reactive moieties to proteins, for example, the method outlined in U.S. Pat. No. 5,620,850. The attachment of proteins to surfaces is known, for example, see Heller, Acc. Chem. Res. 23:128 (1990), and many other similar references.

In some embodiments, the capture component (or binding ligand) may comprise Fab' fragments. The use of Fab' fragments as opposed to whole antibodies may help reduce non-specific binding between the capture component and the binding ligand. In some cases, the Fc region of a capture component (or binding ligand) may be removed (e.g., proteolytically). In some cases, an enzyme may be used to remove the Fc region (e.g., pepsin, which may produce $F(ab')_2$ fragments and papain, which may produce Fab fragments). In some instances, the capture component may be attached to a binding surface using amines or may be modified with biotin (e.g., using NHS-biotin) to facilitate binding to an avidin or streptavidin coated substrate surface. $F(ab')_2$ fragments may be subjected to a chemical reduction treatment (e.g., by exposure to 2-mercaptoethylamine) to, in some cases, form two thiol-bearing Fab' fragments. These thiol-bearing fragments can then be attached via reaction with a Michael acceptor such as maleimide. For example, the Fab' fragments may then be treated with a reagent (e.g., maleimide-biotin) to attach at least one biotin moiety (i.e., biotinylated) to facilitate attachment to streptavidin-coated surfaces as described above.

Certain embodiments utilize nucleic acids as the capture component, for example for when the analyte molecule is a nucleic acid or a nucleic acid binding protein, or when the it is desired that the capture component serve as an aptamer for binding a protein, as is well known in the art.

According to one embodiment, each binding surface of a substrate comprises a plurality of capture components. The plurality of capture components, in some cases, may be distributed randomly on the binding surface like a "lawn." Alternatively, the capture components may be spatially segregated into distinct region(s) and distributed in any desired fashion.

Binding between the capture component and the analyte molecule, in certain embodiments, is specific, e.g., as when the capture component and the analyte molecule are complementary parts of a binding pair. In certain such embodiments, the capture component binds both specifically and directly to the analyte molecule. By "specifically bind" or "binding specificity," it is meant that the capture component binds the analyte molecule with specificity sufficient to differentiate between the analyte molecule and other components or contaminants of the test sample. For example, the capture component, according to one embodiment, may be an antibody that binds specifically to some portion of an analyte molecule (e.g., an antigen). The antibody, according to one embodiment, can be any antibody capable of binding specifically to an analyte molecule of interest. For example, appropriate antibodies include, but are not limited to, monoclonal antibodies, bispecific antibodies, minibodies, domain antibodies, synthetic antibodies (sometimes referred to as antibody mimetics), chimeric antibodies, humanized antibodies, antibody fusions (sometimes referred to as "antibody conjugates"), and fragments of each, respectively. As another example, the analyte molecule may be an antibody and the capture component may be an antigen.

According to one embodiment in which an analyte particle is a biological cell (e.g., mammalian, avian, reptilian, other vertebrate, insect, yeast, bacterial, cell, etc.), the capture component may be a ligand having specific affinity for a cell surface antigen (e.g., a cell surface receptor). In one embodiment, the capture component is an adhesion molecule receptor or portion thereof, which has binding specificity for a cell adhesion molecule expressed on the surface of a target cell type. In use, the adhesion molecule receptor binds with an adhesion molecule on the extracellular surface of the target cell, thereby immobilizing or capturing the cell. In one embodiment in which the analyte particle is a cell, the capture component is fibronectin, which has specificity for, for example, analyte particles comprising neural cells.

In some embodiments, as will be appreciated by those of ordinary skill in the art, it is possible to detect analyte molecules using capture components for which binding to analyte molecules/dissociated species that is not highly specific. For example, such systems/methods may use different capture components such as, for example, a panel of different binding ligands, and detection of any particular analyte molecule/dissociated species is determined via a "signature" of binding to this panel of binding ligands, similar to the manner in which "electronic noses" work. This may find particular utility in the detection of certain small molecule analytes. In some embodiments, the binding affinity between analyte molecules and capture components should be sufficient to remain bound under the conditions of the assay, including wash steps to remove molecules or particles that are non-specifically bound. In some cases, for example in the detection of certain biomolecules, the binding constant of the analyte molecule or dissociated species to its complementary capture component may be between at least about $10^4$ and about $10^6$ M$^{-1}$, at least about $10^5$ and about $10^9$ M$^{-1}$, at least about $10^7$ and about $10^9$ M$^{-1}$, greater than about $10^9$ M$^{-1}$, or the like.

In certain embodiments, the capture component is chosen to be able to bind to a corresponding binding partner associated with or attached to the analyte molecule or dissociated species. For example, the capture component according to one embodiment is a chemical crosslinker as described above able to bind to proteins generally. According to one embodiment, every protein molecule in a fluid sample comprises an analyte molecule that attaches to such a chemical crosslinker. In another example, the capture component comprises streptavidin, which binds with high affinity to biotin, and thus captures any analyte molecules to which biotin has been attached. Alternatively, the capture component may be biotin, and streptavidin may be attached to or associated with the analyte molecules such that the analyte molecules can be captured by the biotin.

According to one embodiment, the binding surfaces of a substrate may be functionalized with capture components in the following manner. First, the surface of a substrate (e.g., one end of a fiber optic bundle, a plurality of microbeads, etc.) is prepared for attachment of the capture component(s) by being modified to form or directly bind to the capture components, or a linker may be added to the binding surface of the substrate such that the capture component(s) attaches to the binding surface of the substrate via the linker. In one embodiment, the binding surfaces of the substrate are derivatized with a chemical functionality as described above. Next, the capture component may be added, which binds to and is immobilized by the chemical functionality.

Figure 12:
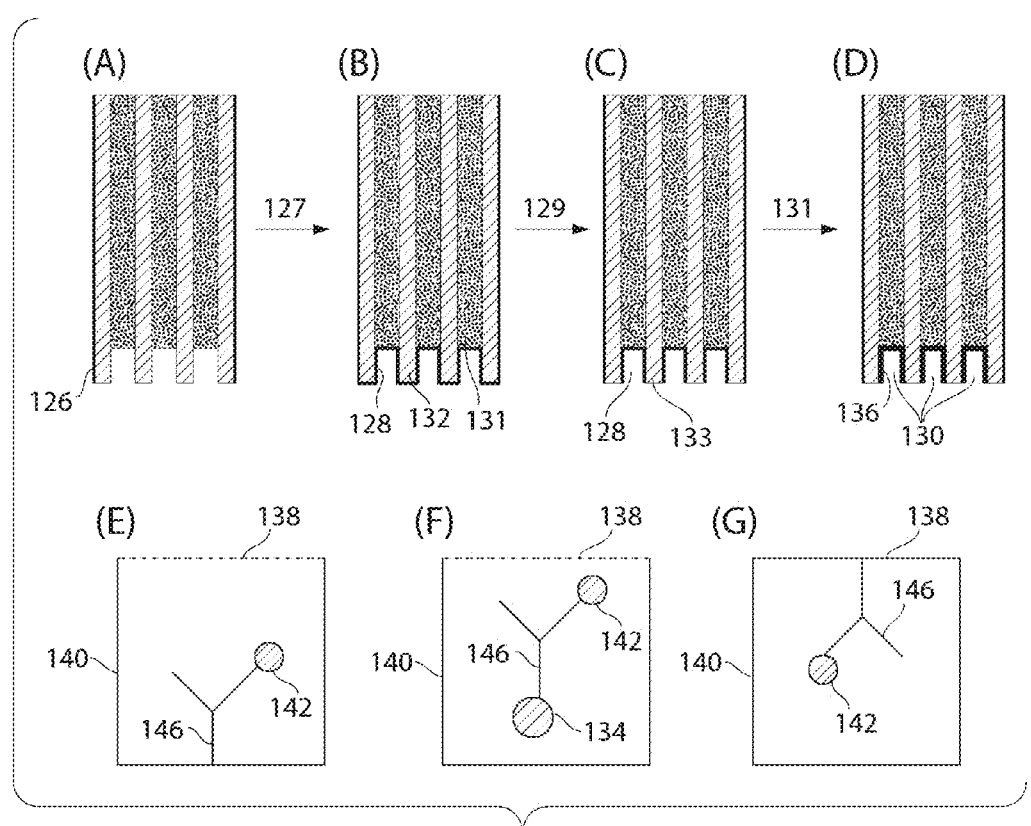
FIG. 12 shows side view cross-section schematics showing an etched fiber optic bundle that forms an array of microwells (steps A-D), according to one embodiment of the present invention, and depicting the localization of a capture component within a reaction vessel (steps E-G), according to some embodiments of the present invention.

A specific embodiment is depicted in FIG. 12, in which the binding surface comprises an array of microwells functionalized with biotin. As shown in panel (A), an array of microwells 130 in this non-limiting example is formed at the end of a fiber optic bundle 126. To attach the capture component, the binding surface of the microwells 130 are first modified (e.g., with aminopropyl silane), as indicated by arrow 127, which may be bound to both the core 131 and cladding 132 surfaces of the end of the fiber bundle 126, as shown in FIG. 12, panel (B). However, in certain embodiments, the capture component should be present only within the microwells, the external surfaces of the fiber optic bundle, such as the external surfaces 133 of the cladding 132, should not be modified. In certain cases, after treatment, chemical functionalities may be removed from the external cladding surface 133 to avoid attachment of a capture component in this region. In this example, as shown in FIG. 12, panel (C), and as indicated by arrow 129, treated binding surface 128 may be removed from the external cladding portion 133, e.g., by polishing the tip of the fiber optical bundle (e.g., for 10 seconds with 0.3 um lapping film), thereby removing the topmost layer of the cladding in this region, thereby removing the added binding moieties. After functionalization of the binding surface of the microwells, the capture component can be attached, as indicated by arrow 131 and shown in FIG. 12, panel (D). In one embodiment, the surface is treated with aminopropyl silane and the capture component comprises biotin or is labeled with biotin. For example, referring to FIG. 12, panel (D), a capture component comprising biotin succinimidyl ester 136 is attached to the amino groups of treated surface 128 of the microwells 130. The modification with aminopropyl silane is effective in this example because NHS-biotin attaches to an amino-silanized binding surface 128.

Examples of capture components 146 and exemplary association of capture components with an analyte molecule 142 within a reaction vessel 130 are depicted in FIG. 12, panels (E-G). A capture component 146 may be localized directly on the surface of the microwell 130, which may contain an optional seal 138, on a microparticle 134 contained within the microwell 130 (FIG. 12, panel (F)), and/or on the seal 138 of the microwell 130 (FIG. 12, panel (G)). Additional locations where a capture component may be immobilized and additional substrates that may be used for one or both of capturing an analyte molecule or a dissociated species according to certain methods of the invention are discussed more below.

In some embodiments only a single analyte molecule associates with each capture component. However, in some instances, more than one analyte molecule may be immobilized with respect to each capture component, in which case, an immobilized complex may comprise a capture component and at least two analyte molecules. In yet other cases, a single analyte molecule may become immobilized with respect to two or more capture components (either of the same or differing types) such that an immobilized complex comprises at least two capture component and an analyte molecule. In some cases, at least about 50%, at least about 60%, at least about 70%, at least about 80%, at least about 90%, at least about 95%, at least about 97%, at least about 99%, or the like, of analyte molecules in the fluid sample exposed to the binding substrate become immobilized with respect to at least one capture component.

Substrates

In some embodiments, the method and systems of the present invention comprise a first substrate and a second substrate. In certain embodiments, the first substrate comprises a plurality of capture component with specificity for target analyte molecules (or particles) in a fluid sample to be tested, while the second substrate comprises a plurality of capture component with specificity for dissociated species released from the first substrate. The second substrate in certain embodiments comprises the substrate utilized for detection and quantization and to facilitate this comprises a plurality of reaction vessels in which a plurality of dissociated species (or molecules or particles) released from first substrate are partitioned across or received and contained in. The discussion below will first focus on the first substrate, and then focus on the second substrate. It should be understood, that the first substrate and the second substrate, in some embodiments, may be interchanged with each other, may be essentially the same in configuration or may be different in configuration.

The first substrate may be fabricated from any suitable material, for example, plastics, polysaccharides, nylon or nitrocellulose, composite materials, ceramics, silica or silica-based materials, carbon, metals, inorganic glasses, and a variety of other polymers. Non-limiting examples of potentially suitable configurations include of beads (e.g., magnetic beads), microtiter plates, slides, membranes, plates, flasks, dipsticks, optical fibers, or the like. In some embodiments, the first substrate may comprise a planar surface 902, for example, as shown in FIG. 10B.

In a particular embodiment, the first substrate comprises a plurality of beads 900 (FIG. 10A). The beads may each comprise a plurality of capture components by which a plurality of analyte molecules may be immobilized. Without wishing to be bound by any theory, the use of beads or other large surface area formats as the first substrate may increase the speed and/or efficiency in which a plurality of analyte molecules are immobilized with respect to the substrate. This is because the solution comprising the plurality of analyte molecules and beads may be agitated (e.g., stirred) and may increase the rate of exposure of the substrate (e.g., bead) to an analyte molecule, as compared to a first substrate comprising a different configuration (e.g., a microtiter plate).

In some embodiments, the beads may be magnetic beads. The magnetic property of the beads may help in separating the beads from a solution (e.g., comprising a plurality of dissociated species) and/or during washing step(s) (e.g., to remove excess fluid sample, binding ligands, and/or dissociated species). Potentially suitable beads, including magnetic beads, are available from a number of commercial suppliers. In certain embodiments, the diameter of the beads may be greater than about 0.1 um, greater than about 1 um, greater than about 10 um, greater than about 100 um, greater than about 1 mm, or the like. In other embodiments, the diameter of the beads may be between about 0.1 um and about 100 um, between about 1 um and about 100 um, between about 10 um and about 100 um, between about 0.1 um and about 1 mm, between about 10 um and about 10 mm, between about 0.1 um and about 10 um, or the like.

In another set of embodiments, e.g. as illustrated in FIG. 10C, the first substrate comprises a microtiter plate 904, wherein each well 906 of the plate comprises a plurality of capture components. The volume of each well may be greater than about 1 nL, greater than about 10 nL, greater than about 100 nL, greater than about 1 uL, greater than about 10 uL, greater than about 100 uL, greater than about 1 mL, greater than about 2 mL, or the like. In other cases, the volume of each well may be between about 1 nL and about 2 mL, between about 10 nL and about 1 nL, between about 100 nL and about 100 uL, between about 10 uL and about 1 mL, between about 100 uL and about 1 mL, or the like. The number of wells in the microtiter plate may be any appropriate number for example about 6, about 24, about 96, about 384, about 1536, or the like. The number of wells may be between about 5 and about 2000, about 10 and about 1000, about 20 and about 500, about 50 and about 100, or the like. In some cases, the microtiter plate may be a 96-well plate (FIG. 10C). Microtiter plates may be purchased from many commercial sources.

In some embodiments, the second substrate is employed for the detection and/or quantification of a plurality of dissociated species (e.g., molecules or particles released from the first substrate) and comprises a plurality of small volume reaction vessels. The second substrate, in certain embodiments, is configured to receive and contain dissociated species therein or thereon (e.g., within wells comprising capture components having specificity for the dissociated species, or within wells without such capture components but including means for sealing of the wells of the substrate—e.g., through use of a sealing component (see below), etc.). The plurality of dissociated complexes can be partitioned across a plurality of reaction vessels of the second substrate (e.g., configured as an array of reaction vessels), in some cases, to facilitate determination of a measure of the concentration of dissociated species and thereby a measure of the concentration of analyte molecules in a fluid sample by means discussed in further detail below and in the examples.

In some embodiments of the present invention, the plurality of reaction vessels may be formed through the mating of the second substrate and a sealing component, wherein at least one of the second substrate and the sealing component comprises a plurality of microwells. In some cases, (e.g., as shown in FIG. 12, panels (E-G)) an array comprises a plurality of depressions in a first surface of the second substrate (e.g., a support material). The sealing component may comprise a second surface with the same or different topology as the first surface may be brought into contact with the first surface to create a plurality of sealed reaction vessels. Either the first surface or the second surface may be fabricated from a compliant material to aid in sealing. Either or both of the surfaces may be hydrophobic or contain hydrophobic regions to minimize leakage of aqueous samples from the microwells. In some cases, the sealing component may be capable of contacting the exterior surface of an array of microwells (e.g., the cladding of a fiber optic bundle as shown in FIG. 12) such that each reaction vessel thus formed is sealed or isolated such that the contents of each reaction vessel cannot escape the reaction vessel. According to one embodiment, the sealing component may be a silicone elastomer gasket that may be placed against an array of microwells with application of uniform pressure across the entire substrate. In some cases, the reaction vessels may be sealed after the addition of a dissociated species and, optionally, a precursor labeling agent molecule to facilitate detection of the dissociated species. For embodiments employing precursor labeling agent molecules, by sealing the contents in some of each reaction vessel, a reaction to produce the detectable labeling agent molecule can proceed within the sealed reaction vessels, thereby producing a detectable amount of a labeling agent molecule that is retained in the reaction vessel for detection purposes. In some cases, the plurality of reaction vessels formed on a planar second substrate upon the mating of at least a portion of a sealing component comprising a plurality of microwells and at least a portion of the planar substrate (e.g., see FIG. 11B below).

Figure 11:
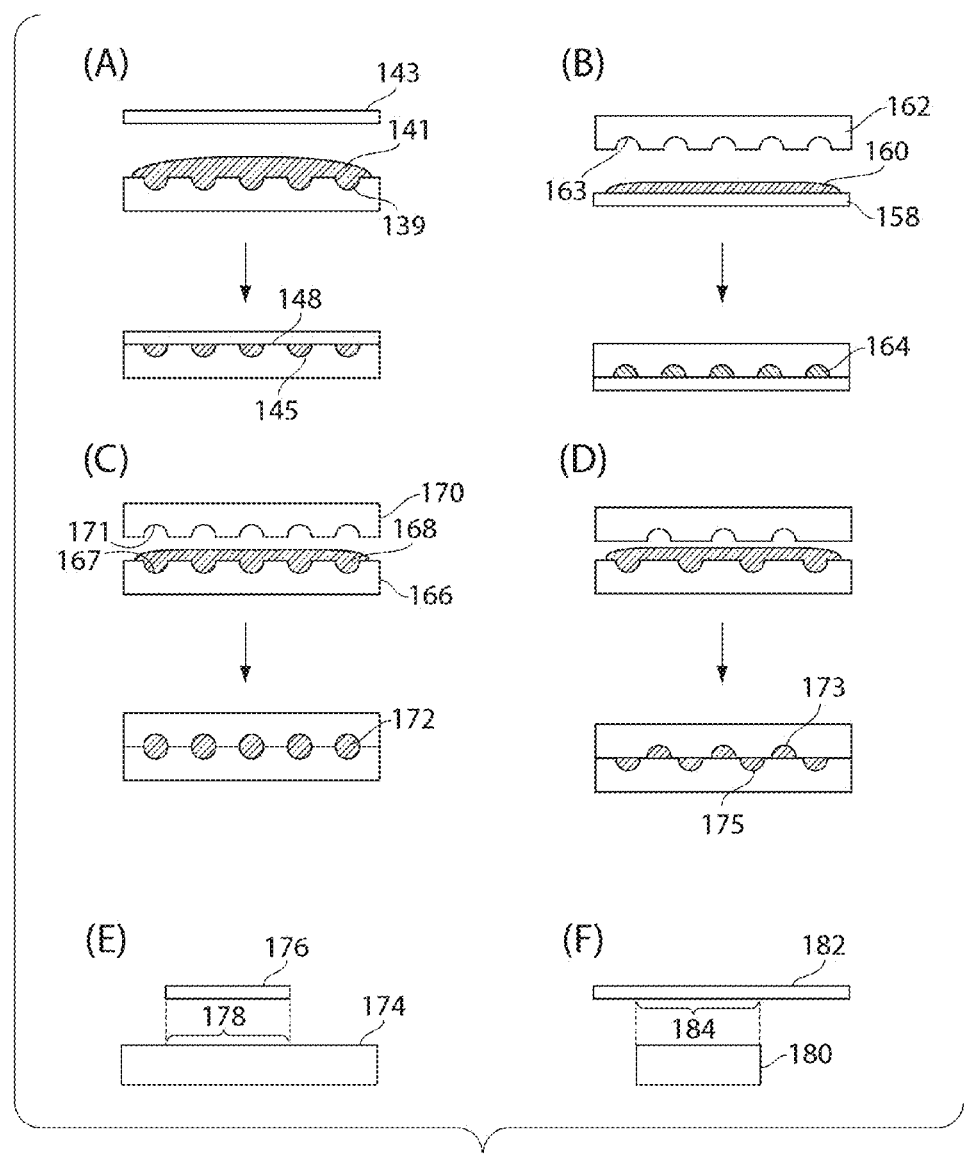
FIG. 11 is a schematic flow diagram depicting an embodiment of a method (steps A-D) for the formation of a plurality of reaction vessels through mating of a substrate and a sealing component and depicting examples of the size (E, F) of a sealing component relative to a substrate.

Non-limiting embodiments of the formation of a plurality of reaction vessels on the second substrate are depicted in FIG. 11. FIG. 11, panel (A) shows a surface comprising a plurality of microwells 139, which have been exposed to a fluid sample 141, and a sealing component 143. Sealing component 143 in this example comprises a substantially planar bottom surface. Mating of the microwell containing surface 139 with sealing component 143 forms a plurality of sealed reaction vessels 145. The areas between the reaction vessels 148, may be modified to aid in the formation of a tight seal between the reaction vessels.

A second embodiment is shown in FIG. 11, panel (B), in which sealing component 162 comprising a plurality of microwells 163 is mated with a substantially planar surface 158 which has been exposed to fluid sample 162, thereby forming a plurality of reaction vessels 164.

In a third embodiment, as shown in FIG. 11, panel (C), substrate surface 166 comprising a plurality of microwells 167 is mated with sealing component 170 also comprising a plurality of microwells 171. In this embodiment, the microwells in the substrate and the microwells in the sealing components are substantially aligned so each reaction vessel 172 formed comprises a portion of the microwell from the sealing component and a portion of a microwell from the substrate. In FIG. 11, panel (D), the microwells are not aligned such that each reaction vessel comprises either a microwell from the sealing component 173 or a microwell from the substrate 175.

The sealing component may be essentially the same size as the substrate or may be different in size. In some cases, the sealing component is approximately the same size as the substrate and mates with substantially the entire surface of the substrate. In other cases, as depicted in FIG. 11, panel (E), the sealing component 176 is smaller than the substrate 174 and the sealing component only mates with a portion 178 of the substrate. In yet another embodiment, as depicted in FIG. 11, panel (F), the sealing component 182 is larger than the substrate 180, and only a portion 184 of the sealing component mates with the substrate 180.

In some embodiments, the reaction vessels may all have approximately the same volume. In other embodiments, the reaction vessels may be of differing volumes. The volume of each individual reaction vessel can range for different embodiments from attoliters or smaller to nanoliters or larger depending upon the nature of dissociated species, the detection technique and equipment employed, and the expected concentration of the dissociated species in the fluid applied to the second substrate for analysis. In one embodiment, the size of the reaction vessel may be selected such that at the concentration of interest, between zero and ten molecules/particles of a dissociated species would be statistically expected to be found in each reaction vessel. In a particular embodiment, the volume of the reaction vessel is selected such that at the concentration of interest, either zero or one molecules/particles of the dissociated species would be statistically expected to be found in each reaction vessel. In accordance with one embodiment of the present invention, the reaction vessels may have a volume between about 1 femtoliter and about 1 picoliter, between about 10 femtoliters and about 100 femtoliters, between about 10 attoliters and about 50 picoliters, between about 1 picoliter and about 50 picoliters, between about 1 femtoliter and about 1 picoliter, between about 30 femtoliters and about 60 femtoliters, or the like. In some cases, the reaction vessels have a volume of less than about 1 picoliter, less than about 500 femtoliters, less than about 100 femtoliters, less than about 50 femtoliters, less than about 1 femtoliter, or the like. In some cases, the reaction vessels have a volume of about 10 femtoliters, about 20 femtoliters, about 30 femtoliters, about 40 femtoliters, about 50 femtoliters, about 60 femtoliters, about 70 femtoliters, about 80 femtoliters, about 90 femtoliters, about 100 femtoliters, or the like.

The number of reaction vessels in the array will depend on the composition and end use of the array. Arrays containing from about 2 to many billions of reaction vessels can be made by utilizing a variety of techniques and materials. Increasing the number of reaction vessels in the array can be used to increase the dynamic range of an assay or to allow multiple samples or multiple types of dissociated species to be assayed in parallel. Generally, the array will comprise between one thousand and one million reaction vessels per sample to be analyzed. In some cases, the array will comprise greater than one million reaction vessels. In some embodiments, the array will comprise between about 1,000 and about 50,000, between about 1,000 and about 1,000,000, between about 1,000 and about 10,000, between about 10,000 and about 100,000, between about 100,000 and about 1,000,000, between about 1,000 and about 100,000, between about 50,000 and about 100,000, between about 20,000 and about 80,000, between about 30,000 and about 70,000, between about 40,000 and about 60,000, or about 50,000, or the like, reaction vessels.

The array of reaction vessels may be arranged on a substantially planar surface or in a non-planar three-dimensional arrangement. The reaction vessels may be arrayed in a regular pattern or may be randomly distributed. In a specific embodiment, the array is a regular pattern of sites on a substantially planar surface permitting the sites to be addressed in the X-Y coordinate plane.

In some embodiments, the reaction vessels are formed in a solid material. As will be appreciated by those in the art, the number of potentially suitable materials in which the reaction vessels can be formed is very large, and includes, but is not limited to, glass (including modified and/or functionalized glass), plastics (including acrylics, polystyrene and copolymers of styrene and other materials, polypropylene, polyethylene, polybutylene, polyurethanes, Teflon®, polysaccharides, nylon or nitrocellulose, etc.), elastomers (such as poly(dimethyl siloxane) and poly urethanes), composite materials, ceramics, silica or silica-based materials (including silicon and modified silicon), carbon, metals, optical fiber bundles, or the like. In general, the substrate material may be selected to allow for optical detection without appreciable autofluorescence. In certain embodiments, the reaction vessels may be formed in a flexible material.

Individual reaction vessels may contain a binding surface. The binding surface may comprise essentially the entirety or only a portion of the interior surface of the reaction vessel or may be on the surface of another material or object that is confined within the reaction vessel, such as, for example, a bead, or a particle (for example, a micro-particle or a nano-particle).

A microwell in a surface (e.g., substrate or sealing component) may be formed using a variety of techniques known in the art, including, but not limited to, photolithography, stamping techniques, molding techniques, etching techniques, or the like. As will be appreciated by those of the ordinary skill in the art, the technique used will depend on the composition and shape of the supporting material and the size and number of reaction vessels.

Figure 13A:
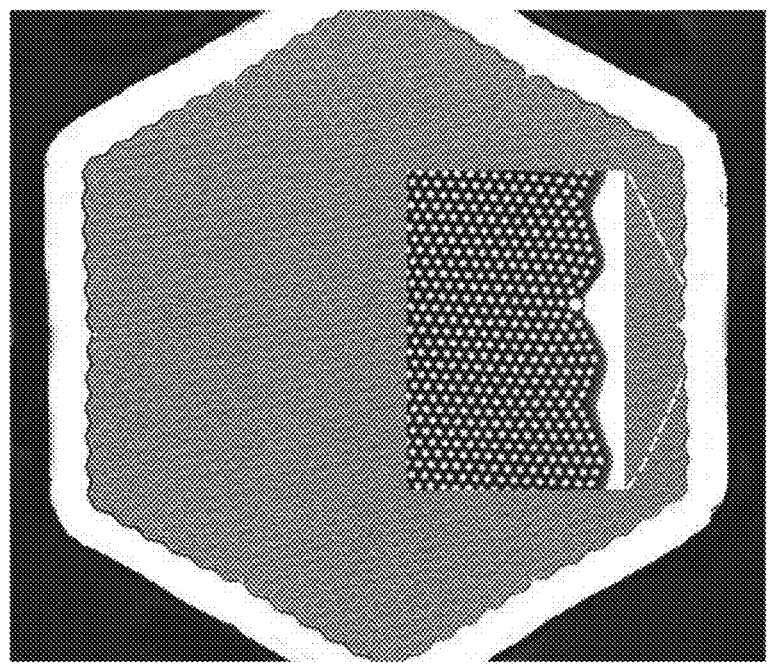
FIG. 13A is a photocopy of a photomicrograph of an entire fiber optic array, with an inset showing a close-up of the bundle, according to one embodiment of the present invention.
Figure 13B:
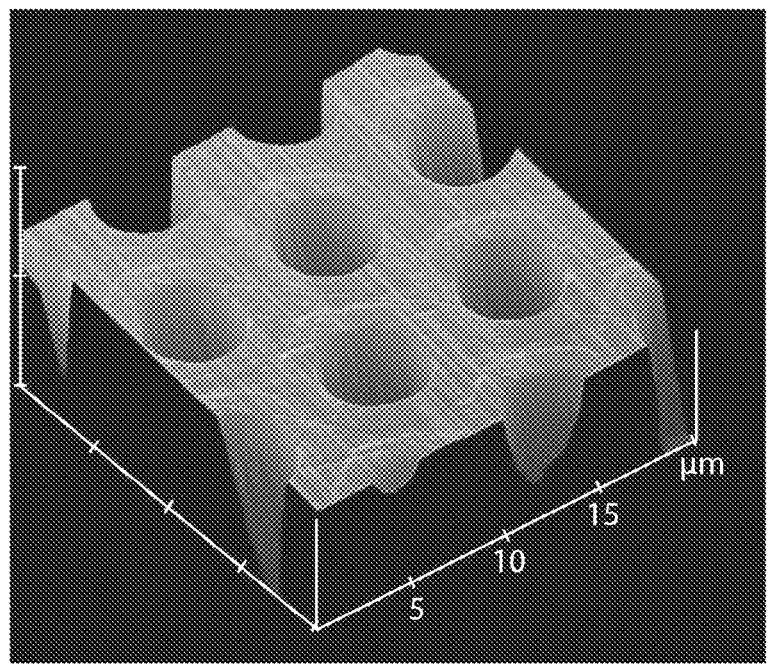
FIG. 13B is a photocopy of an atomic force microscope (AFM) image of a portion of an etched surface of a fiber optic array, according to one embodiment of the present invention.

In a particular embodiment, an array of reaction vessels is formed by creating microwells on one end of a fiber optic bundle and utilizing a planar compliant surface as a sealing component. In certain such embodiments, an array of reaction vessels in the end of a fiber optic bundle may be formed as follows. First, an array of microwells is etched into the end of a polished fiber optic bundle. Techniques and materials for forming and etching a fiber optic bundle are known to those of ordinary skill in the art. For example, the diameter of the optical fibers, the presence, size and composition of core and cladding regions of the fiber, and the depth and specificity of the etch may be varied by the etching technique chosen so that microwells of the desired volume may be formed. In certain embodiments, the etching process creates microwells by preferentially etching the core material of the individual glass fibers in the bundle such that each well is approximately aligned with a single fiber and isolated from adjacent wells by the cladding material. Potential advantages of the fiber optic array format is that it can produce thousands to millions of reaction vessels without complicated microfabrication procedures and that it can provide the ability to observe and optically address many reaction vessels simultaneously. An example of an etched fiber optic array is shown in FIGS. 13A and 13B. FIG. 13A shows a fiber optic array that has been etched to form a plurality or reaction vessels. In this particular example, the wells have a diameter of approximately 4.5 um and a volume of about 46 fL. FIG. 13B shows an AFM image of a portion of the fiber optic array of FIG. 13A.

Each microwell may be aligned with an optical fiber in the bundle so that the fiber optic bundle can carry both excitation and emission light to and from the wells, enabling remote interrogation of the well contents. Further, an array of optical fibers may provide the capability for simultaneous or non-simultaneous excitation of molecules in adjacent vessels, without signal "cross-talk" between fibers. That is, excitation light transmitted in one fiber does not escape to a neighboring fiber.

In certain embodiments of the present invention, the physical alterations to a fiber optic may be made as taught in U.S. Pat. Nos. 6,023,540, 6,327,410, and 6,858,394. Any one or more of the surface of the glass microwells, the surface of the sealing component, or particles within microwells can be functionalized in certain embodiments to create binding surface(s).

Alternatively, the equivalent structures can be fabricated using other methods that do not utilize the ends of an optical fiber bundle as a substrate. For example, the array may be a spotted, printed or photolithographically fabricated substrate produced by techniques known in the art; see for example WO95/25116; WO95/35505; PCT US98/09163; U.S. Pat. Nos. 5,700,637, 5,807,522, 5,445,934, 6,406,845, and 6,482,593. In some cases, the array may be produced using molding and/or etching techniques as will be known to those of ordinary skill in the art.

In certain embodiments, the present invention provides a system equipped with a mechanical platform that applies a sealing component to a substrate. The platform may be positioned beneath a stage on the system. After the chosen reaction components have been added to an array of reaction vessels, the sealing component may be mated with the array. For example, the sealing component may be sandwiched between a flat surface (such as, for example, a microscope slide) and the array of reaction vessels using uniform pressure applied by the mechanical platform.

Figure 14A:
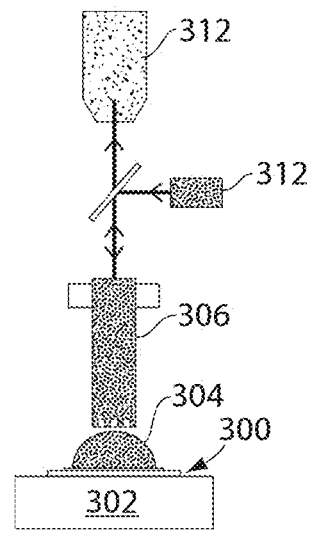
FIG. 14A depicts an experimental set-up for detection using light, according to one embodiment of the present invention.
Figure 14B:
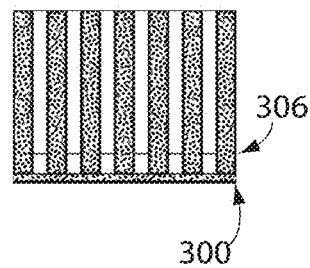
FIG. 14B shows a fiber optic array that has been sealed with a sealing component, according to one embodiment.

A non-limiting embodiment is illustrated in FIG. 14A. A sealing component 300 is placed on top of mechanical platform 302. The fluid sample 304 is placed on top of the sealing component 300. The mechanical platform is moved upwards towards the array 306 (e.g., fiber optic array) such that uniform pressure is applied. As shown in FIG. 14B, the sealing component 300 forms a tight seal with the array 306. In other instances, varying pressure may be applied to the sealing component to form a tight seal between the sealing component and the array. The system may also comprise additional components 312 that may be utilized to analyze the array (e.g., microscope, computer, etc.) as discussed more herein.

In some embodiments, the first and/or second substrate to which the analyte molecules/dissociated species are immobilized may be subjected to at least one washing step. In one instance, a substrate may be washed after exposing the substrate to one or more solutions comprising analyte molecules, binding ligands, precursor labeling agent molecules, or dissociated species. In some instances, the wash step(s) may be used to wash away any analyte molecules or non-analyte molecules, any binding ligands or non-binding ligands, any precursor labeling agent molecules or non-precursor labeling agent molecules, or any dissociated species or non-dissociated species that are not immobilized with respect to the substrate. The wash step(s) may be performed by any suitable technique known to those of ordinary skill in the art, for example, by submersion of the substrate in a wash solution, flushing the substrate with a wash solution, etc. In certain embodiments, the wash solution is selected so that it does not cause appreciable change to the configuration of the substrate surface and/or does not disrupt an interaction between at least two components of the assay (e.g., a capture component and an analyte molecule/dissociated species). In other cases, the wash solution may be a solution that is selected to chemically interact with one or more components of the substrate. As will be understood by those of ordinary skill in the art, a wash step may be performed at any appropriate time point during the inventive methods (e.g., after exposure of the substrate to a reagent or after immobilization of and agent with respect to a substrate) during a method of the present invention.

Exemplary Target Analytes

As will be appreciated by those in the art, a large number of analyte molecules and particles may be detected and, optionally, quantified using methods and systems of the present invention; basically, any analyte molecule or particle that is able to be made to become immobilized with respect to (e.g., by binding) a capture component can be potentially investigated using the invention. Certain more specific targets of potential interest that may comprise an analyte molecule or particle are mentioned below. The list below is exemplary and non-limiting.

In some embodiments, the analyte molecule may be an enzyme. Non-limiting examples of enzymes include, an oxidoreductase, transferase, kinase, hydrolase, lyase, isomerase, ligase, and the like. Additional examples of enzymes include, but are not limited to, polymerases, cathepsins, calpains, amino-transferases such as, for example, AST and ALT, proteases such as, for example, caspases, nucleotide cyclases, transferases, lipases, enzymes associated with heart attacks, and the like. When a system/method of the present invention is used to detect the presence of viral or bacterial agents, appropriate target enzymes include viral or bacterial polymerases and other such enzymes, including viral or bacterial proteases, or the like.

In other embodiments, the analyte molecule or particle may comprise an enzymatic component. For example, the analyte particle can be a cell having an enzyme or enzymatic component present on its extracellular surface. Alternatively, the analyte particle is a cell having no enzymatic component on its surface. Such a cell is typically identified using an indirect assaying method described below. A non-limiting example of an enzymatic component is beta-galactosidase.

In yet other embodiments, the analyte molecule may be a biomolecule. Non-limiting examples of biomolecules include hormones, antibodies, cytokines, proteins, nucleic acids, lipids, carbohydrates, lipids cellular membrane antigens and receptors (neural, hormonal, nutrient, and cell surface receptors) or their ligands, or combinations thereof. Non-limiting embodiments of proteins include peptides, polypeptides, protein fragments, protein complexes, fusion proteins, recombinant proteins, phosphoproteins, glycoproteins, lipoproteins, or the like. As will be appreciated by those in the art, there are a large number of possible proteinaceous analyte molecules that may be detected or evaluated for binding partners using the present invention. In addition to enzymes as discussed above, suitable protein analyte molecules include, but are not limited to, immunoglobulins, hormones, growth factors, cytokines (many of which serve as ligands for cellular receptors), cancer markers, etc.

In certain embodiments, the analyte molecule may be a host-translationally modified protein (e.g., phosphorylation, methylation, glycosylation) and the capture component may be an antibody specific to a post-translational modification. Modified proteins may be captured with capture components comprising a multiplicity of specific antibodies and then the captured proteins may be further bound to a binding ligand comprising a secondary antibody with specificity to a post-translational modification. Alternatively, modified proteins may be captured with capture components comprising an antibody specific for a post-translational modification and then the captured proteins may be further bound to binding ligands comprising antibodies specific to each modified protein.

In another embodiment, the analyte molecule is a nucleic acid. A nucleic acid may be captured with a complementary nucleic acid fragment (e.g., an oligonucleotide) and then optionally subsequently labeled with a binding ligand comprising a different complementary oligonucleotide.

Suitable analyte molecules and particles include, but are not limited to small molecules (including organic compounds and inorganic compounds), environmental pollutants (including pesticides, insecticides, toxins, etc.), therapeutic molecules (including therapeutic and abused drugs, antibiotics, etc.), biomolecules (including hormones, cytokines, proteins, nucleic acids, lipids, carbohydrates, cellular membrane antigens and receptors (neural, hormonal, nutrient, and cell surface receptors) or their ligands, etc), whole cells (including prokaryotic (such as pathogenic bacteria) and eukaryotic cells, including mammalian tumor cells), viruses (including retroviruses, herpesviruses, adenoviruses, lentiviruses, etc.), spores, etc.

The fluid sample comprising or suspected of comprising and analyte molecule or particle may be derived from any suitable source. In some cases, the sample may comprise a liquid, fluent particulate solid, fluid suspension of solid particles, supercritical fluid and/or gas. In some cases, the analyte molecule or particle may be separated or purified from its source prior to determination; however, in certain embodiments, an untreated sample containing the analyte molecule or particle may be tested directly. The source of the analyte molecule may be synthetic (e.g., produced in a laboratory), the environment (e.g., air, soil, etc.), a mammal, an animal, a plant, or any combination thereof. In a particular example, the source of an analyte molecule is a human bodily substance (e.g., blood, serum, plasma, urine, saliva, tissue, organ, or the like).

Binding Ligands and Precursor Labeling/Labeling Agent Molecules

Binding ligands may be selected from any suitable molecule, particle, or the like, as discussed more below, able to associate with an analyte molecule and/or to associate with another binding ligand. For example, when only a first binding ligand is employed, a first binding ligand may associate with an analyte molecule. In another example, when a first binding ligand and a second binding ligand are employed, a first binding ligand may associate with an analyte molecule and a second binding ligand may become immobilized with respect to the analyte molecule by becoming associated with the first binding ligand. Some non-limiting examples of potentially suitable binding ligands are discussed more below.

Certain binding ligands can comprise a component that is able to facilitate detection, either directly or indirectly. A component may facilitate indirect detection, for example, by converting a precursor labeling agent molecule to a labeling agent molecule (e.g., an agent that is detected in an assay). In some embodiments, the binding ligand may comprise an enzymatic component (e.g., horseradish peroxidase, beta-galactosidase, etc). A first binding ligand may or may not be used in conjunction with additional (e.g., second, etc.) binding ligands, examples of which are discussed herein.

A "precursor labeling agent" is any molecule, particle, or the like, that can be converted to a labeling agent molecule upon exposure to a suitable converting agent. Such a converting agent may, in certain embodiments, comprise at least a portion of at least one of a capture component, an analyte, and/or a binding ligand. In certain such embodiments, it is advantageous if the converting agent comprises at least a portion of the dissociated species released from the first substrate and transferred to the second substrate for detection. A "labeling agent" is any molecule, particle, or the like, that facilitates detection, by acting as the detected entity, using a chosen detection technique.

In some embodiments, binding ligands may be selected such that are able to function in the following manner. If only a first binding ligand is employed, the first binding ligand may associate directly with an analyte molecule. In other cases, if both a first and a second binding ligand are employed, the first binding ligand may associate with an analyte molecule and comprise a component which is able to interact with the second binding ligand. Certain assays may also comprise additional components (e.g., a third binding ligand that can interact with the second binding ligand, first binding, or analyte). In certain embodiments, any one or more of the binding ligands may comprise at least a portion thereof able to convert a precursor labeling agent into a labeling agent molecule. In some cases, an assay component may be able to associate with more than one other assay component, for example, a third binding ligand may associate with both a first and a second binding ligand.

As mentioned above, in certain embodiments, a first binding ligand may be employed alone or in conjunction with a second (and a third, etc.) binding ligand. A first binding ligand may be selected (e.g., in the case when only a first and a second binding ligand is employed) such that it may associate with an analyte molecule and be able to interact with the second binding ligand (e.g., such that the first binding ligand is associated with the second binding ligand).

In some embodiments, the substrate (e.g., the substrate in/on which the plurality of analyte molecules are immobilized) may be exposed to a plurality of first binding ligands such that a first binding ligand associates with substantially all of the plurality of analyte molecules or particles to form a plurality of immobilized complexes. In some cases, the substrate may also be exposed to a plurality of second binding ligands such that the second binding ligand associates with substantially all of the plurality of first binding ligands which are associated with an analyte molecule or particle to form a plurality of immobilized complexes.

In yet other cases, the substrate may be additionally exposed to a plurality of third binding ligands such that a third binding ligand associates with substantially all of the second binding ligands which are associated with a first binding ligand which are associated with an analyte molecule or particle to form at least a portion of the plurality of immobilized complexes. Substantially all, as used herein, refers to at least greater than 80%, greater than 85%, greater than 90%, greater than 95%, greater than 97%, greater than 98%, greater than 99%, greater than 99.5%, or more, of a molecule/particle/species of a specific type.

As discussed more below, a binding ligand (e.g., a first, second and/or third, etc. binding ligand) may comprise a cleavable linker (e.g., disulfide). In some cases, at least one of the binding ligands may comprise biotin.

In some cases, binding ligands of the present invention may be functionalized to reduce non-specific binding, e.g., direct binding or association of a binding ligand to another component (e.g., capture component, surface of a substrate, etc.) of the assay, where such binding is undesired. In certain such embodiments, the binding ligand may be functionalized with a large steric molecule and/or particle which prevent the binding ligand from approaching and/or associating with the substrate, another component, etc. For example, the binding ligand may be functionalized with poly(ethylene glycol) groups or particles, poly(ethylene oxide) groups or particles (e.g., particles which are protein resistant such as beads coated in poly(ethylene glycol), DNA, or zwitterionic lipids).

Dissociation/Release of Immobilized Complexes/Species

In some embodiments, a plurality of dissociated species is formed during the assay. A "dissociated species," as used herein, is a molecule, complex, or particle (which, as previously noted, includes biological cells and sub cellular organelles) at least a portion of which has been released/dissociated from a molecule, complex, particle, surface, etc., to which it was immobilized. The dissociated species may form by causing an association (e.g., bond, attachment, etc.) to cleave, thereby releasing the dissociated species. A molecule or particle may be released from a substrate in certain instances without causing cleavage of a bond (e.g., by physical means); such released molecules or particles may still be referred to herein as dissociated species.

The plurality of dissociated species, in some cases, may be formed by the dissociation of at least a portion of a plurality of complexes immobilized with respect to a substrate. Each immobilized complex, in most cases, will comprise an analyte molecule, a capture component, and, in some cases, at least one binding ligand. In some cases, each immobilized complex may additionally comprise at least one cleavable linker (e.g., a disulfide linker) and/or an enzymatic component. A dissociated species, therefore, may comprise any portion of the previously immobilized complex (e.g., at least a portion of any one or more of the analyte molecule, the capture component and/or the at least one binding ligand). For example, at least one or each of the plurality of dissociated species may comprise at least a portion of a capture component, analyte molecule, and/or binding ligand(s) (e.g., first, second, third, etc., binding ligands).

The number of dissociated species released from the substrate may be, but need not be, substantially equal to the total number of analyte molecules or particles in the fluid sample and/or immobilized on the substrate. For example, in certain embodiments, the ratio of immobilized analyte molecules to dissociated species may be about 1:1, about 2:1, about 5:1, about 10:1, about 100:1, about 1000:1, about 10000:1, or the like. In some cases, the ratio is greater than about 1:1 but does not exceed 10:1, greater than about 10:1 but does not exceed 100:1, greater than about 100:1 but does not exceed 1000:1, greater than about 1000:1 but does not exceed 10000:1, greater than about 10000:1 but does not exceed 1,000,000:1, or greater than about 1,000,000:1 in certain embodiments. In some embodiments, the number of the plurality of immobilized molecules or particles released is approximately equal to, is directly proportional to, is about one half of, is about one quarter of, is about one tenth of, is about one hundredth of, is about one thousandth of, is about one ten-thousandth of, or is about one hundred-thousandth of, the number of the plurality of analyte molecules or particles captured.

A dissociated species, in some cases, may comprise a component which is able to be detected, either indirectly or directly (i.e., may comprise a labeling agent molecule and/or is capable of converting a precursor labeling agent molecule to a labeling agent molecule). The presence of a detectable component on a dissociated species can allow for the detection of the dissociated species, thereby allowing for the determination and/or quantification of the dissociated species. The determination and/or quantification of the dissociated species, can be related to the detection and/or quantification of the analyte molecule in a fluid sample, as discussed more below. In a particular embodiment, the detectable component is an enzymatic component.

In some embodiments, at least a portion of at least some of the immobilized complexes may be susceptible to being dissociated from a substrate by exposure to a dissociating agent, thereby forming a plurality of dissociated species. As mentioned above, non-limiting examples of dissociating agents include chemical dissociating agents, electromagnetic radiation, a change in the pH, a change in the temperature, etc. In a particular example, exposing the plurality of immobilized complexes to a reducing agent causes at least a portion of at least some of the plurality of complexes to dissociate from the substrate to form a plurality of dissociated species.

In some cases, the dissociating agent may have essentially no specific affinity for the capture components. That is, the dissociating agent does not cause the dissociating species to form by interacting with the capture component and employing competitive binding to release the analyte molecule that associated with the capture component. In some cases, when the dissociating agent has essentially no specific affinity for the capture component, the dissociated species may comprise an enzymatic component.

In some cases, each of the plurality of immobilized complexes may comprise a cleavable linkage and the plurality of dissociated species may be formed by cleaving at least some of the cleavable linkages. In some instances, a dissociating agent may be employed in conjunction with a cleavable linkage, wherein exposure of the cleavable linkage to the dissociating agent causes the cleavable linkage to cleave and a dissociated species to form. As mentioned above, a cleavable linkage is a linkage that is able to be cleaved upon exposure to a dissociating agent. The cleavable linkage may be present in any portion of the immobilized complex (e.g., the analyte molecule, the binding ligand (e.g., first, second or third, etc. binding ligand), the capture component, etc.). In some embodiments, the cleavable linkage may be a linkage that is specifically cleaved, that is, a linkage that can be cleaved without altering or damaging any other portion of the complex not being cleaved and which relatively uniformly alters the molecule in a reproducible manner. It should be understood, that a cleavable linkage may be selected depending on various parameters including desired size, solubility, ability to cleave or not cleave the linkage under certain conditions, the type of cleavage method to be used, etc. A cleavable linkage may be homobifunctional (e.g., contain two or more identical leaving groups) or heterobifunctional (e.g., contain two or more different leaving groups).

In some cases, the cleavable linkage may be a photocleavable linkage and the plurality of dissociated species may be formed by exposing the substrate to electromagnetic radiation (e.g., ultraviolet light). In certain such instances, the photocleavable linkage may be cleaved at a wavelength of light that does not damage the molecule being released, for example, in the ultraviolet to visible range. Non-limiting examples of photocleavable linkages include linkages containing o-nitrobenzyl, desyl, trans-o-cinnamoyl, m-nitrophenyl, benzylsulfonyl groups and others.

In some embodiments, the cleavable linkage may be a chemically cleavable linkage (i.e., susceptible to cleavage upon exposure to a chemical dissociating agent) Non-limiting examples of chemically cleavable linkages which may be cleaved by a chemical dissociating agent include a disulfide, which can be cleaved with reducing agents; a diol, which can be cleaved with periodates; a diazo bond, which can be cleaved with dithionates; an ester, which can be cleaved with hydroxylamines; a sulfone, which can be cleaved with bases, and others known in the art, as discussed more below. The concentration of dissociating agent used to bring about dissociation will depend on the type of cleavable linkage and dissociating agent employed as well as other assay conditions. The appropriate concentration and conditions to bring about a desired degree of dissociation may be selected in particular applications using routine screening tests and optimization. For example, in certain particular applications, the immobilized complexes may be exposed to a chemical dissociating agent in a concentration of between about 10 mM and about 100 mM, between about 1 mM and about 1 M, between about 0.1 M and about 1 M, etc.

In some embodiments, the plurality of dissociated species is formed by exposing the substrate to a chemical dissociating agent. The chemical dissociating agent may comprise at least one of a pH altering agent, an ionic strength altering agent, a denaturing agent, a reducing agent, a reactive agent, or an enzyme. In a particular embodiment involving immobilized complexes comprising thiol linkages, the chemical dissociating agent may comprise beta-mercaptoethanol. The plurality of complexes may be exposed to the chemical dissociating agent thereby forming a plurality of dissociated species. In some cases, a chemical dissociating agent is particularly suited to cleave a particular cleavable linkage. Non limiting combinations of chemical dissociating agents and cleavable linkages will now be discussed in more detail.

In some embodiments, the chemical dissociating agent is a reducing agent. A reducing agent is a compound or complex that chemically reduces another chemical species susceptible to chemical reduction which can, in certain cases, lead to scission of the species. In the case of a chemical dissociating agent that is a reducing agent, the immobilized complex may be reduced by the reducing agent and at least a portion of the complex may be dissociated by the reducing agent to form a dissociated species. Non-limiting examples of reducing agents that may be used to cleave a cleavable linkage include sodium borohydride, beta-mercaptoethanol, cysteine, tris(2-carboxyethyl)phosphine, zinc and dilute acid, triphenylphosphine ($Ph_3P$) and water, dithiothreitol (DTT), and others known in the art.

In some embodiments, a chemical dissociating agent may be substantially removed from the solution comprising the plurality of dissociated species prior to further manipulation of the plurality of dissociated species (e.g., partitioning of the plurality of dissociated species across a plurality of reaction vessels). For example, the chemical dissociating agent may be removed by filtration through a material to which the chemical dissociating agent may bind, by precipitation, or the like. In other embodiments, the chemical dissociated may not be substantially removed prior to further manipulation of the solution comprising the plurality of dissociated species.

In some embodiments, each immobilized complex may comprise a disulfide bond, some of which may be cleaved to form a plurality of dissociated species. In some cases, each immobilized complex may comprise at least one capture component, at least one analyte molecule or particle, and at least one disulfide linkage. At least some of the disulfide linkages may be cleaved to form a plurality of dissociated species (e.g., which are not immobilized with respect to the substrate). Techniques for formation of a disulfide bond in a component of the immobilized complex (e.g., as part of the capture component, the analyte molecule, and/or a binding ligand(s)) are known to those of ordinary skill in the art. A non-limiting reagent that may be used for the formation of a disulfide linkage is pyridyl disulfide-containing heterobifunctionals (e.g., SDPD, N-succinimidyl-pyridyldithiopropionate and SMPT, 4-succinimidyloxycarbonyl-α-methyl-α-(2-pyridyldithio)toluene). Disulfide bonds may be cleaved, for example, through hydrogenolysis by a reducing agent (e.g., beta-mercaptoethanol, dithiothreitol, dithioerythritol, cysteine, tris(2-carboxytheyl)phosphine, and/or butanethiol) or through a disulfide interchange process with a compound containing one or more free sulfhydryls.

A disulfide linkage may be cleaved in certain embodiments by exposing the linkage to a reducing agent. In some cases, the reduction will yield unconjugated molecules, one or both of which may contain a portion of the disulfide linkage, and in some cases, a free sulfhydryl (e.g., —SH) will be formed on one or both the ends of the cleaved linkage. A non-limiting example of a how a disulfide linkage may be cleaved is shown in Equation 1:

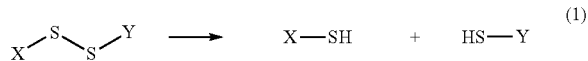

(1)

wherein X and Y are components of the immobilized complex relative to the disulfide linkage. A chemical reducing agent reacts with the disulfide bonds to generate two free sulfhydryl groups per original disulfide bond.

In a particular embodiment of the present invention, a binding ligand may comprise a disulfide linkage. The disulfide group may be cleaved by exposure of an immobilized complex comprising the binding ligand to beta-mercaptoethanol. In other embodiments, a capture component may comprise a disulfide linkage that may be cleaved by exposure to beta-mercaptoethanol and/or another reducing agent.

In other embodiments, the cleavable linkage may be a diol or a glycol. A diol or glycol linkage may be incorporated into a portion of the immobilized complex using methods that are known to those skilled in the art (e.g., inclusion of a tartaric acid residue). In some cases, the glycol or diol linkage may be cleaved by oxidation. For example, the immobilized complex comprising a diol or a glycol cleavable linkage may be exposed to a reagent such as sodium periodate or palladium acetate ($Pd(OAc)_2$), and the linkage may be cleaved to form aldehydes. A non-limiting example of the cleavage of a glycol linkage is shown in Equation 2:

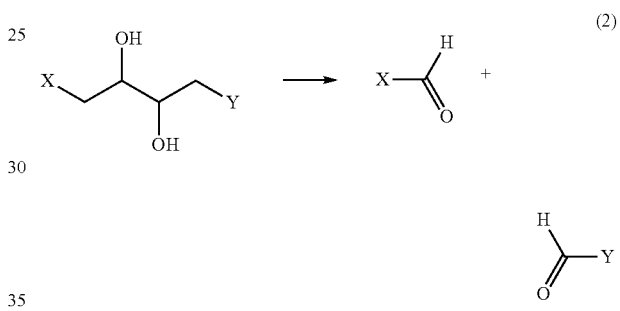

(2)

wherein X and Y are components of the immobilized complex relative to the glycol linkage.

In yet other embodiments, the cleavable linkage may be a diazo bond. A diazo bond may be incorporated into a portion of the immobilized complexes using methods that are known to those skilled in the art (e.g., coupling between an arendiazonium cation and a phenol). For non-limiting examples see March, J.; *Advanced Organic Chemistry*, New York, John Wiley and Sons, 1992, pages 591-592, 638, etc. A diazo linkage may be cleaved upon exposure to a chemical dissociating agent such as dithionite, zinc metal, and sodium hydrosulfite ($Na_2S_2O_4$) to form primary amines. A non-limiting example of the cleavage of a diazo linkage is shown in Equation 3:

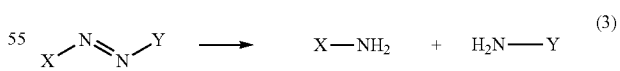

(3)

wherein X and Y are components of the immobilized complex relative to the diazo linkage.

In yet other embodiments, the linkage may be an ester or a thioester. An ester or a thioester linkage may be cleaved upon exposure to a nucleophile, such as hydroxylamine. The cleavage of an ester with hydroxylamine may result in the formation of an amide derivative on one side of the cleaved crosslinker and a hydroxyl group on the other side, as shown in Equation 4.

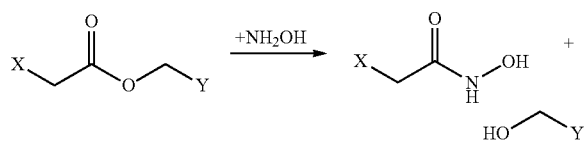

(4)

wherein X and Y are the parts of the immobilized complex relative to the ester linkage.

In still yet other embodiments, the linkage may be a sulfone linkage. Sulfone linkages that may be incorporated into a complex include 4,4'-difluoro-3,3'-dinitrodiphenyl sulfone (DFDNPS) and bis(2-[succinimidooxycarbonyloxy]ethyl) sulfone (BSOCOES). The sulfone linkage may be cleaved by hydrolysis under basic conditions, such as in the presence of sodium phosphate. The cleavage of a sulfone group is shown in Equation 5:

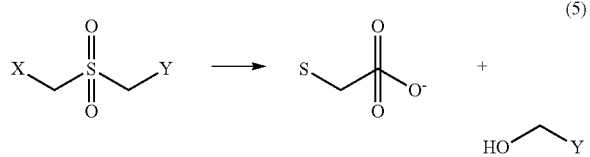

(5)

wherein X and Y are components of the immobilized complex relative to the sulfone linkage.

In other cases, the cleavable linkage may be an enzymatically cleavable linkage. For example, a protease may be used to cleave a cleavable functional group having a suitable recognition sequence for the protease. Particularly useful proteases are endopeptidases such as factor Xa, tobacco etch virus (TEV) protease, trypsin, chymotrypsin, *Staphylococcus aureus* protease, submaxillaris protease, and others. The protease can be selected based on the incorporation of a particular cleavable recognition sequence as a functional group. Other considerations for selecting a protease include the presence or absence of a recognition sequence in the molecule being captured and released.

In yet other cases, the cleavable linkage may be a pH-cleavable linkage and comprise pH-labile bonds. For example, ketals may be labile (e.g., cleaved) in acidic environments (e.g., pH less than 7) and form a diol and a ketone. As another example, acetals may be labile (e.g., cleaved) in acidic environments (e.g., pH less than 7) and form a diol and an aldehyde. As yet another example, imines or iminiums may be labile in acidic environments (e.g., pH less than 7) and form an amine and an aldehyde or a ketone, respectively. In other instances, a cleavable linkage may be cleaved in basic conditions (e.g., sulfone linkage).

In some embodiments, a method of the present invention may comprise releasing a plurality of molecules or particles from the first substrate. The plurality of molecules or particles released from the first substrate may comprise at least a portion of an analyte molecule or particle captured on the first substrate or may be free of any portion of an analyte molecule or particle captured on the first substrate. A plurality of molecules or particles may be released by exposing the substrate to electromagnetic radiation (e.g., ultraviolet light). As another example, a plurality of molecules or particles may be released by exposing the substrate to a chemical dissociating agent (e.g., beta-mercaptoethanol). As yet another example, a plurality of molecules or particles may be released by physical manipulations (e.g., scraping the substrate, agitation, etc.).

Detection

The plurality of dissociated species may be detected and/or quantified, and the detection and/or quantification may be related to the presence and, optionally, quantity and/or concentration of analyte molecules/particles in the sample being tested. In some embodiments, the plurality of dissociated species may be detected and/or quantified by partitioning the plurality of dissociated species across a plurality of reaction vessels (e.g., in an array). In certain embodiments, the partitioning may occur such that at least some (e.g., a statistically significant fraction) of the reaction vessels comprise at least one or, in certain cases, one dissociated species and at least some (e.g., a statistically significant fraction) of the reaction vessel comprises no dissociated species. In some cases, a detector may be configured to detect dissociated species in or on a substrate (e.g., an array of reaction vessels).

In some embodiments, when a first substrate is used to capture a plurality of analyte molecules and/or particles and a second substrate is used to detect a plurality of dissociated species, the number of dissociated species detected on or within the second substrate may be directly proportional to the number of dissociated species released from the second substrate. In other embodiments, the number of dissociated species detected on or within the second substrate may be approximately equal to, less than about one half, less than about one quarter, less than about one tenth, less than about one hundredth, less than about one thousandth, less than about one ten-thousandth, or the like, of the number of the plurality of dissociated species dissociated from the first substrate.

In some embodiments, the number of dissociated species detected is no greater than the number of dissociated species released and/or the number of dissociated species is no greater than the number of analyte molecules or particles associated with a first substrate. For example, the number of dissociated species detected (e.g., on a second substrate) may be approximately equal to, no greater than about three quarters of, no greater than about one half of, no greater than about one quarter of, no greater than about one tenth of, no greater than about one hundredth of, no greater than about one thousandth of, no greater than about ten thousandth of, or no greater than about one hundred thousandth of, the number of analyte molecules or particles associated (e.g., captured) with a first substrate and/or the number of dissociated species released (e.g., from a first substrate).

The dissociated species may be detected and/or quantified directly or indirectly. In the case or direct detection, the dissociated species itself comprises a molecule or moiety that may be directly interrogated and detected, for example, a fluorophore. A reaction vessel that comprises such a dissociated species will therefore emit a signal upon interrogation of the reaction vessel.

The indirect approach can include, for example, exposing dissociated species comprising at least one precursor labeling agent molecule to a suitable converting agent to produce a detectable labeling agent molecule. In other embodiments, the dissociated species may comprise a converting agent and may be exposed within the reaction vessel to a precursor labeling agent molecule to produce a detectable labeling agent molecule. In some cases, at least one precursor labeling agent molecule is converted to a labeling agent molecule when contained in a reaction vessel comprising a dissociated species. The presence or absence of a dissociated species in a reaction vessel may then be determined by determining the presence or absence of a labeling agent molecule in the reaction vessel. For example, the dissociated species may comprise an enzymatic component and the precursor labeling agent molecule may be a chromogenic, fluorogenic, or chemiluminescent enzymatic precursor labeling agent molecule. Exposure of the precursor labeling agent molecule to the enzymatic component may convert the precursor labeling agent molecule to a chromogenic, fluorogenic, of chemiluminescent labeling agent molecule that may be detected. In another instances, the indirect approach can include, for example, the situation where the dissociated species does not have intrinsic activity to convert a precursor labeling agent molecule to a labeling agent molecule and is not detectable itself. Therefore, the dissociated species may be exposed to at least one dissociated species binding ligand which may associate with the dissociated species, thus forming a complex comprising the dissociated species and the dissociated species binding ligand. The dissociated species binding ligand may comprise a component that is able to convert a precursor labeling agent molecule into a labeling agent molecule or may comprise a precursor labeling agent molecule able to be converted by exposure to a converting agent. Thereafter, the presence of the labeling agent molecule can be determined to determine whether a dissociated species is present in a reaction vessel. It is to be understood that a variety of dissociated species, dissociated species binding ligands, and precursor labeling agent molecules, as will be discussed in more detail below, may be used in the practice of the invention. To the extent that a dissociated species comprises an enzymatic component, enzymatic precursor labeling agent molecules can be added to the reaction vessel whereupon the enzymatic component converts the precursor labeling agent molecule into a chromogenic, fluorogenic, or chemiluminescent labeling agent molecule and permits the detection of the dissociated species.

Figure 15A:
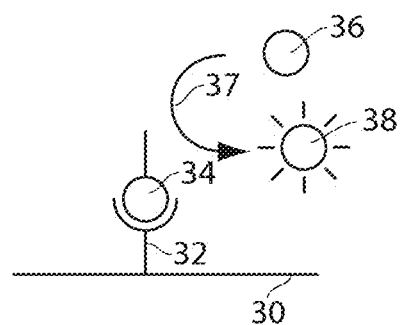
FIG. 15A is a schematic flow diagram depicting a method of indirectly detecting a dissociated species and/or a molecule or particle released from a substrate, according to some embodiments.
Figure 15B:
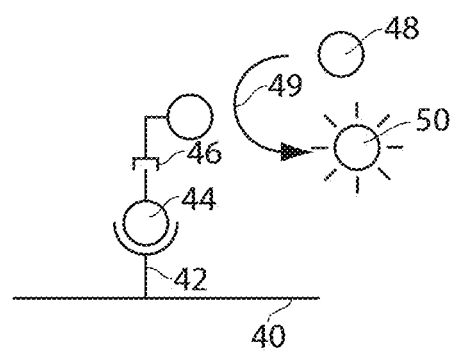
FIG. 15B is a schematic flow diagram depicting a method of indirectly detecting a dissociated species and/or a molecule or particle released from a substrate, according to some embodiments.

Two non-limiting examples of indirect detection of a dissociated species are illustrated in FIGS. 15A and 15B. In FIG. 15A, a reaction vessel 30 is provided which comprises a detection capture component 32. Dissociated species 34 is associated with detection capture component 34. The reaction vessel is exposed to precursor labeling agent molecule 36, which upon exposure to dissociated species 34 carrying a converting agent, converts to a labeling agent molecule 38, as indicated by arrow 37. As another example, in FIG. 15B, a reaction vessel 40 is provided which comprises a detection capture component 42. Dissociated species 44 is associated with the detection capture component 42. A dissociated species binding ligand 46 is provided which associates with dissociated species 44. The reaction vessels is exposed to precursor labeling agent molecule 48 which upon exposure to dissociated species binding ligand 44 converts to labeling agent molecule 50, as indicated by arrow 49.

In some embodiments, a dissociated species may comprise an enzymatic component (e.g., from a binding ligand). In this instance, the precursor labeling agent molecule may be an enzymatic label, for example, a chromogenic, fluorogenic, or chemiluminescent enzymatic precursor labeling agent molecule, that upon contact with the enzymatic component, converts to a labeling agent molecule. In some cases, the chromogenic, fluorogenic, or chemiluminescent enzymatic precursor labeling agent molecule is provided in an amount sufficient to contact every dissociated species which was partitioned across a plurality of reaction vessels. In some cases, the enzymatic component may comprise beta-galactosidase or horseradish peroxidase.

As will be understood by those of ordinary skill in the art, chromogenic, fluorogenic, or chemiluminescent enzymatic precursor labeling agent molecules may be selected for conversion by many different enzymes. Thus, any known chromogenic, fluorogenic, or chemiluminescent enzyme precursor labeling agent molecule capable of producing a labeling agent molecule in a reaction with a particular enzyme can potentially be used in the present invention as the precursor labeling agent molecule in embodiments where the dissociated species comprises an enzymatic component (or a dissociated species binding ligand comprises an enzymatic component). For example, many chromogenic, fluorogenic, or chemiluminescent precursor labeling agent molecules suitable for use an enzymatic precursor labeling agent molecule are disclosed in *The Handbook—A Guide to Fluorescent Probes and Labeling Technologies*, Tenth Ed., Chapter 10.

In some embodiments, the plurality of reaction vessels may additionally comprise at least one dissociated species capture component. A "dissociated species capture component" is a capture component that specifically binds to or otherwise captures a dissociated species, such that the dissociated species is immobilized during the assay. Generally, the dissociated species capture component allows the attachment of a dissociated species to a solid support (that is, the surface of a microwell, a sealing component or a nanoparticle) for the purposes of detection, quantification, or other analysis. In some cases, a method of the present invention will comprise the step of immobilizing at least one of the plurality of dissociated species with respect to the at least one dissociated species capture component.

In some embodiments, at least some of the plurality of dissociated species may be immobilized with respect to at least one particle comprising at least one binding partner for the dissociated species, thereby forming a plurality of complexes. A plurality of particles comprising a binding partner may be provided, in some cases, such that one or zero dissociated species released from the substrate associates with each binding partner of at least a fraction of the plurality of particles comprising a binding partner. The particles may have an average diameter of less than about 100 um, less than about 50 um, less than about 10 um, less than about 1 um, less than about 500 nm, less than about 100 nm, less than about 10 nm, less than about 1, or the like. In some cases, the particles may be provided such that there is greater than about 10, greater than about 100, greater than about 1000, greater than about 10,000, greater than about 100,000, greater than about 1,000,000, or the like, particles provided for every dissociated species released from the substrate. In some such embodiments, the plurality of dissociated species may be immobilized with respect to a plurality of particles prior to partitioning across a plurality of reaction vessels. In certain embodiments, the plurality of dissociated species may be exposed to a plurality of particles such that either one or no dissociated species are immobilized with respect to a single particle. The particles may comprise a plurality of binding partners (e.g., biotin) with respect to which a dissociated species may be immobilized, thereby forming a plurality of particle-containing complexes. The particle-containing complexes may be partitioned across a plurality of reaction vessels such that at least some (e.g., a statistically significant fraction) of the plurality of reaction vessels contain zero particle-containing complexes and at least some (e.g., a statistically significant fraction) of the plurality of reaction vessels contain only one or at least one particle-containing complex. The reaction vessels which comprise a particle-containing complex may then be determined, and the methods describe herein may be used to detect and/or quantify the dissociated species and analyte molecules. For example, the number or fraction of the plurality of reaction vessels that contain a particle-containing complex may be related to a measure of the concentration of analyte molecules or particles in the fluid sample. The particle-containing complexes may be detected directly or indirectly using methods as discussed herein (e.g., electromagnetic radiation, microscopy, etc.). Each reaction vessel may comprise at least about 10 particles, at least about 100 particles, at least about 500 particles, at least about 1000 particles, at least about 5000 particles, at least about 10000 particles, or the like, wherein in some reaction vessels, at least one particle may comprise a complex (e.g., a particle-containing complex). Each reaction vessel may comprise approximately the same or differing number of particles as the reaction vessels which it is adjacent to.

Figure 16:
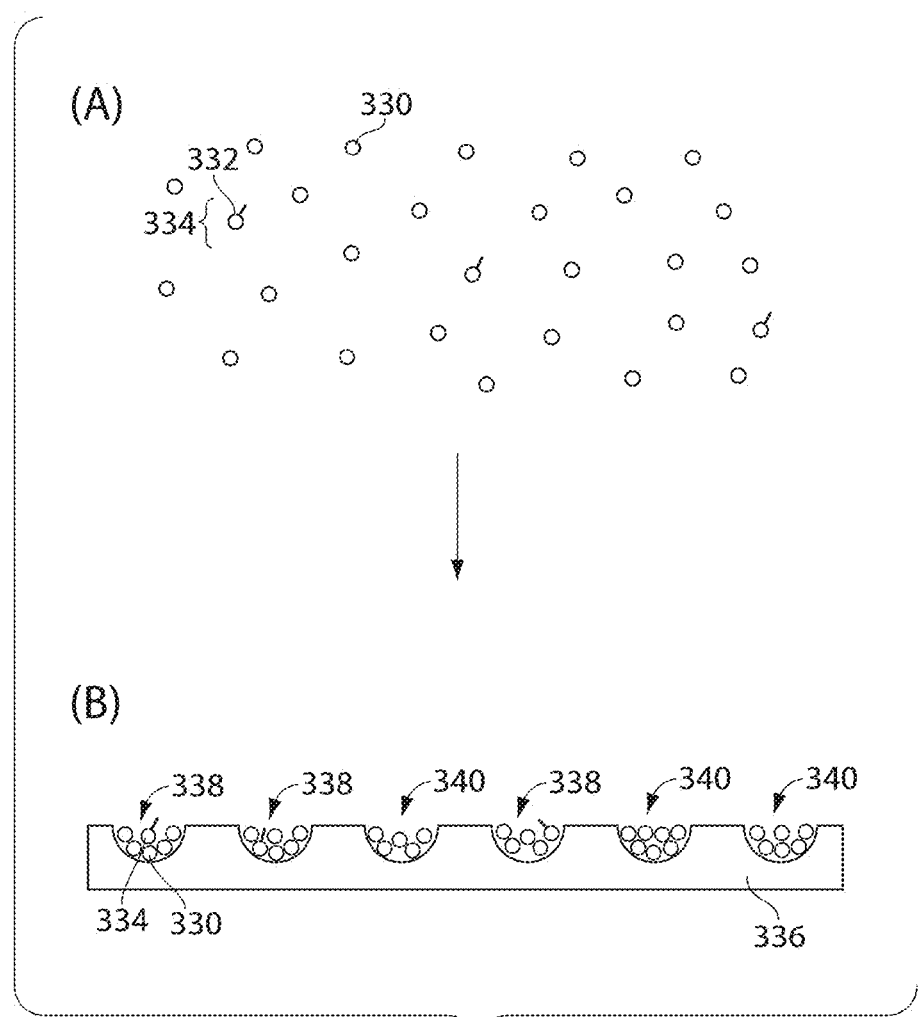
FIG. 16 is a schematic flow diagram depicting steps (A-B) of one embodiment of one method of the present invention in which dissociated species are immobilized with respect to particles prior to partitioning across a plurality of reaction vessels.

A non-limiting embodiment of the above assay method is depicted in FIG. 16. A plurality of particles 330 are exposed to a plurality of dissociated species such that at least some of each of the plurality of dissociated species 332 are immobilized with respect to a particles 330 to form a plurality of dissociated species in the form of particle-containing complexes 334 (step (A)). The plurality of particles and particle-containing complexes may be partitioned across a plurality of reaction vessels 336 such that at least some of the plurality of reaction vessels contain only one or at least one particle-containing complex 338 and at least some of the plurality of reaction vessels will contain zero particle-containing complexes 340 (step (B)).

In some embodiments, at least a fraction of the number of dissociated species may be detected substantially simultaneously. "Substantially simultaneously" when used in conjunction with detection, as used herein, refers to detection of the species/molecules/particles of interest at approximately the same time, as opposed to sequentially detected. A plurality of species/molecules/particles may be detected substantially simultaneously using various techniques, including optical techniques (e.g., CCD detector). In some embodiments involving substantially simultaneous detection, each of the detected species/molecules/particles (e.g., dissociated species) is spatially separated with respect to the other detected species/molecules/particles (e.g., dissociated species) during detection, such that detection is able to resolve individual dissociated species of the plurality of dissociated species detected. For example, resolving individual molecules/particles of a plurality of molecules/particles that are partitioned across a plurality of reaction vessels such that each reaction vessel contains zero or only one species/molecule/particle involves detecting molecules/particles that are spatially separated. In some cases, at least about 80%, at least about 85%, at least about 90%, at least about 95%, at least about 96%, at least about 97%, at least about 98%, at least about 99%, at least about 99.5% of all species/molecules/particles are spatially separated with respect to other species/molecules/particles during detection.

Detection Methods

In some embodiments, in the systems/methods in which the species to be detected are partitioned across a plurality of reaction vessels, the reaction vessels may be interrogated using a variety of techniques, including techniques known to those of ordinary skill in the art.

In a specific embodiment of the present invention, reaction vessels are optically interrogated. The reaction vessels exhibiting changes in their optical signature may be identified by a conventional optical train and optical detection system. Depending on the detected species (e.g., labeling agent molecules, dissociated species, particles, etc.) and the operative wavelengths, optical filters designed for a particular wavelength may be employed for optical interrogation of the reaction vessels. In one embodiment, the plurality of reaction vessels of the present invention is formed directly as part of a fiber optic bundle.

According to one embodiment, the array of reaction vessels of the present invention can be used in conjunction with an optical detection system such as the system described in U.S. Publication No. 20030027126. For example, according to one embodiment, the array of reaction vessels of the present invention is formed in one end of a fiber optic assembly comprising a fiber optic bundle constructed of clad fibers so that light does not mix between fibers.

Figure 17A:
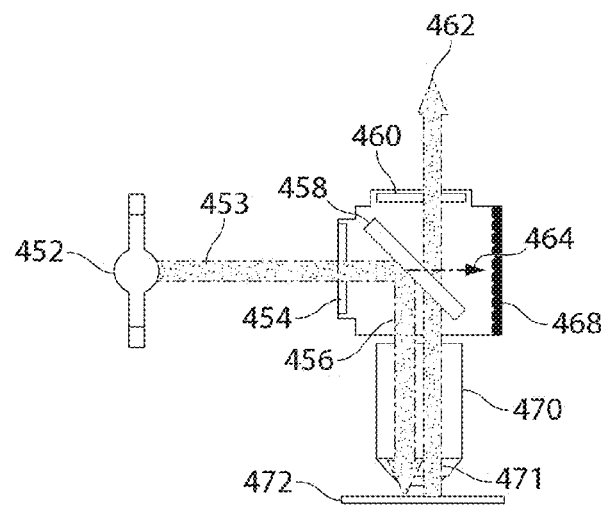
FIGS. 17A and 17B show non-limiting examples of a system employing an optical detection system of the present invention according to some embodiments.

FIG. 17A shows a non-limiting example of a system of the present invention according to some embodiments. The system comprises a light source 252, excitation filter 454, dichromatic mirror 458, emission filter 460, objective 470, and second substrate 472. Light 453 given off from light source 452 is passed through excitation filter 454. The light reflects off dichromatic mirror 458, passes through objective 470 and shines on second substrate 472. In some cases, stray light 464 may be reduced by a stray light reducing function 468, such as an iris or aperture. Light 471 emitted from the second substrate passes through objective 472 and emission filter 460 and is observed. The system may comprise additional components (e.g., additional filters, mirrors, magnification devices, etc.), as needed for particular applications, as would be understood by those of ordinary skill in the art.

The optical detection system of U.S. Publication No. 20030027126 operates as follows. Light returning from the distal end of the fiber optic bundle is passed by the attachment to a magnification changer which enables adjustment of the image size of the fiber's proximal or distal end. Light passing through the magnification changer is then shuttered and filtered by a second wheel. The light then is imaged on a charge coupled device (CCD) camera. A computer executes imaging processing software to process the information from the CCD camera and also optionally controls the first and second shutter and filter wheels. As depicted in U.S. Publication No. 20030027126, the proximal end of the bundle is received by a z-translation stage and x-y micropositioner.

Figure 18:
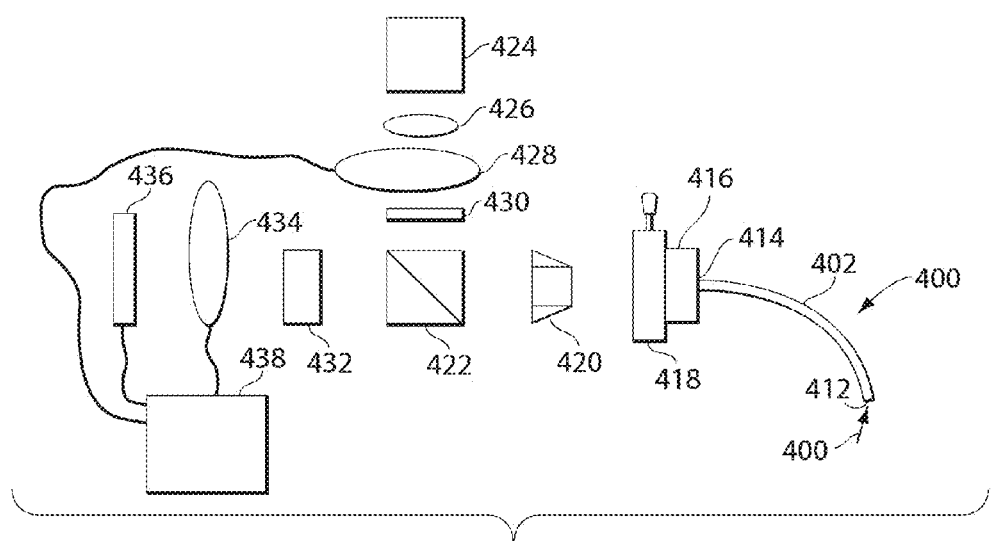
FIG. 18 is a schematic block diagram showing a system employing a fiber optic assembly with an optical detection system according to an embodiment of the invention.

For example, FIG. 18 shows a schematic block diagram of a system employing a fiber optic assembly 400 with an optical detection system. The fiber optic assembly 400 comprises a fiber optic bundle or array 402 that is constructed from clad fibers so that light does not mix between fibers. An array or system, 400 is attached to the bundle's distal end 412, with the proximal end 414 being received by a z-translation stage 416 and x-y micropositioner 418. These two components act in concert to properly position the proximal end 414 of the bundle 402 for a microscope objective lens 420. Light collected by the objective lens 420 is passed to a reflected light fluorescence attachment with three pointer cube slider 422. The attachment 422 allows insertion of light from a 75 Waft Xe lamp 424 through the objective lens 420 to be coupled into the fiber bundle 402. The light from the source 424 is condensed by condensing lens 426, then filtered and/or shuttered by filter and shutter wheel 428, and subsequently passes through a ND filter slide 430. Light returning from the distal end 412 of the bundle 402 is passed by the attachment 422 to a magnification changer 432 which enables adjustment of the image size of the fiber's proximal or distal end. Light passing through the magnification changer 432 is then shuttered and filtered by a second wheel 434. The light is then imaged on a charge coupled device (CCD) camera 436. A computer 438 executes imaging processing software to process the information from the CCD camera 436 and also possibly control the first and second shutter and filter wheels 428, 434.

The array of reaction vessels of the present invention may be integral with or attached to the distal end of the fiber optic bundle using a variety of compatible processes. In some cases, microwells are formed at the center of each individual fiber of the fiber optic bundle and the microwells may or may not be sealed. Each optical fiber of the fiber optic bundle may convey light from the single microwell formed at the center of the fiber's distal end. This feature enables the interrogation of the optical signature of individual reaction vessels to identify reactions/contents in each microwell. Consequently, by imaging the end of the bundle onto the CCD array, the optical signatures of the reaction vessels are individually interrogatable and may be detected substantially simultaneously.

As discussed above, in some embodiments of the present invention, the plurality of reaction vessels may be sealed, for example, through the mating of the second substrate and a sealing component. In some cases, the sealing of the reaction vessels may be such that the contents of each reaction vessel cannot escape the reaction vessel. In some cases, the reaction vessels may be sealed after the addition of a dissociated species and, optionally, a precursor labeling agent molecule to facilitate detection of the dissociated species. For embodiments employing precursor labeling agent molecules, by sealing the contents in some or each reaction vessel, a reaction to produce the detectable labeling agent molecule can proceed within the sealed reaction vessels, thereby producing a detectable amount of a labeling agent molecule that is retained in the reaction vessel for detection purposes.

Quantification

According to some embodiments of the present invention, the methods, systems, and/or devices may be used to determine the presence and/or a measure of the concentration of a plurality of analyte molecules (or particles) in a fluid sample based at least in part on detecting and/or quantifying at least some of a plurality of dissociated species (or particles or molecules released from a substrate on which the analyte molecules/particles are captured). In some cases, there is a correlation between the percentage of reaction vessels containing one or more dissociated species and the quantity/concentration of analyte molecules in the fluid sample. Thus, the quantification method of the present invention may allow for a determination of a measure of the concentration of analyte molecules in a fluid sample based on the percentage of reaction vessels that contain a dissociated species released from a substrate. In some cases, the concentration of the analyte molecules in a fluid sample will be linearly proportional to the quantification of the dissociated species. In other cases, the measure of concentration of the analyte molecules in a fluid sample will be related to the determination and/or quantification of the dissociated species by a non-linear relationship. In some embodiments, the measure of the concentration of analyte molecules in a fluid sample will be determined using a calibration curve. Methods to determine a measure of the concentration of analyte molecules in a fluid sample are discussed more below.

Certain embodiments of present invention are distinguished by the ability to detect and/or quantify low numbers/concentrations of dissociated species and may be well suited to determine a measure of the concentration of analyte molecules in a fluid sample containing very low concentrations of the analyte. It is currently believed that this ability may be achieved by spatially isolating individual or small numbers of dissociated species, for example, as partitioned across an array of reaction vessels, and then detecting their presence in the reaction vessels. The presence of a dissociated species in a reaction vessel can be counted in a binary fashion (e.g., zero when a dissociated species is absent; one when a dissociated species is present), for example by determining the presence of a detectable molecule or particle in a reaction vessel that contains at least one dissociated species.

In some embodiments, the plurality of dissociated species may be partitioned such that at least some of the reaction vessels contain no dissociates species and at least some of reaction vessels contain at least one or, in certain cases, only one dissociates species. For example, in some cases, the plurality of dissociates species may be partitioned such that a statistically significant fraction of the reaction vessels contain no dissociates species and a statistically significant fraction of reaction vessels contain at least one dissociates species. In other cases, the plurality of dissociated species may be partitioned such that a statistically significant fraction of the reaction vessels contain no dissociated species and a statistically significant fraction of reaction vessels contain only one dissociated species. In either case, the number of the plurality of reaction vessels and/or fraction of the plurality of reaction vessels that contain or do not contain a dissociated species may be determined. The number and/or fraction of the plurality of reaction vessels that contain a dissociated species can be related to the concentration of analyte molecules or particles in the sample. In some embodiments, a measure of the concentration of analyte molecules or particles in the fluid sample is determined based on the determination of the number and/or fraction of the plurality of reaction vessels that contain a dissociated species. In certain such embodiments, the measure of the concentration of the analyte molecules or particles in the fluid sample is determined at least in part by comparison of a measured parameter to a calibration standard and/or by a Poisson and/or Gaussian distribution analysis of the number or fraction of the plurality of reaction vessels that contain a dissociated species, as discussed more below.

A "statistically significant fraction" of the reaction vessels that contain a specified quantity of dissociated species is defined as the minimum number of reaction vessels that can be reproducibly determined to contain a dissociates species with a particular system of detection (i.e., substantially similar results are obtained for multiple essentially identical fluid samples comprising the dissociates species) and that is above the background noise (e.g., non-specific binding) that is determined when carrying out the assay with a sample that does not contain any analyte molecules or particles, divided by the total number of reaction vessels. The statistically significant fraction may be experimentally determined for a certain assay type and equipment set up (e.g., for each dissociates species determined, each binding ligand, etc). In certain embodiments, the percentage of reaction vessels (e.g., the statistically significant fraction) which comprises only one or at least one dissociates species is less than about 10%, less than about 5%, less than about 1%, less than about 0.5%, or less than about 0.1% of the total reaction vessels. In some cases, the percentage of reaction vessels which do not contain an dissociates species is at least about 20%, at least about 40%, at least about 50%, at least about 60%, at least about 70%, at least about 75%, at least about 80%, at least about 90%, or at least about 95%, at least about 99%, at least about 99.5%, at least about 99.9%, or greater, of the total number of reaction vessels.

In some embodiments, a measure of the concentration of analyte molecules or particles in the fluid sample may be determined at least in part by comparison of a measured parameter to a calibration standard. For example, the fraction of reaction vessels that comprise a dissociated species may be calibrated against a calibration curve to determine a measure of the concentration of the analyte molecule in the fluid sample. The calibration curve may be produced by completing the assay with a plurality of standardized samples of known concentration under the conditions used to analyze the test samples. A reading may be taken for the signal related to the detection/quantification of the dissociated species for each standardized sample, therefore allowing for the formation of a calibration curve relating the detection of the dissociated species with a known concentration of the analyte molecule. The assay may then be completed on a sample comprising the analyte molecule in an unknown concentration, and the detection of the dissociated species from this assay may be plotted on the calibration curve, therefore determining a measure of the concentration of the analyte molecule in the fluid sample.

Figure 19:
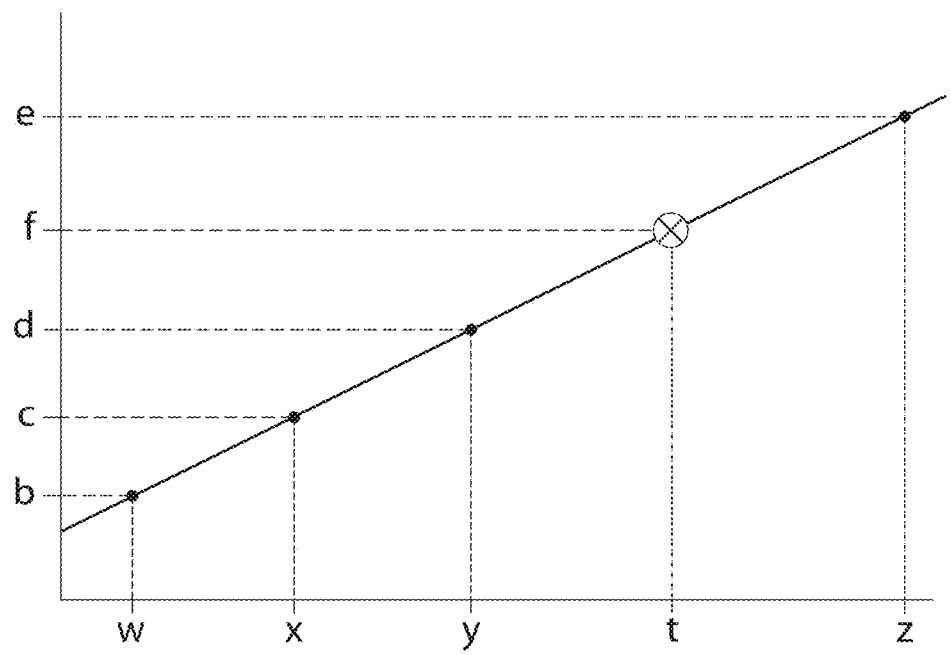
FIG. 19 shows a graph of a schematic calibration curve of a form that may be used to determine the concentration of an analyte molecule or particle in a fluid sample, according to some embodiments of the present invention.

In one exemplary calibration, four standardized fluid samples comprising an analyte molecule in varying concentration (w, x, y, and z) are provided. An assay (e.g., immobilizing the analyte molecules, dissociating a plurality of dissociated species, detecting at least a portion of the dissociated species) is carried out for each sample, and a value corresponding to the detection of the dissociated species (b, c, d, and e) may be determined A plot is produced of the values related to detection of the dissociated species (b, c, d, and e) versus the concentration of the standardized samples (w, x, y, and z), as depicted in FIG. 19. The assay may be then be carried out under substantially identical conditions on a fluid sample comprising an analyte molecule of unknown concentration t, wherein the resulting value related to detection of the dissociated species is f. This value may be plotted on the graph and a measure of the unknown concentration of the target analyte in the fluid sample may be interpolated from the values of the standardized samples. In some cases, the calibration curve may have a limit of detection, wherein the limit of detection is the lowest concentration of analyte molecules in a fluid sample that may be accurately determined. In some cases, the $r^2$ value of the calibration curve may be greater than about 0.5, greater than about 0.75, greater than about 0.8, greater than about 0.9, greater than about 0.95, greater than about 0.97, greater than about 0.98, greater than about 0.99, greater than about 0.9999, or about 1.

In some embodiments, the concentration of analyte molecules in the fluid sample may be determined by comparison to a calibration curve using a system comprising a computer. The computer may comprise software that may use the data collected to produce the calibration curve and/or a reading of the measured concentration of the analyte molecules in the fluid sample. For example, a fluorescence image of an array comprising the dissociated species partitioned across the array (e.g., second substrate) may be collected and analyzed using image analysis software (e.g., IP Lab, BD Biosciences). The analysis software may automatically calculate the number of reaction vessels that have fluorescence intensity over the background intensity and produce a number indicative of the total number of reaction vessel which comprises a fluorescent intensity over the background intensity (e.g., a number that correlates to the number of reaction vessels which comprise a dissociated species). The number of reaction vessels which comprise fluorescence intensity over the background intensity may be divided by the total number of reaction vessels to give a number correlating to the fraction of reaction vessels which comprise a dissociated species. The active well fraction may be compared to a calibration curve to determine a measure of the concentration of analyte molecules in the fluid sample.

In some cases, the number of dissociated species that are detected may or may not be approximately equal to the number of analyte molecules in the fluid sample. For example, the ratio of analyte molecules to dissociated species that are detected may be about 1:1, about 2:1, about 5:1, about 10:1, about 100:1, about 1000:1, about 10000:1, or the like. In some cases, the ratio is greater than about 1:1, greater than about 10:1, great than about 100:1, greater than about 1000:1, greater than about 10000:1, or the like. Additionally, the number of dissociated species that are detected may or may not be approximately equal to the total number of dissociated species released from the substrate. For example, the ratio of dissociated species dissociated to dissociated species that are detected may be about 1:1, about 2:1, about 5:1, about 10:1, about 100:1, about 1000:1, about 10000:1, or the like. In some cases, the ratio is greater than about 1:1, greater than about 10:1, great than about 100:1, greater than about 1000:1, greater than about 10000:1, or the like. As another example, the number of molecules or particles detected on or within the second substrate is less than about one half, less than about one quarter, less than about one tenth, less than about one hundredth, less than about one thousandth, less than about one ten-thousandth, less than about one hundred-thousandth of the number of the plurality of molecules or particles released from the first substrate.

In some embodiments, the concentration of analyte molecules or particles in the fluid sample that may be substantially accurately determined is less than about 5000 fM, less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 0.5 fM, less than about 0.1 fM, or the like. In some embodiments, the concentration of analyte molecules or particles in the fluid sample that may be substantially accurately determined is between about 5000 fM and about 0.1 fM, between about 3000 fM and about 0.1 fM, between about 1000 fM and about 0.1 fM, between about 1000 fM and about 1 fM, between about 100 fM and about 1 fM, between about 100 fM and about 0.1 fM, or the like. The concentration of analyte molecules or particles in a fluid sample may be considered to be substantially accurately determined if the measured concentration of the analyte molecules or particles in the fluid sample is within about 10% of the actual (e.g., true) concentration of the analyte molecules or particles in the fluid sample. In certain embodiments, the measured concentration of the analyte molecules or particles in the fluid sample may be within about 5%, within about 4%, within about 3%, within about 2%, within about 1%, within about 0.5%, within about 0.4%, within about 0.3%, within about 0.2% or within about 0.1%, of the actual concentration of the analyte molecules or particles in the fluid sample. In some cases, the measure of the concentration determined differs from the true (e.g., actual) concentration by no greater than about 20%, no greater than about 15%, no greater than 10%, no greater than 5%, no greater than 4%, no greater than 3%, no greater than 2%, no greater than 1%, or no greater than 0.5%. The accuracy of the assay method may be determined, in some embodiments, by determining the concentration of analyte molecules in a fluid sample of a known concentration using the selected assay method.

Without being limited by theory, the quantification method is believed to be driven in part by the fact that the number and volume of reaction vessels employed govern the dynamic range of concentrations that can be determined. That is, based on the number and volume of the reaction vessels in an array of the present invention, an estimate can be made of the range of concentrations of detected molecules in the solution partitioned across the vessels that allows for a measure of the concentration to be determined using certain methods of the present invention.

For example, for an array comprising approximately $2.4 \times 10^5$ reaction vessels, each having a volume of approximately 50 fL, a solution having a concentration of approximately $4 \times 10^{-11}$ M dissociated species in a fluid sample will yield, on average, one dissociated species per reaction vessel. However, it is important to note that distributing a fluid sample having a dissociated species concentration within the appropriate range into an array of reaction vessels will not result in the distribution of exactly one dissociated species per each reaction vessel; statistically, some vessels will have multiple dissociated species while others will have no dissociated species. In the case where the ratio of vessels containing one or more dissociated species to the number of vessels containing no dissociated species is high, the data may be fit to a Gaussian distribution. As the ratio of reaction vessels containing a dissociated species to the number of vessels containing no dissociated species approaches zero, the Poisson distribution may be applied to the data. This limiting distribution may be used to calculate the probability of rare events occurring in a large number of trials. For example, based on Poisson statistics, for a concentration of approximately $4 \times 10^{-11}$ M, a distribution between zero and five dissociated species per container is predicted, with the most probable values being zero and one.

Equation 1 can be used to determine the probability of observing events based on the expected average number of events per trial, μ:

$$P_\mu(v) = e^{-\mu}(\mu^v/v!) \qquad \text{Equation 1}$$

where v is the number of events observed (e.g., the number of reaction vessels) and μ is the expected average number of events per trial (e.g., the average number of dissociated species per reaction vessel.

If the concentrations used are much less than approximately $4 \times 10^{-11}$ M, the expected average number of dissociated species per well becomes exceptionally low, the distribution is narrowed, and the probability of observing anything other than zero or one dissociated species per well is improbable in all experimental cases. At these low concentrations, the relationship between the percentage of active reaction vessels and the bulk dissociated species concentration is approximately linear. Thus, based on this knowledge, the array of the present invention can be used to determine the concentration of a dissociated species by a simple digital readout system (e.g., "counting" of active wells) as described herein in combination with a suitable calibration.

According to one embodiment, the quantification method of the present invention can be performed as follows. The method employs a digital readout system (also referred to as a "binary readout system") that involves first detecting the dissociated species in the plurality of reaction vessels by any detection method as described herein. The number of reaction vessels which comprise a dissociated species is then counted and a percentage of the total number of reaction vessels which comprise a dissociate species is calculated. That is, utilization of a yes or no response, in conjunction with the high-density array of reaction vessels, permits the digital readout of bulk concentrations of dissociated species. In some embodiments, this readout is accomplished by counting the number of reaction vessels containing at least one labeling agent molecule, with the resulting number of reaction vessels comprising a labeling agent molecule corresponding to the number of reaction vessels comprising a dissociated species. Given the large number of reaction vessels simultaneously interrogated in the array of the present invention, the ratio of dissociated species to reaction vessels may be at least about 1:100, at least about 1:1000, at least about 1:10,000, as the large number of reaction vessels provides a statistically significant signal even at this low ratio.

In some embodiments, without being limited by theory, it is believed that the quantification method of the present invention may only be limited by the number of individual reaction vessels that can be fabricated and interrogated. Thus, expanding the number of reaction vessels may increase both the dynamic range and the sensitivity of the assay. For example, increasing the number of reaction vessels by a factor of ten may decrease the ratio of dissociated species to reaction vessels by a factor of ten, thereby increasing the dynamic range and/or sensitivity of the assay. As mentioned above, in some embodiments, an array will comprise between about 1,000 and about 50,000, between about 1,000 and about 1,000,000, between about 1,000 and about 10,000, between about 10,000 and about 100,000, between about 100,000 and about 1,000,000, between about 1,000 and about 100,000, between about 50,000 and about 100,000, between about 20,000 and about 80,000, between about 30,000 and about 70,000, between about 40,000 and about 60,000, or about 50,000, or the like, reaction vessels.

In some embodiments, accuracy of this technique may be compromised above and below the thresholds of the dynamic range. For example, as the concentration of the dissociated species goes below the lower limit of the dynamic range, the number of dissociated species may be too low to observe a sufficient number of occupied wells. In such a situation, the number of reaction vessels could be decreased in order to make sure that at least some (e.g., a statistically significant number) of them are occupied by a dissociated species, the volume of the reaction vessels could be increased, and/or the sample tested could be concentrated. Results for extremely dilute concentrations may have large relative errors associated with them, due to the very small number of reaction vessels that are expected to show activity. In other cases, the ultimate upper limit to this technique may occur when 100% of the reaction vessels contain at least one dissociated species. At this limit, discrimination between two solutions of high dissociated species concentrations may not be feasible. In such a situation, to provide a more accurate test, a greater number of reaction vessels could be used, and/or the volume of each reaction vessel could be reduced, and/or the concentration of the sample could be reduced, e.g., through serial dilutions.

In the range where the fraction of reaction vessels containing at least one dissociated species is less than about 20%, the probability that any well contains two or more dissociated species is very small and the number of dissociated species closely matches the number of occupied reaction vessels. Between 20% occupied and 100% occupied, an increasing number of wells may contain more than one dissociated species, however Gaussian statistics can still be used to correlate occupancy fraction with concentration with reasonable accuracy until the occupancy fraction approaches 100%.

As alluded to above, the practical dynamic range of the method may be increased in several ways. In one approach, the sample and/or solution carrying the dissociated species may be diluted by a factor of 10 or more. Both the solution comprising the dissociated species and the diluted solution comprising the dissociated species may be assayed concurrently using the method of this invention. The dynamic ranges of the two assays may overlap, but be offset by the dilution factor, hence extending the dynamic range.

In some embodiments, multiple arrays of reaction vessels can be used, each array having reaction vessels with differing volumes, differing binding surface areas, or differing density and/or type of capture components on the binding surface. These configurations can be constructed as either distinct arrays or as one large array with distinct sub-arrays with varying characteristics. Since the probability of a dissociated species being detected in a given reaction vessel can be related to volume, binding surface area, and capture component density, the sub-arrays may be designed to provide different sensitivity ranges. Thus, with such configurations the effective range of the combined array may be extended.

In certain embodiments, after partitioning of the solution containing dissociated species across an array of reaction vessels, less than about 20% of the total number of the plurality of reaction vessels will contain at least one dissociated species (i.e. at least 80% of reaction vessels will be free of dissociated species). Under such circumstances, the number of reaction vessels containing at least one dissociated species will typically fall within the linear range of a Poisson distribution. In another embodiment, more than about 20% but less than about 60% of the total number of reaction vessels contains at least one dissociated species. Under such circumstances, the number of reaction vessels containing at least one dissociated species will typically fall within the non-linear range of a Poisson distribution. In another embodiment, more than about 60% but less than about 95% of the total number of reaction vessels contains at least one dissociated species. Under such circumstances, the number of reaction vessels containing at least one dissociated species will typically fall within the highly non-linear range of a Poisson distribution. In embodiments where greater than about 60% of the total number of reaction vessel contains at least one dissociated species, it may be desirable to decrease the percentage of reaction vessels which comprise at least one dissociated species (e.g., to less than about 20%). This may be accomplished using any suitable technique discussed herein, for example, diluting the fluid comprising the dissociated species and/or increasing the number of reaction vessels. In some cases, less than about 1%, less than about 5%, less than about 10%, less than about 20%, less than about 40%, less than about 60%, less than about 80%, less than about 90%, less than about 95%, or less than about 99% of the total number of the plurality of reaction vessels will contain at least one dissociated species. In certain embodiments, more than about 1%, more than about 5%, more than about 10%, more than about 20%, more than about 40%, more than about 60%, more than about 80%, more than about 90%, more than about 95%, or more than about 99% of the total number of the plurality of reaction vessels will contain no dissociated species.

In some embodiments, the invention provides a method of determining the concentration of the dissociated species in a fluid, the method comprising dividing the fluid containing the dissociated species into a plurality of second, smaller fluid samples of essentially equal volume so that at least some (e.g., a statistically significant fraction) of the second, smaller fluid samples contain either no dissociated species or a single dissociated species; determining the presence or absence of a dissociated species in each of the second, smaller fluid samples so as to identify the number of second, smaller fluid samples that contain a dissociated species; and determining the concentration of dissociated species in the fluid sample to be tested from the number of second, smaller samples that contain the dissociated species.

In certain embodiments, the present invention provides a method for determining the concentration of dissociated species in a fluid, the method comprising the partitioning at least a portion of the dissociated species in the fluid across a plurality of reaction vessels so that a statistically significant fraction of the reaction vessels contain a dissociated species and a statistically significant fraction of the reaction vessels contain no dissociated species; determining the presence or absence of a dissociated species in each reaction vessel to identify the number of reaction vessels that contain a dissociated species and/or to identify the number of reaction vessels that contain no dissociated species; and determining the concentration of dissociated species in the fluid at least in part from the number of reaction vessels that do or do not contain a dissociated species. In some embodiments, at least about 99%, at least about 95%, at least about 90%, at least about 80%, at least about 40%, at least about 20%, at least about 10% at least about 5%, at least about 1%, and the like of the reaction vessels do not contain a dissociated species. In some embodiments, the concentration of dissociated species in the fluid sample is determined at least in part using a calibration curve, a Poisson distribution analysis and/or a Gaussian distribution of the number of reaction vessels that contain at least one or one dissociates species. In other embodiments, the concentration of dissociated species in the fluid sample is determined at least in part by a Gaussian distribution analysis of the number of reaction vessels that contain a dissociated species.

In certain embodiments, the present invention provides a method of determining the concentration of dissociated species in a fluid, the method comprising exposing the fluid to a plurality of reaction vessels under conditions so that at least one dissociated species is captured in at least some of the reaction vessels, wherein each reaction vessel comprises a microwell and an optional sealing component and each reaction vessel defines a binding surface that has a capture component immobilized thereon; determining the presence or absence of a dissociated species in each reaction vessel so as to identify the number of reaction vessels that contain a dissociated species and/or the number of reaction vessels that do not contain a dissociated species; and determining the concentration of dissociated species in the fluid sample to be tested from the number of reaction vessels that contain and/or do not contain a dissociated species. In some embodiments, at least about 99%, at least about 95%, at least about 90%, at least about 80%, at least about 50%, at least about 20%, at least about 10% at least about 5%, at least about 1%, and the like of the reaction vessels contain either zero or one dissociated species. In some embodiments, the concentration of dissociated species in the fluid sample is determined at least in part using a calibration curve, a Poisson distribution analysis and/or a Gaussian distribution analysis of the number of reaction vessels that contain at least one or one dissociated species.

In certain embodiments, the present invention provides a method of determining the concentration of dissociated species in a fluid sample to be tested, the method comprising partitioning at least a portion of the dissociated species in the fluid into a plurality of reaction vessels, so that, for substantially all of the reaction vessels, each reaction vessel contains either no dissociated species or a single dissociated species; determining the presence or absence of a dissociated species in a plurality of reaction vessels to provide a fraction of the interrogated reaction vessels that contain a dissociated species; and determining the concentration of dissociated species in the fluid from the fraction of interrogated reaction vessels that contain a dissociated species.

In certain embodiments, the present invention provides a method of determining the concentration of dissociated species in a fluid, the method comprising partitioning the fluid into a plurality of second, smaller fluid samples of equal volume so that at least some of the second, smaller fluid samples contain either a single dissociated species or no dissociated species, (b) determining the presence or absence of a dissociated species in at least a subset of the second samples so as to identify the fraction of second samples in the subset that contain a dissociated species; and determining the concentration of dissociated species in the sample to be tested from the fraction of second samples of the subset that contain the dissociated species.

In some embodiments, a method of the present invention may be used for the detection of dissociated species in a fluid. For example, a method of detecting dissociated species in a fluid may comprise providing a fluid containing the dissociated species and an array, the array comprising a plurality of reaction vessels; contacting the array with the fluid such that the ratio of the number of dissociated species in the fluid contacted with the array to the number of reaction vessels in the array is less than 1:1; and determining the number of reaction vessels which contain a dissociated species. In some cases, the ratio of the number of dissociated species in the fluid contacted with the array to the number of reaction vessels in the array is less than about 1:5, less than about 1:10, less than about 1:100, or less than about 1:500.

In certain embodiments, a method of detecting dissociated species in a fluid according to the invention comprises providing a fluid and an array, the fluid comprising at least one dissociated species at a first concentration, the array comprising a plurality of reaction vessels; diluting the fluid to create a diluted fluid, wherein the diluted fluid comprises the dissociated species at a second concentration; contacting the array with the diluted fluid such that the ratio of dissociated species to the total number of reaction vessels in the array is between 1:1 and 1:500; and determining the number of vessels of said array which contain a dissociated species. In some cases, the ratio is less than about 1:1, less than about 1:5, less than about 1:10, less than about 1:100, or less than about 1:500.

The following examples are included to demonstrate various features of the invention. Those of ordinary skill in the art should, in light of the present disclosure, will appreciate that many changes can be made in the specific embodiments which are disclosed while still obtaining a like or similar result without departing from the scope of the invention as defined by the appended claims. Accordingly, the following examples are intended only to illustrate certain features of the present invention, but do not necessarily exemplify the full scope of the invention.

Example 1

This example outlines the materials used in the following examples. Optical fiber bundles were purchased from Schott North America, Inc (Southbridge, Mass.). In this example, the core glass comprised barium, lanthanum, boron, silica, and aluminum. The refractive index of the core was 1.694, and the density was 4.23 g/cc. The cladding glass comprised silica, lead, potassium, sodium, and aluminum. The refractive index of the clading was 1.559, and the density was 3.04 g/cc. The fiber array was a bundle of 50,000 individual fibers, each with a core diameter of 4.5 μm and the center-to-center spacing of the cores was 8 um.

Non-reinforced gloss silicone sheeting was obtained from Specialty Manufacturing Inc. (Saginaw, Mich.). Hydrochloric acid, 3-aminopropyl trimethoxysilane, anhydrous ethanol, molecular biology grade Tween®20, and N,N-Dimethyl formamide were all obtained from Sigma-Aldrich (Saint Louis, Mo.). Phosphate buffered saline, Blocker™ BSA (10%), Zeba Desalt spin columns, NHS-ss-biotin and NHS-LC-biotin were obtained from Pierce (Rockford, Ill.). Resorufin-beta-D-galactopyranoside, streptavidin-beta-galactosidase, and 1 um functionalized magnetic microspheres were purchased from Invitrogen (Carlsbad, Calif.). Monoclonal anti-human TNF-alpha capture antibody, polyclonal anti-human TNF-alpha detection antibody, and recombinant human TNF-alpha were purchased from R&D systems, Inc (Minneapolis, Minn.). The fiber polisher and polishing consumables were purchased from Allied High Tech Products, Inc. (Rancho Dominguez, Calif.).

Example 2

The example outlines the preparation of 1 um magnetic bead functionalized with TNF-alpha capture antibody. 20 uL of amine-reactive bead stock was washed three times in 0.1 M sodium borate coating buffer at pH 9.5 using a microtube magnetic separation device (BioMag® Tube Separator; Polysciences Inc., Warrington, Pa.). 500 ug TNF-alpha capture antibody was dissolved in 183.5 uL of sodium borate coating buffer. 104 uL of 3M ammonium sulfate was added to the antibody solution. 135 uL of the resulting antibody solution was added to the cleaned 20 uL bead aliquot and mixed at 37° C. for 24 hours. After incubation, the supernatant was removed using the magnetic separator, and 200 uL of PBS buffer containing 0.5% BSA and 0.05% Tween®20 was added to the beads. The beads were blocked overnight (~8 hours) at 37° C. The functionalized and blocked beads were washed 3 times with 1 mL PBS buffer containing 0.1% BSA and 0.05% Tween®20. The beads were diluted to 1.5 mL in PBS containing 0.1% BSA, 0.5% Tween®20, and 0.02% sodium azide. 100 uL aliquots were stored at 4° C. for later use.

Example 3

The following is an example of the preparation of TNF-alpha detection antibody (binding ligand) comprising a disulfide cleavable biotin linkage. 100 ug of TNF-alpha detection antibody (R&D Systems, AF-210-NA) was dissolved in 100 uL PBS pH 7.4 buffer. 164 uL of PBS pH 7.4 buffer was added to a tared vial containing 1 mg sulfo-NHS-ss-biotin, yielding a 10 mM stock solution. 1.34 uL of the 10 mM stock solution was added to the 100 uL antibody solution, equating to a 20-fold molar excess of the biotin label. The antibody/NHS-ss-biotin solution was mixed for 1 hr at room temperature. The antibody-ss-biotin conjugate was purified using a Zeba Desalt Spin Column. The purification was performed according to the Pierce protocol for product #89882. The purified conjugate was diluted up to 2 mL, making a 50 ug/mL stock solution. 50 uL aliquots of this 50 ug/mL solution were stored at −20° C. for later use.

Example 4

The following is an example of the capture of TNF-alpha on magnetic beads and formation of immunocomplexes. Solutions containing TNF-alpha were incubated with suspension of beads functionalized with capture antibody, as described in Example 2, for 1 h at 37° C. The beads were separated and washed three times in PBS. The beads were resuspended and incubated with 2 nM of detection antibody (binding ligand), prepared as described in Example 3, for 30 min at 37° C. The beads were separated and washed three times in PBS. The beads were then incubated with 200 pM of streptavidin-beta-galactosidase (converting agent) for 30 minutes at 37° C., separated, and washed three times in PBS.

Example 5

The following is an example of the cleaving of disulfide linkages in the TNF-alpha magnetic beads containing immunocomplex as prepared in Example 4. Magnetic beads containing the complete immunocomplex were washed three times in 100 uL of 5×PBS containing 0.1% Tween®20 for 2 minutes each time. The final wash volume was removed and 100 uL of 10 mM beta-mercaptoethanol containing 10 mM EDTA in PBS buffered solution was added to the beads. The beads were resuspended and incubated at 37° C. for 60 minutes while shaking (Jitterbug Model 130000; Boekel Scientific, Feasterville, Pa.) at 500 RPM. The entire liquid volume containing dissociated species was separated from the beads and stored at 4° C.

Example 6

The following is an example of the cleaving of a photo-cleavable linkage in a TNF-alpha magnetic bead containing an immobilized immunocomplex. A 96 well white Nunc Maxisorb plate on which were immobilized complete immunocomplexes, prepared similarly as described in the above Examples, except comprising photo-cleavable biotin linkages as opposed to disulfide cleavable biotin linkage on the detection antibody (binding ligand) were washed three times in 150 uL of 5×PBS containing 0.1% Tween®20 for 2 minutes with 500 RPM mixing on a VWR plate shaker each time. The final wash volume was removed and 50 uL of 1×PBS solution was added to the wells. The plate was placed ~5 cm from the UV light source (365 nm black light bulbs, 15 watt) for 30 to 60 minutes to activate the UV photo-cleavage of the biotin linkage. Photo-cleaved samples were transferred to a fresh plate following separation from the Nunc plate.

Example 7

The following is an example of the preparation of biotinylated array for capture of released reporter molecules (dissociated species). Optical fiber bundles approximately 5 cm long were polished on a polishing machine using 30, 9, and 1 micron-sized diamond lapping films. The polished fiber bundles were chemically etched in a 0.025 M HCl solution for 115 seconds, and then immediately submerged into water to quench the reaction. To remove impurities from etching, the etched fibers were sonicated for 5 seconds in water and washed in water for 5 mM The fibers were then dried under vacuum and exposed to air plasma for 5 minutes to clean and activate the glass surface. The arrays were silanized for 30 minutes in a 2% silanization solution that was prepared by mixing 950 uL of anhydrous ethanol, 50 uL of water, and 20 uL of 3-aminopropyl trimethoxysilane, and then washed with anhydrous ethanol for 10 min and dried under nitrogen. The amine silanized arrays were then biotinylated using the following procedure.

50 mg NHS-LC-biotin was dissolved in 1.1 mL anhydrous DMF to make a 100 mM stock solution. 1 mL of the 100 mM stock solution was diluted with 4 mL PBS buffer pH 7.4 to make 5 mL of a 20 mM working solution. The working solution was distributed in 500 uL aliquots into multiple 20 ml scintillation vials. Each vial can accommodate up to 8 arrays. The arrays were placed into the biotin solution and incubated with mixing for 60 minutes. The arrays were removed from the biotin solution and rinsed briefly with PBS buffer, followed by washing two times in 15 mL PBS buffer for 10 minutes. The biotinylated arrays were used immediately, or were stored for up to 2 days in PBS buffer for later use.

Example 8

The following is an example of the capture of streptavidin-beta-galactosidase reporter (dissociated species) released from the magnetic beads, as described above in Example 5, on functionalized fiber arrays prepared as described as described in Example 7. 100 uL cleaved samples were received in microtiter plates in a 10 mM beta-mercaptoethanol/PBS buffered solution. The 100 uL samples were transferred to 1.5 mL reaction tubes and capped. A small hole was made in the tube top, and a biotin functionalized fiber array was inserted into and suspended in the 100 uL sample. The arrays were incubated in the cleaved samples for 60 minutes at room temperature with 250 RPM mixing on a benchtop vortexer. Arrays were transferred to a second microtube containing PBS buffer, which was used to store the array for subsequent examination on the imaging system.

Example 9

Figure 17B:
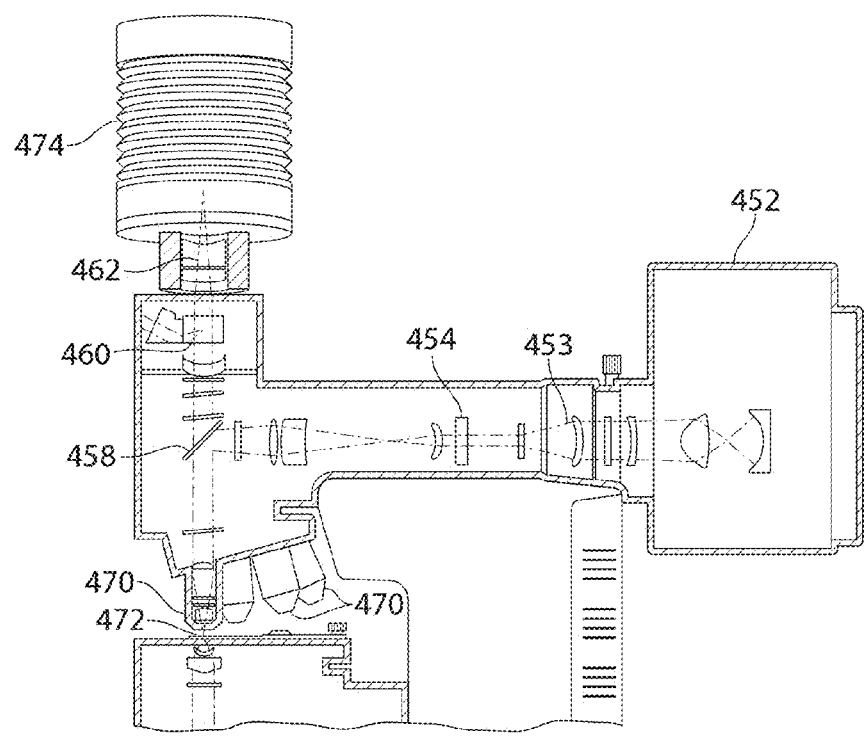

The following is an example of instrumental set-up that may be employed to analyze the fiber optic arrays prepared as described in Example 8. An upright epifluorescence microscope containing a mercury light source, filter cubes, objectives, and a CCD camera was used for acquiring fluorescence images. The set-up is similar to that as described above in FIG. 17A and is also pictured in FIG. 17B. The imaging system used for collecting the data integrated an Olympus BX-61 microscope system with a Cooke Corporation Sensicam QE CCD camera, 474. The BX-61 microscope is an upright microscope specifically designed for fluorescence detection. The scope housed UIS2 optics, which, in comparison to standard optics, offers increased signal-to-noise ratio, high light transmission, and diverse illumination capabilities. 10× and 20× UMPlanFl objectives (e.g., 470), which have a NA of 0.3 and 0.5, respectively, were installed on the BX-61 microscope. Wavelength specific filter sets are held in a cube, which is stored in a rotating wheel within the microscope. The BX-61 can hold 6 cubes for easy access to wavelengths specific for a number of fluorophores. Filter sets were purchased from Chroma Technology Corporation and are compatible with the cubes on the BX-61. The resorufin filter cube (Chroma Technology filter set #41010) was used for all of the enzyme amplification experiments described herein. This filter set uses a HQ577/10x excition filter, a 585 long-pass dichroic mirror, and a HQ620/60m emission filter.

A 6-axis mechanical platform was constructed beneath the microscope stage, which was used to house a non-reinforced silicone gasket material (sealing component) to be applied to the fiber optic array. Arrays were mounted on the microscope stage using a fiber array holder fabricated to secure and position the fiber array on the stage. A droplet of beta-galactosidase substrate (RDG) (precursor labeling agent molecule) was placed on the silicone gasket material, and put into contact with the distal end of the fiber array. The mechanical platform was used to move the silicone sheet into contact with the distal end of the etched optical fiber array, creating an array of isolated femtoliter reaction vessels. The number of wells that bound an enzyme molecule carried by the dissociated species correlated to the bulk dissociated species concentration, which, in turn, correlated with the concentration of TNF analyte in the initial fluid sample applied to the magnetic bead substrate.

Example 10

The following example outlines a standard procedure for a complete assay according to one embodiment of the present invention. The following procedure is a basic protocol that may be completed for any suitable sample comprising a plurality of analyte molecules, and the assay components (e.g., binding ligands, capture components, etc.) may be selected according to the methods described herein. This protocol or portions of it was followed when performing the assays discussed in Examples 11-14.

Chemical and Materials:

The following solutions should be prepared:

1. 1X PBS, pH 7.5: The solution should be 0.2 um filtered and may be diluted from 10×PBS (Omnipure cat#6506). To prepare, mix 100 mL 10×PBS and 900 mL Milli-Q water to form 1 liter total. The solution may be stored at room temperature.

2. Wash Buffer: The solution comprises 5×PBS+0.1% Tween®20 and was 0.2 um filtered. To prepare, mix 250 uL 100% Tween®20 and 125 mL Ultrapure Water and 125 mL 10×PBS to form 250 mL total. The solution may be stored at room temperature for up to one week 3. Detection Ab Buffer: The solution comprises 10% BSA+0.1% Tween®20. To prepare mix 5 g BSA, 45 mL 1×PBS and 50 uL 100% Tween®20 to form 50 mL total. The solution may be stored at 4° C. for up to one week 4. Dilution Buffer: The solution comprises 0.5% BSA+ 0.1% Tween®20. To prepare mix 2.5 mL 10% BSA, 47.5 mL 1×PBS, 47.5 uL 100% Tween®20 to form 50 mL total. The solution should be discarded after completing the assay.

5. Reporter Buffer: The solution comprises 1×PBS+1 mM $MgCl_2$. To prepare, mix 50 uL 1M $MgCl_2$, 50 mL 1×PBS to form 50 mL total. The solution should be stored at room temperature.

Preparation of the 96 Well Plate:

1. Obtain coupled beads (e.g., MyOne Beads (Invitrogen) prebound with αTNF Ab BAF210 (R&D Systems)). For example, the beads may be at 40 ug Ab/mg Dynabeads. Briefly vortex beads at approximately setting 8 until resuspended. Pipette up and down if necessary. Sonicate for approximately 10 seconds. Dilute beads to approximately 0.6 ng Ab/uL (vortex and sonicate all dilutions before use or subsequent dilution) in dilution buffer. Add 100 uL beads to appropriate wells of a 96-well plate. Add 100 uL of dilution buffer only to control wells.

2. Bead Preparation: Place plate on bar magnet and wait 30 seconds. Pour Dilution Buffer into a reagent reservoir. Using multichannel, remove all liquid from each well. Remove plate from bar magnet. Using multichannel, add 100 uL of Dilution buffer to each well. Pipette up and down vigorously 15 times to resuspend beads. Cover plate with hard plastic lid. Incubate on plate shaker at 500 RPM for 2 minutes. Repeat wash 2× more for a total of 3 washes.

Capture TNF-Alpha on Plate:

1. Dilute TNF-alpha (R&D systems 210-TA/CF) to appropriate concentration(s) in dilution buffer 2. Capture antigen: Aliquot 100 uL/well of TNF-alpha solution or dilution buffer only (for NSB wells) with single channel pipette. Cover plate with hard plastic lid. Incubate on plate shaker at 500 RPM for 1 hour. After 1 hour, beads will have partially settled. Pipette up and down vigorously 15 times to resuspend beads. Continue to incubate for 1 additional hour.

3. Wash Plate: Place plate on bar magnet and wait 30 seconds. Pour Wash Buffer into a reagent reservoir. Using multichannel remove all liquid from each well. Remove plate from bar magnet. Using multichannel, add 100 uL of wash buffer to each well. Pipette up and down vigorously 15 times to resuspend beads. Cover plate with hard plastic lid. Incubate on plate shaker at 500 RPM for 2 minutes. Repeat wash 2× more for a total of 3 washes.

Sandwich TNF-Alpha on Beads Using Biotin-Labeled TNF-Alpha Detection Antibody

1. Dilute releasable Biotin-labeled TNF-alpha detection Antibody (R&D systems BAF210—modified with Sulfosuccinimidyl 2-(biotinamido)-ethyl-1,3-dithiopropionate (ThermoFisher Scientific)) in dilution buffer to 0.3 ug/mL. In a 15 mL tube add and vortex to combine: 42 uL TNF-alpha Detection Antibody (50 ug/mL Stock) 7 mL Detection Ab buffer to form 7 mL total at 0.3 ug/mL TNF-alpha Antibody (2 nM)

2. Sandwich antigen by binding Detection antibody in each well: Dump TNF-alpha Antibody solution into a reagent reservoir. Aliquot 100 µL/well with multichannel pipette. Seal Plate with clear plastic lid. Incubate on plate shaker at 500 RPM for 1 hour.

3. Wash Plate: Place plate on bar magnet and wait 30 seconds. Using multichannel remove all liquid from each well. Remove plate from bar magnet. Using multichannel, add 100 uL of wash buffer to each well. Pipette up and down vigorously 15 times to resuspend beads. Cover plate with hard plastic lid. Incubate on plate shaker at 500 RPM for 2 minutes. Repeat wash 2× more for a total of 3 washes.

Label TNF-Alpha Detection Antibody with Signal Amplification Enzyme (Streptavidin-β-Galactosidase)

1. Dilute Streptavidin labeled TNF-alpha detection β-galactosidase (SA-β-gal) in dilution buffer to 500 pM: In a 15 mL tube add and vortex to combine 3.1 uL SA-β-gal (1.6 uM Stock), 10 mL Dilution buffer, to form 10 mL total of 500 pM SA-β-gal 2. Label Detection antibody with signal amplification reporter SA-β-gal: Dump SA-β-gal solution into a reagent reservoir. Aliquot 100 uL/well with multichannel pipette Seal Plate with clear plastic lid. Incubate on plate shaker at 500 RPM for 30 minutes.

3. Wash Plate: Place plate on bar magnet and wait 30 seconds. Using multichannel remove all liquid from each well. Remove plate from bar magnet. Using multichannel, add 100 uL of wash buffer to each well. Pipette up and down vigorously 15 times to resuspend beads. Cover plate with hard plastic lid. Incubate on plate shaker at 500 RPM for 5 minutes. Repeat wash 3× more for a total of 4 washes.

4. Transfer Beads: Place plate on bar magnet and wait 30 seconds. Using multichannel remove all liquid from each well. Obtain a second 96-well plate. Add 75 uL of wash buffer to each well of the original plate. Transfer entire volume from each well to the corresponding well of the second plate. Repeat previous steps to ensure complete bead transfer.

Cleave Detection Ab

1. Wash Plate: Place plate on bar magnet and wait 30 seconds. Using multichannel remove all liquid from each well. Remove plate from bar magnet. Using multichannel, add 100 uL of wash buffer to each well. Pipette up and down vigorously 15 times to resuspend beads. Cover plate with hard plastic lid. Incubate on plate shaker at 500 RPM for 2 minutes. Repeat wash 2× more for a total of 3 washes.

2. BME/EDTA Incubation: Dilute Beta Mercaptoethanol (BME) to 10 mM in PBS. Add EDTA to 10 mM final concentration. 0.2 uM-filter the solution. Using multichannel remove all liquid from each well. Add 50 uL of BME/EDTA to each well to be cleaved using single channel pipette. Incubate plate for 60 minutes at 37° C. Remove entire volume from each well and transfer to corresponding well in new plate. Discard unused BME/EDTA solution.

Example 11

Figure 20A:
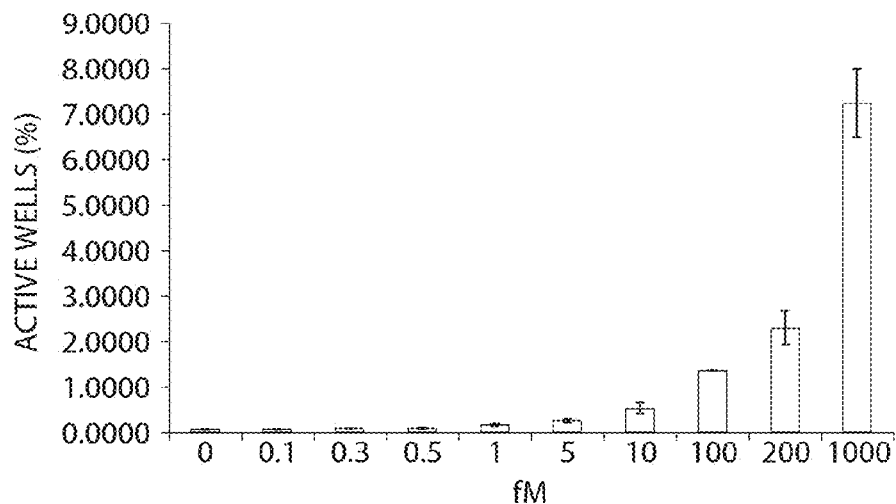
FIG. 20A shows a plot of the percent active wells against the concentration of TNF-alpha in serum samples, according to one example of the present invention.
Figure 20B:
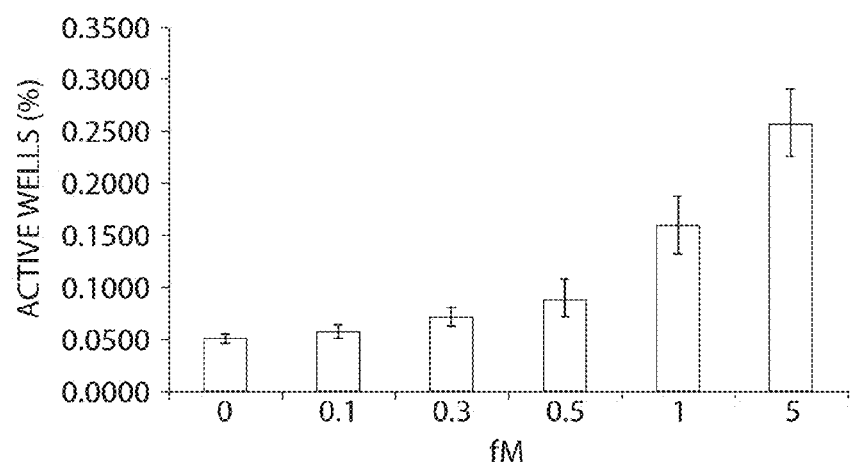
FIG. 20B shows a magnified view of the lower end of the graph in FIG. 20A.

The following is an example of the quantification of Tumor Necrosis Factor alpha (TNFα) using the protocol of Example 10. Magnetic beads coated in a monoclonal antibody to human TNF were prepared as described in Example 10. Solutions were then made containing human TNF at concentrations from 0 fM to 1000 fM spiked into bovine serum. The magnetic beads and TNF serum solutions were then combined in a microtiter plate to give final concentrations of magnetic beads of approximately 1 ug/well. The beads and serum were mixed at 37° C. for 1 hour. A magnet was then applied to the plate to separate the magnetic beads and serum, and the serum was removed. The beads were then subjected to cycles of washing, exposure to biotinylated detection antibody (first binding ligand), exposure to streptavidin-beta-galactosidase (second binding ligand), and magnetic separation as described in Example 10. The immunocomplex was then released from the beads by adding 100 ul of 10 mM beta-mercaptoethanol to each well of the plate. Solutions containing the dissociated species were then incubated with biotin functionalized fiber arrays to capture the released immunocomplexes. Single dissociated complexes were then detected by fluorescently imaging single beta-galactosidase molecules in the wells of the fiber arrays as described above in Examples. These images were then analyzed and the number of wells containing a single beta-galactosidase enzyme was determined. This number was converted to "% active wells" by ratio of the number of active wells to the total number of wells in the array. FIG. 20A shows a plot of % active wells against concentration of TNF in the serum samples. FIG. 20B shows a magnified view of the lower end of the graph in FIG. 20A. Statistical analysis of these data showed that the limit of detection for TNF (defined as 3 standard deviations of the background signal over background) was 0.2 fM, compared to 1250 fM for a standard ELISA using the same reagents. Table 1 shows the tabulated limit of detection (LOD) for the methods presented in FIGS. 20-23 as compared to a standard enzyme-linked immunosorbent assay (ELISA) using essentially similar reagents;

TABLE 1

| Protein | Presented Methods LOD (fM) | ELISA LOD (fm) | Improvement |
| --- | --- | --- | --- |
| TNF-alpha | 0.2 | 1250 | 4000× |
| PSA | 2 | 2000 | 1000× |
| IL-6 | 0.2 | 400 | 2000× |
| VEGF | 0.5 | 500 | 1000× |

Example 12

Figure 21:
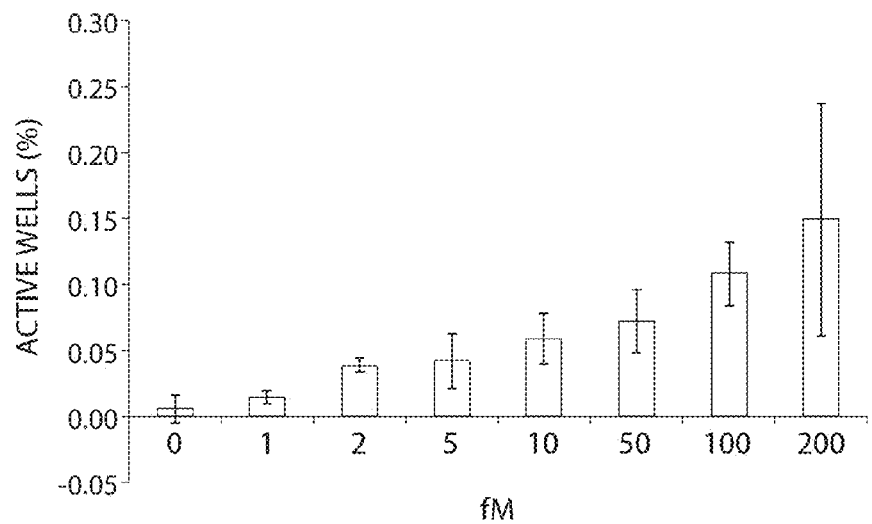
FIG. 21 shows a plot of the percent active wells against concentration of prostate specific antigen (PSA) in serum samples, in one embodiment of the present invention.

The following is an example of the quantification of Prostate Specific Antigen (PSA). Magnetic beads coated in a monoclonal antibody to human PSA were prepared using the method described above Example 10. Solutions were then made containing human PSA at concentrations from 0 fM to 200 fM spiked into bovine serum. The magnetic beads and PSA serum solutions were then combined in a microtiter plate to give final concentrations of magnetic beads of 0.7 ug/well. The beads and serum were mixed at 25° C. for 1 hour. The samples were then processed as for TNF in Example 11 and the % active wells arising from the released single enzymes was determined. FIG. 21 shows a plot of % active wells against concentration of PSA in the serum samples. The limit of detection for PSA is 2 fM, compared to 2000 fM for a standard ELISA using the same reagents (Table 1).

Example 13

Figure 22:
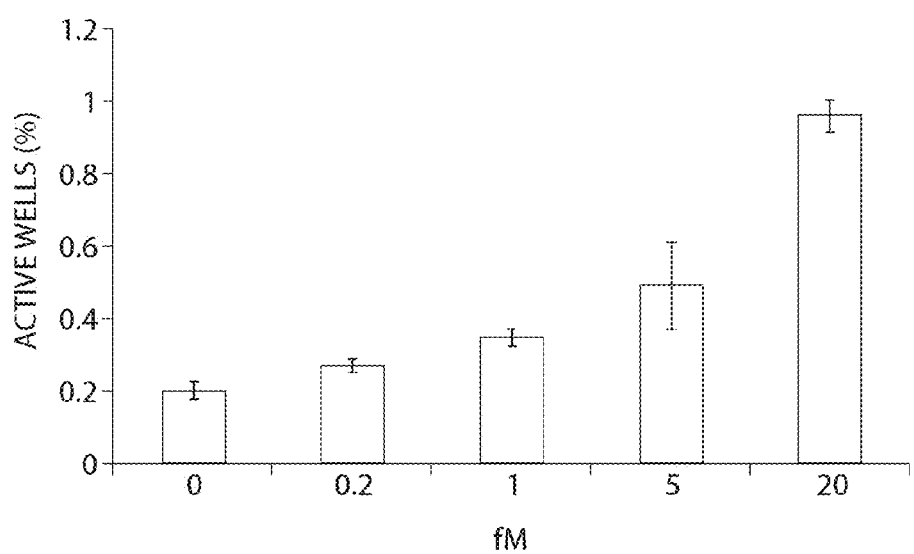
FIG. 22 shows a plot of the percent active wells against concentration of interleukin-6 (IL-6) in serum samples, in one embodiment of the present invention.

The following is an example of the quantification of Interleukin 6 (IL-6) Magnetic beads coated in a monoclonal antibody to human IL-6 were created using the method described above in Example 10. Solutions were then made containing human IL-6 at concentrations from 0 fM to 20 fM spiked into bovine serum. The magnetic beads and IL-6 serum solutions were then combined in a microtiter plate to give final concentrations of magnetic beads of 0.5 ug/well. The beads and serum were mixed at 25° C. for 1 hour. The samples were then processed as for TNF in Example 11 and the % active wells arising from the released single enzymes was determined. FIG. 22 shows a plot of % active wells against concentration of IL-6 in the serum samples. The limit of detection for IL-6 is 0.2 fM, compared to 400 fM for a standard ELISA using the same reagents (Table 1).

Example 14

Figure 23:
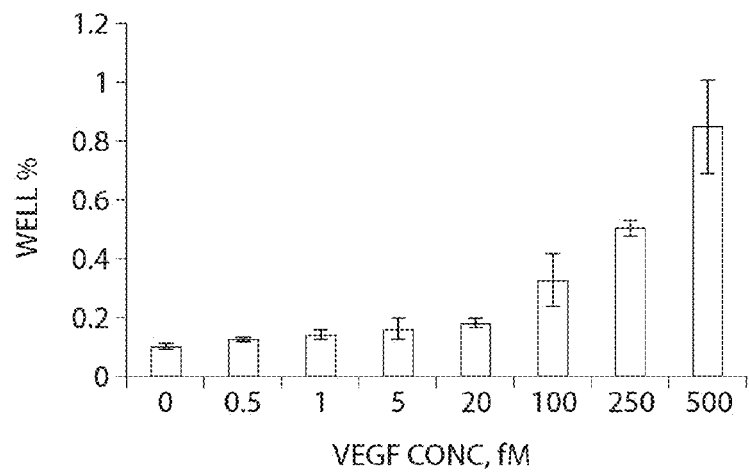
FIG. 23 shows a plot of the percent active wells against concentration of vascular endothelial growth factor (VEGF) in serum samples, in one embodiment of the present invention.

The following is an example of the quantification of Vascular Endothelial Growth Factor (VEGF). Magnetic beads coated in a monoclonal antibody to human VEGF were created using the method described above in Example 10. Solutions were then made containing human VEGF at concentrations from 0 fM to 1000 fM spiked into bovine serum. The magnetic beads and VEGF serum solutions were then combined in a microtiter plate to give final concentrations of magnetic beads of 0.5 ug/well. The beads and serum were mixed at 25° C. for 1 hour. The samples were then processed as for TNF in Example 11 and the % active wells arising from the released single enzymes was determined. FIG. 23 shows a plot of % active wells against concentration of VEGF in the serum samples. The limit of detection for VEGF is 0.5 fM, compared to 500 fM for a standard ELISA using the same reagents (Table 1).

Example 15

The following example presents results for several assays performed using the above described methods.

Figure 24:
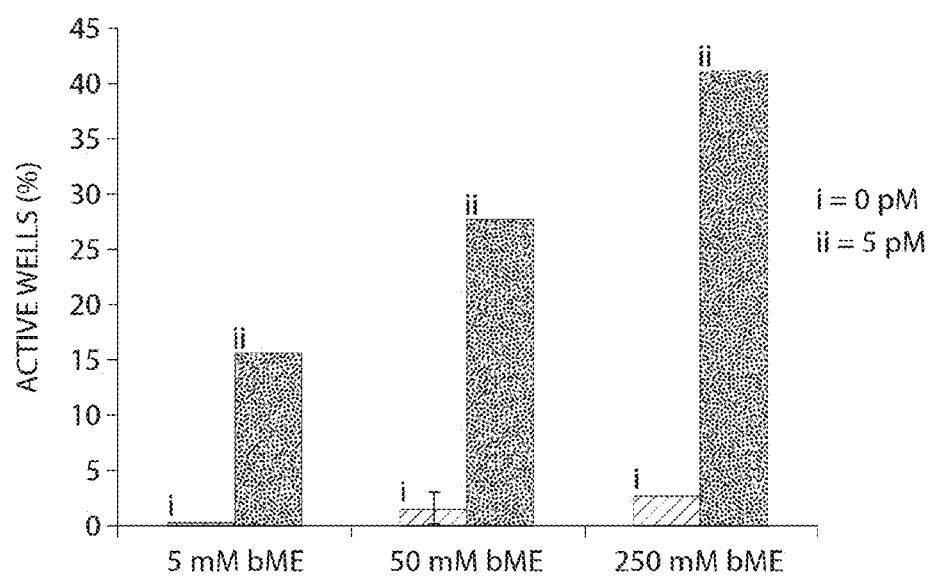
FIG. 24 is a graph depicting the effects of the concentration of beta-mercaptoethanol on the release of dissociated species, in one embodiment of the invention.

FIG. 24 describes the effect of the concentration of beta-mercaptoethanol on release of dissociated species, in one embodiment of the invention. The concentration of beta-mercaptoethanol (bME) used to release SbG was optimized for signal-to-background to enhance selectivity for specifically bound molecules. The released SbG was detected on single molecule array fiber bundles. In this example, 5 mM bME was determined to yield the best results based on signal-to-background ((ii)/(i)).

Figure 25:
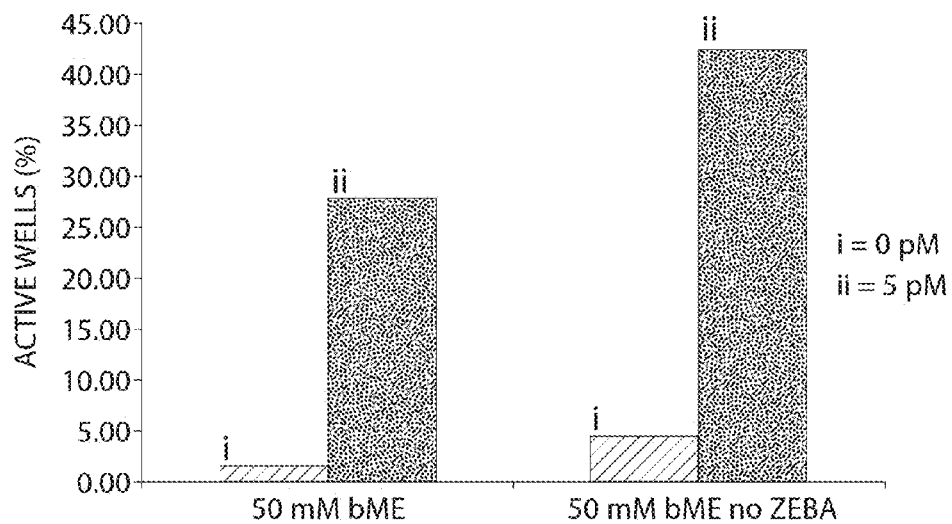
FIG. 25 is a graph depicting the effects of removing beta-mercaptoethanol before detection of the dissociated species on an array, in one embodiment of the invention.

FIG. 25 describes the effect of removing beta-mercaptoethanol before detection of the dissociated species on an array. In some cases, beta-mercaptoethanol may adversely affect the spectrum of the fluorescent product and/or may reduce the enzymatic activity of SbG. Beta-mercaptoethanol may be removed from the assay, in some cases, for example by either purifying the solution of SbG using a filtration column to remove the bME or by capturing the SbG on fiber arrays and washing the bME away. In this example, immunocomplexes of TNF-alpha were formed and released by bME as described in Example 11. The solution containing the dissociated complexes were (left) passed over a ZEBA column to remove the bME or (right) were left untreated. These solutions were then incubated with biotin functionalized fiber arrays (as described in Example 11) to capture dissociated SbG. The arrays were then washed in PBS buffer. The graph in FIG. 25 shows that the enzymatic activity of SbG was maintained with or without removal of the bME using a ZEBA gel filtration column. The capture and washing steps were sufficient to remove bME and to allow detection of single dissociated complexes. In this embodiment, the detection of SbG was not adversely affected by lack of removal of bME by gel filtration.

Figure 26:
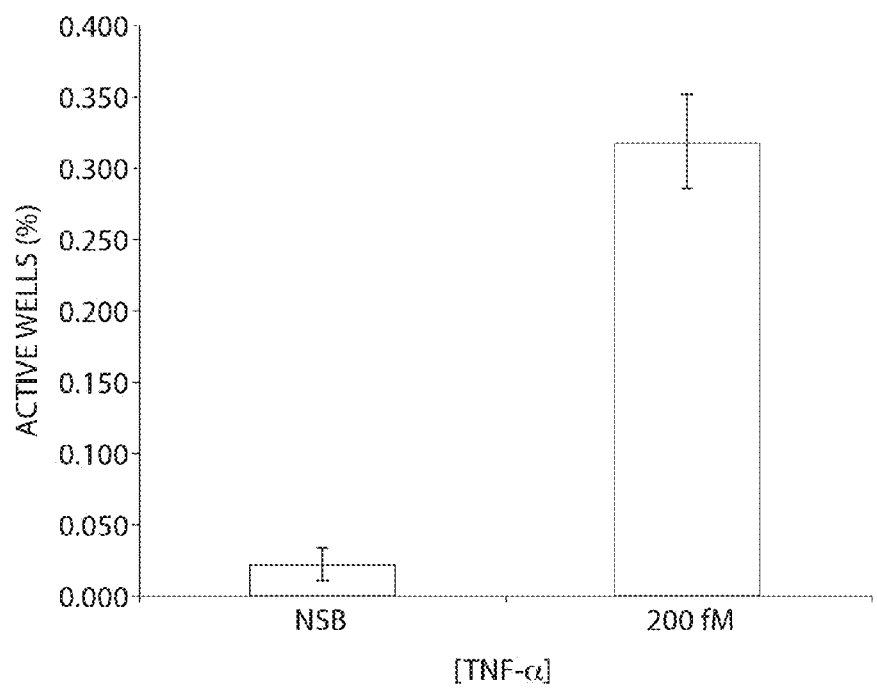
FIG. 26 is a graph depicting results of an example of the optimization of non-specific binding, according to one method of the present invention.

Non-specific binding (NSB) can be a major limitation on the sensitivity of an immunoassay. FIG. 26 shows that method of the present, in this embodiment, can be optimized to result in non-specific binding of less than about <0.1%. In some cases, the non-specific binding was reduced to less than about 10 wells in an 11,000-well image. In this example, when the immunocomplexes were formed directly on the fiber array (i.e., a one-step assay rather than a two-step, "capture-and-release", assay), non-specific binding was typically observed to be approximately 2%. Therefore the use of a two-step, "capture-and-release" assay, according to this embodiment, had a dramatic effect on lowering NSB resulting in greater sensitivity to low concentrations of analytes. This benefit of the method "capture-and-release" may be attributed to a number of factors, including, selective release by the dissociating agent of immunocomplexes over non-specifically bound molecules and advantageous surface chemistries of the first capture components.

Figure 27:
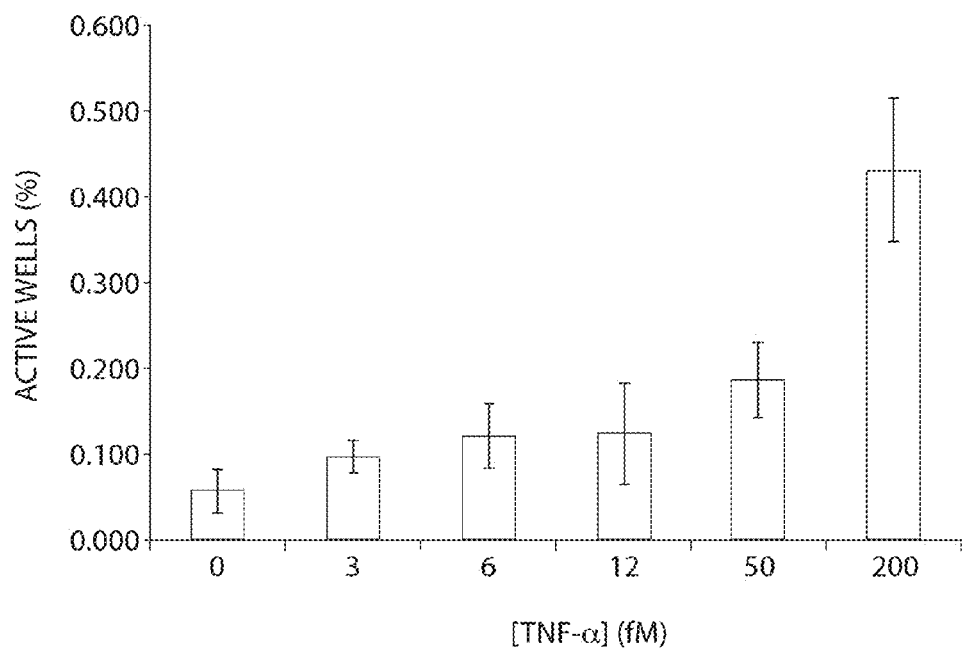
FIG. 27 is a graph depicting results of the detection of tumor necrosis factor-alpha (TNF-alpha) using a method/system of the present invention, according to one embodiment.
Figure 28:
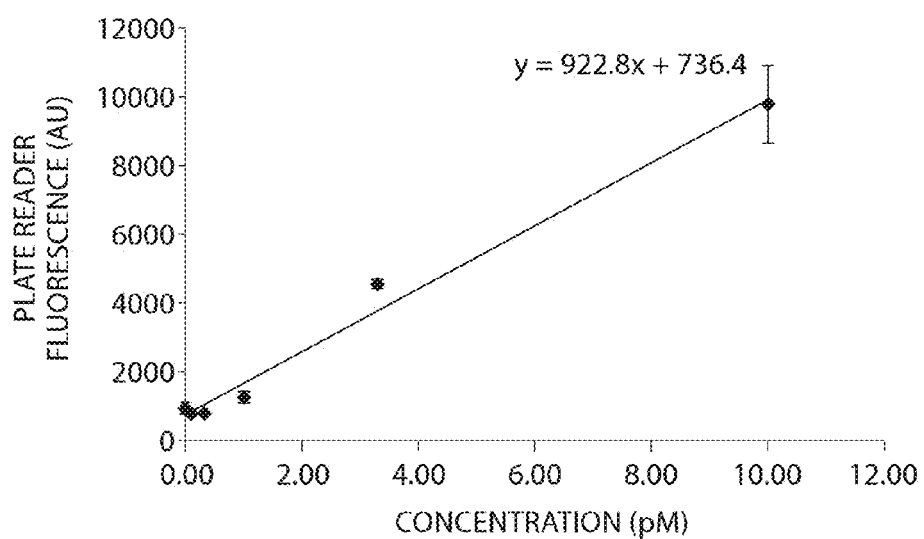
FIG. 28 is a graph depicting results of the detection of TNF-alpha using a standardized ELISA assay.
Figure 29:
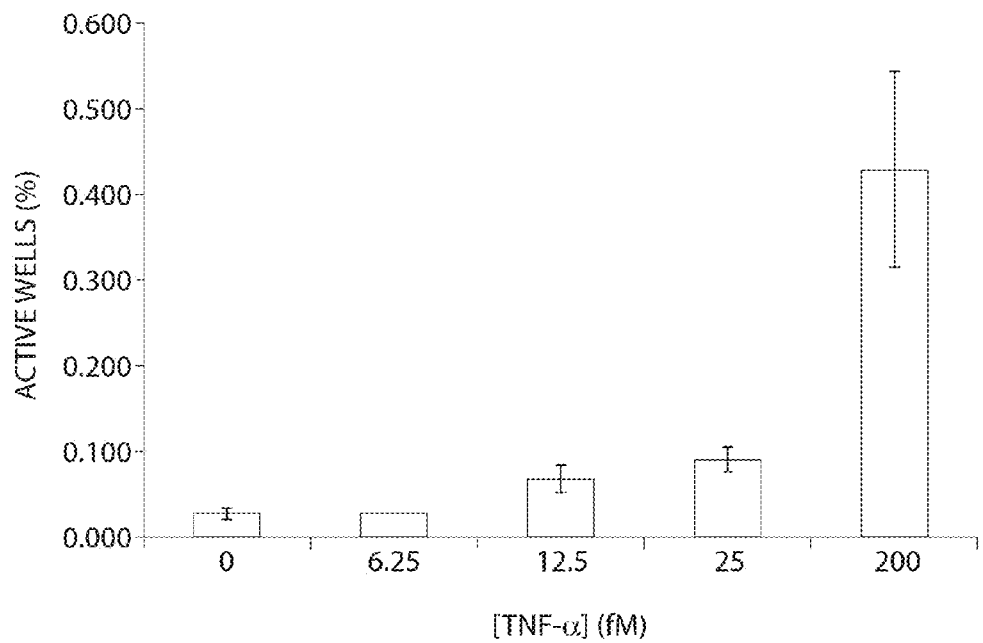
FIG. 29 is a graph depicting results of the detection of TNF-alpha using one embodiment of a method of the present invention, wherein the first substrate comprised beads and the beads were modified with antibody (Ab) stabilized with bovine serum albumin (BSA)

FIG. 27 shows results for the detection of TNF-alpha using the method described in Example 11. In this particular experiment, detection limits in single digit femtomolar ranges could be obtained as compared to $10^3$ femtomolar (e.g. 1250 fM) using the substantially the same reagents on a traditional ELISA plate assay (see FIG. 28, Maxisorb ELISA 96well plate, same reagents and incubation times as used in comparative assay, detection on a Tecan M200 plate reader). FIG. 29 shows a similar assay performed according to an embodiment of the inventive methods for the detection of TNF-alpha where the beads were modified with capture components comprising anti-TNF Ab stabilized with bovine serum albumin. In this example, the capture beads were prepared by reacting the beads with a 1:1 mixture of anti-TNF Ab and BSA, instead of pure anti-TNF Ab. The theoretical limit of detection in this assay was 8 fM.

Figure 30:
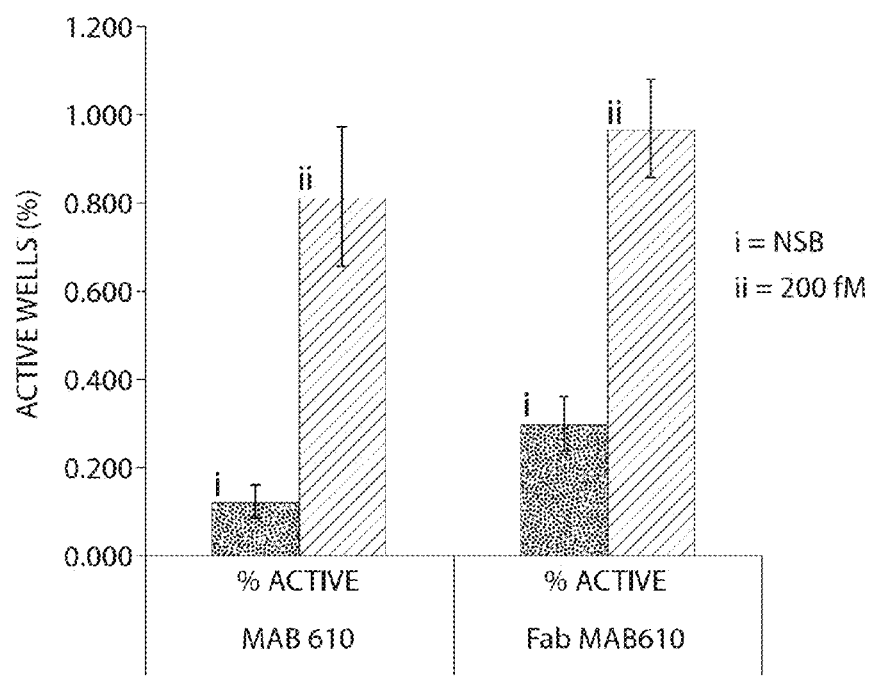
FIG. 30 is a graph depicting results of an assay involving the immobilization of Fab' fragments on anti-TNF (MAB610) generated using enzymatic degradation and purification, according to some embodiments of the present invention.

FIG. 30 shows results for the immobilization of Fab' fragments of an anti-TNF monoclonal antibody (MAB610) generated using enzymatic degradation and purification as the capture components immobilized on beads. The graph shows a comparison of detection of TNF using MAB610 on beads versus Fab' of MAB610 on beads where part of the immunocomplex comprising SbG was released with 10 mM bME. In this embodiment, higher signals but also higher NSB backgrounds were observed when using Fab' fragments.

Figure 31:
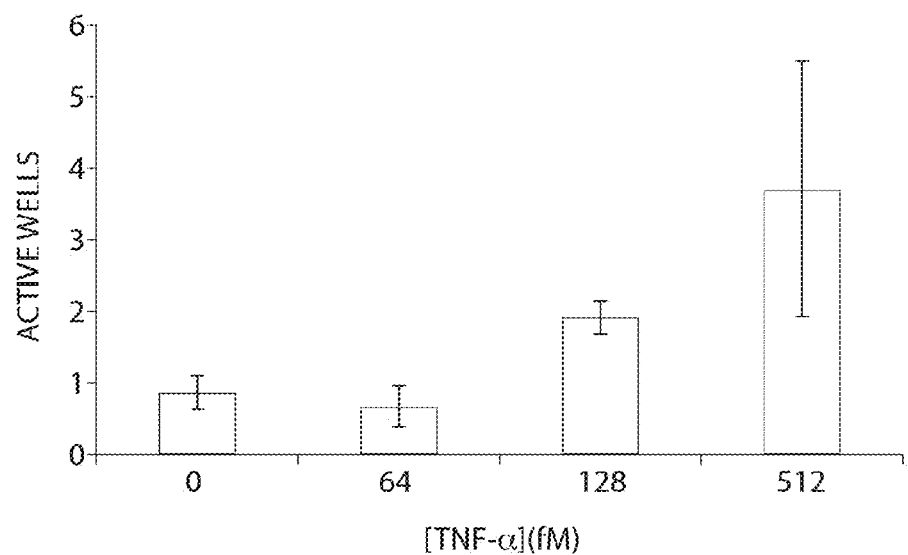
FIG. 31 is a graph depicting of an assay using a 96-well plate as the first substrate, followed by rebinding of a plurality of dissociated species to a biotin array, according to one embodiment of the present invention.

In another experiment, the TNF molecules were captured on an ELISA 96-well plate as a first substrate (Maxisorb, Nunc) as opposed to beads. In this case, SbG of the immobilized complex was released using bME and was detected on an optical fiber bundle. FIG. 31 shows a graph of results obtained using the plate as the first substrate. A substantially greater sensitivity was observed as compared to results obtainable using traditional ELISA methods, but less sensitivity was observed as compare to instances wherein the analyte molecules were captured on beads.

Figure 32:
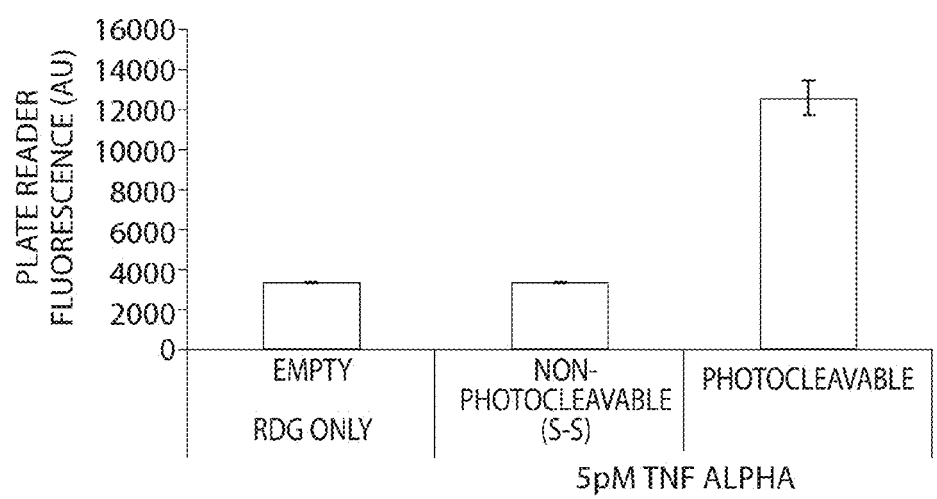
FIG. 32 is a graph depicting the results of method according to an embodiment of the present invention, wherein one of the binding ligands of the assay comprised a photocleavable linkage.

FIG. 32 shows the results for a method of the present invention, wherein one of the binding ligands of the assay comprised a photocleavable linkage. In this example, the immobilized complexes were formed on an ELISA 96-well plate as the first substrate. The plate was exposed to UV radiation, and a plurality of dissociated species was formed. The dissociated species were then detected/quantified using methods described herein. The graph depicts the plate reader fluorescence for three samples: i) no target analyte present, ii) target analyte present and the binding ligand does not comprise a photocleavable linker and iii) target analyte present and the binding ligand comprises a photocleavable linker.

Example 16

The following example describes a comparison between the methods/systems of the present invention and a traditional ELISA assay. Those of ordinary skill in the art will be familiar with the techniques associated with an ELISA assay.

Figure 33:
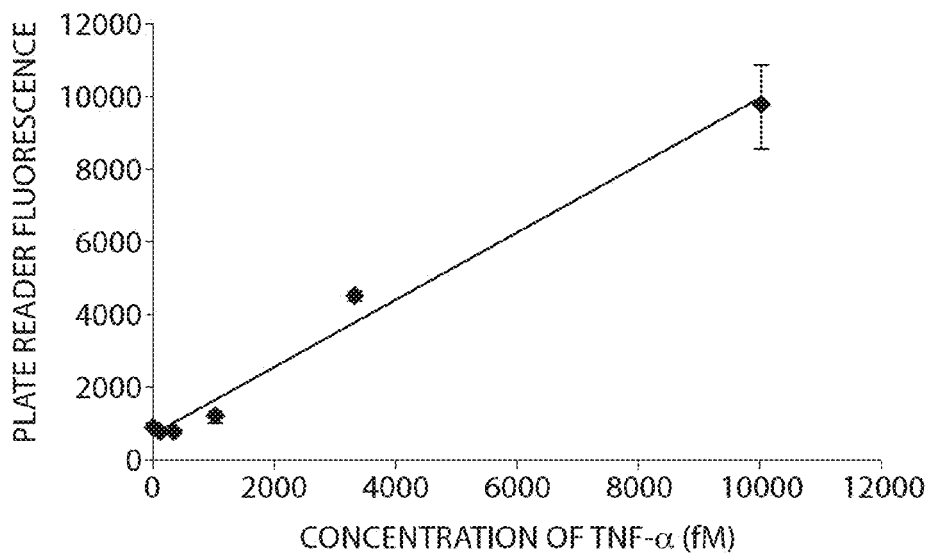
FIG. 33 is a graph depicting the detection of TNF-alpha using a standardized ELISA assay.

For the ELISA assay, a Maxisorb ELISA 96-well plate (Nunc) was employed. The ELISA plate was functionalized with monoclonal anti-TNF capture components. The substrate was then exposed to varying concentrations of TNF-alpha. The substrate was additionally exposed to a first binding ligand (polyclonal biotinylated anti-TNF antibody) and a second binding ligand (streptavidin-b-galactosidase). The conversion of substrate of b-galactosidase was detected on Tecan M200 plate reader. In this example, the limit of detection was approximately 1250 fM (see FIG. 33).

Figure 34:
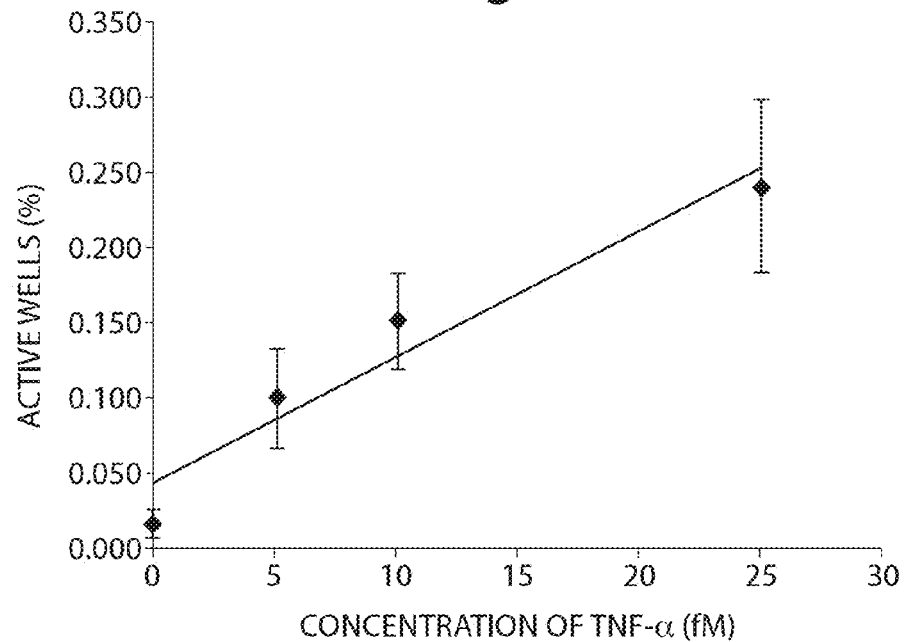
FIG. 34 is a graph depicting the detection of TNF-alpha using a method/system of the present invention, according to one embodiment.

To compare with an assay of the present invention, magnetic beads were provided which comprised monoclonal anti-TNF capture components. The beads were exposed to varying concentrations of TNF-alpha. The beads were additionally exposed to polyclonal disulfide-containing biotinylated anti-TNF antibody and streptavidin-b-galactosidase (SbG). At least a portion of the SbG was released from the beads using 10 mM beta-mercaptoethanol. The released complexes comprising SbG were captured on a fiber bundle well array comprising biotin capture components. Each reaction vessel was exposed to at least one precursor labeling agent molecule comprising resorufin-beta-D-galactopyranoside (RDG) that was converted to fluorescent resorufin upon exposure to SbG. The presence of at least one labeling agent molecules formed via the conversion of the precursor labeling agent molecule by the b-galactosidase of the SbG in the reaction vessels was detected using a fluorescence imaging microscope as described in Example 9. In this embodiment, the limit of detection was less than 5 fM (see FIG. 34).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed:

1. A method of quantifying a molecular species, comprising:
   providing a plurality of particles, wherein at least some of particles are associated with at least one molecule of the molecular species;
   partitioning at least a portion of the plurality of particles across a plurality of reaction vessels so that a statistically significant fraction of the reaction vessels contain no particles associated with a molecule of the molecular species and a statistically significant fraction of reaction vessels contain at least one particle associated with at least one molecule of the molecular species;
   detecting the presence or absence of a molecule of the molecular species in at least some of the reaction vessels and determining the percentage of reaction vessels which contain a molecule of the molecular species; and
   determining a measure of the quantity of the molecular species based on the percentage of reaction vessels which contain a molecule of the molecular species.

2. The method of claim 1, wherein either one or no molecules of the molecular species to be detected are immobilized with respect to a single particle.

3. The method of claim 1, further comprising an act of determining the concentration of molecular species in the fluid.

4. The method of claim 1, wherein each of the particles comprise a plurality of binding partners for the molecular species.

5. The method of claim 1, wherein the volume of each of the plurality of reaction vessels is between about 10 attoliters and about 100 picoliters.

6. The method of claim 1, wherein the volume of each of the plurality of reaction vessels is between about 1 femtoliter and about 1 picoliter.

7. The method of claim 1, wherein the volume of each of the plurality of reaction vessels is between about 10 femtoliters and about 100 femtoliters.

8. The method of claim 1, wherein the presence or absence of a particle associated with at least one molecule of the molecular species is detected directly.

9. The method of claim 1, wherein the presence or absence of a reaction vessel containing a particle associated with at least one molecule of the molecular species is detected indirectly.

10. The method of claim 9, wherein each of the plurality of reaction vessels is exposed to at least one precursor labeling agent molecule.

11. The method of claim 10, wherein the at least one precursor labeling agent molecule is converted to a labeling agent molecule when contained in a reaction vessel containing a particle associated with at least one molecule of the molecular species.

12. The method of claim 11, wherein the presence or absence of a molecule of the molecular species in a reaction vessels is detected by detecting the presence or absence of a labeling agent molecule in the reaction vessel.

13. The method of claim 1, wherein the molecular species are proteins.

14. The method of claim 1, wherein the molecular species are nucleic acids.

15. The method of claim 1, wherein the molecular species are small molecules.

16. A method of detecting a molecular species in a fluid sample, comprising:
    exposing the fluid sample to a plurality of particles, wherein at least some of the particles associate with molecules of the molecular species;
    partitioning at least a portion of the plurality of particles across a plurality of reaction vessels, wherein the plurality of particles are partitioned such that a statistically significant fraction of the reaction vessels contain no particles associated with a molecule of the molecular species and a statistically significant fraction of reaction vessels contain at least one particle associated with at least one molecule of the molecular species to be detected; and
    determining the presence or absence of a molecule of the molecular species in at least some of the reaction vessels.

17. The method of claim 1, wherein the plurality of particles are partitioned such that a statistically significant fraction of the reaction vessels contain no particles associated with a molecule of the molecular species and a statistically significant fraction of reaction vessels contain one particle associated with one molecule of the molecular species.

18. The method of claim 1, further comprising determining the number of the plurality of reaction vessels and/or fraction of the plurality of reaction vessels that contain or do not contain a particle associated with a molecule of the molecular species.

19. The method of claim 18, wherein the number or fraction of the plurality of reaction vessels that contain a particle associated with a molecule of the molecular species is related to the concentration of species in the fluid.

20. The method of claim 18, wherein the number or fraction of the plurality of reaction vessels that contain a particle associated with a molecule of the molecular species is directly proportional to the concentration of molecular species in the fluid.

21. The method of claim 16, wherein each of the plurality of particles comprises a plurality of binding partners for the molecular species.

22. The method of claim 16, wherein the volume of each of the plurality of reaction vessels is between about 10 attoliters and about 100 picoliters.

23. The method of claim 16, wherein the volume of each of the plurality of reaction vessels is between about 10 femtoliters and about 100 femtoliters.

* * * * *

UNITED STATES PATENT AND TRADEMARK OFFICE
CERTIFICATE OF CORRECTION

PATENT NO. : 8,846,415 B2
APPLICATION NO. : 13/527210
DATED : September 30, 2014
INVENTOR(S) : David C. Duffy et al.

It is certified that error appears in the above-identified patent and that said Letters Patent is hereby corrected as shown below:

In The Specification

At column 23, line 28 please replace "1 nL" with --1 mL--;

At column 49, line 31 please replace "concentration;" with --concentration,--; and At column 49, line 61 please replace "8 um" with --8 μm--.

Signed and Sealed this
Tenth Day of February, 2015

Michelle K. Lee
*Deputy Director of the United States Patent and Trademark Office*